United States Patent
Abbot et al.

(10) Patent No.: US 8,163,906 B2
(45) Date of Patent: Apr. 24, 2012

(54) DIHYDROQUINONE AND DIHYDRONAPHTHRIDINE INHIBITORS OF JNK

(75) Inventors: Sarah C. Abbot, San Francisco, CA (US); Geneviève N. Boice, Palo Alto, CA (US); Bernd Buettelmann, Palo Alto, CA (US); David Michael Goldstein, San Jose, CA (US); Leyi Gong, San Mateo, CA (US); Joan Heather Hogg, Sunnyvale, CA (US); Pravin Iyer, Mountain View, CA (US); Kristen Lynn McCaleb, Daly City, CA (US); Yun-chou Tan, San Jose, CA (US)

(73) Assignee: Roche Palo Alto, LLC, Palo Alto, CA (US)

( * ) Notice: Subject to any disclaimer, the term of this patent is extended or adjusted under 35 U.S.C. 154(b) by 521 days.

(21) Appl. No.: 12/152,432

(22) Filed: May 14, 2008

(65) Prior Publication Data
US 2008/0287458 A1   Nov. 20, 2008

Related U.S. Application Data

(60) Provisional application No. 60/930,054, filed on May 14, 2007.

(51) Int. Cl.
*C07D 471/04* (2006.01)
(52) U.S. Cl. .................................. 544/362; 546/123
(58) Field of Classification Search .................. None
See application file for complete search history.

(56) References Cited

U.S. PATENT DOCUMENTS

| 2003/0100507 A1* | 5/2003 | Gulati ........................ 514/12 |
| 2005/0148624 A1* | 7/2005 | Itoh et al. ................... 514/309 |

FOREIGN PATENT DOCUMENTS

| EP | 0 811 613 A1 | 12/1997 |
| WO | WO 96/33190 A1 | 10/1996 |
| WO | WO 98/21186 A1 | 5/1998 |
| WO | WO 03/051277 A2 | 6/2003 |
| WO | WO 03/051277 A3 | 6/2003 |
| WO | WO 2004/014388 A1 | 2/2004 |
| WO | WO 2005/014576 A1 | 2/2005 |
| WO | 2008/138918 | 11/2008 |

OTHER PUBLICATIONS

Haesslein et al., 1,3-Disubstituted-2-carboxy Quinolones: Highly Potent and Selective Endothelin A Receptor Antagonists, 10 Bioorg. & Med. Chem. Letts. 1487-90 (2000).*
Albaneze-Walker, J. et. al., "Improved Carbonylation of Heterocyclic Chlorides and Electronically Challenging Aryl Bromides," *Organic Letters* (2004) vol. 6 (13), pp. 2097-2100.
Bain, J. et. al. "The Specificities of Protein Kinase Inhibitors: An Update," *Biochem. J.* (2003) vol. 371, pp. 199-204.
Liu, M. et. al. "1,9-dihydro-9-hydroxypyrazolo[3,4-b]quinolin-4-ones as novel. Selective c-Jun N-terminal kinase inhibitors," *Bioorganic & Medicinal Chemistry Letters* (2006) vol. 16, pp. 2590-2594.
Chilean Office Action in related Chilean Patent Appl. 1393-2008.

* cited by examiner

*Primary Examiner* — Janet Andres
*Assistant Examiner* — Timothy R Rozof
(74) *Attorney, Agent, or Firm* — George W. Johnston; Dennis P. Tramaloni; Jennifer L. Kisko

(57) ABSTRACT

Compounds of formula I are effective modulators of JNK:

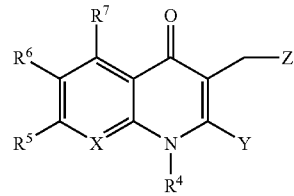

wherein
X is $CR^{11}$ or N;
Y is —$C(O)R^3$, 5-membered heteroaryl, or 5-membered heterocyclyl;
Z is phenyl, cycloalkyl, heterocyclyl or heteroaryl, and is substituted with $R^1$ and $R^2$;
$R^1$ and $R^2$ are each independently H, halo, CN, lower alkyl, or —$Y^1$—$Y^2$—$Y^3$—$R^8$, or $R^1$ and $R^2$ together form —$O(CH_2)_nO$—, where n is 1 or 2;
$Y^1$ is —O—, —C(O)—, —C(O)O—, —$C(O)NR^9$—, —$NR^9C(O)$—, —S—, —$SO_2$—, or a bond;
$Y^2$ is cycloalkylene, heterocycloalkylene, lower alkylene or a bond;
$Y^3$ is —O—, —C(O)—, —C(O)O—, —$C(O)NR^9$—, —$NR^9C(O)$—, —$SO_2$—, or a bond;
$R^8$ is H, lower alkyl, lower alkoxy, cycloalkyl, heterocloalkyl, or —$NR^9R^{10}$, wherein $R^8$ other than H is optionally substituted with lower alkyl, halo, —$CF_3$, or —OH;
$R^9$ and $R^{10}$ are each independently H or lower alkyl;
$R^3$ is OH, lower alkyl, lower alkoxy, (lower alkoxy)-lower alkoxy, or —$NR^9R^{10}$;
$R^4$ is lower alkyl, phenyl, heterocyclyl, cycloalkyl, heterocycloalkyl, or heteroaryl, and is optionally substituted with lower alkyl, hydroxy, lower alkoxy, halo, nitro, amino, cyano, or halo-lower alkyl;
$R^5$ and $R^6$ are each independently H, halo, cyano, lower alkyl, —$CF_3$, lower alkoxy, —$OCHF_2$, —$NO_2$, or —$NR^9R^{10}$;
$R^7$ is H, F, Cl, methyl, or OH;
$R^{11}$ is H, lower alkyl, lower cycloalkyl, or phenyl;
or a pharmaceutically acceptable salt thereof.

14 Claims, No Drawings

DIHYDROQUINONE AND DIHYDRONAPHTHRIDINE INHIBITORS OF JNK

RELATED APPLICATIONS

This application claims priority from U.S. Ser. No. 60/930,054, filed May 14, 2007, incorporated herein by reference in full.

FIELD OF THE INVENTION

This invention relates generally to the fields of medicinal chemistry and treatment of inflammatory disorders. More particularly, the invention relates to small molecule inhibitors of JNK, methods and formulations for inhibiting JNK and treating JNK-mediated disorders, and the like.

BACKGROUND OF THE INVENTION

JNK The c-Jun N-terminal kinases (JNKs) are members of mitogen-activated protein kinase family along with p38 and extracellular signal-regulated kinases (ERKs). Three distinct genes jnk1, jnk2 and jnk3) encoding 10 splice variants have been identified (Y. T. Ip and R. J. Davis, Curr. Opin. Cell Biol. (1998) 10:205-19). JNK1 and JNK2 are expressed in a wide variety of tissues, whereas JNK3 is mainly expressed in neurons, and to a lesser extent in heart and testes (D. D. Yang et al., Nature (1997) 389:865-70). Members of JNK family are activated by pro-inflammatory cytokines such as tumor necrosis factor α (TNF-α) and interleukin-1β (IL-1β), as well as environmental stresses. The activation of JNKs is mediated by its upstream kinases, MKK4 and MKK7, via dual phosphorylation of Thr-183 and Tyr-185 (B. Derijard et al., Cell (1994) 76:1025-37). It has been shown that MKK4 and MMK7 can be activated by the diverse upstream kinases, including MEKK1 and MEKK4, depending upon the external stimuli and cellular context (D. Boyle et al., Arthritis Rheum (2003) 48:2450-24). The specificity of JNK signaling is achieved by forming a JNK-specific signaling complex containing multiple components of the kinase cascade by use of scaffold proteins called JNK-interacting proteins (J. Yasuda et al., Mol. Cell. Biol. (1999) 19:7245-54). JNKs have been shown to play important roles in inflammation, T cell functions, apoptosis and cellular survival by phosphorylating specific substrates, including transcription factors such as c-Jun, the component of activator protein-1 (AP1) family, and ATF2, as well as non-transcription factors such as IRS-1 and Bcl-2 (A. M. Manning and R. J. Davis, Nat. Rev. Drug Discov. (2003) 2:554-65). Over-activation of JNK is believed to be an important mechanism in autoimmune, inflammatory, metabolic, neurological diseases as well as cancer.

Rheumatoid arthritis (RA) is a systemic autoimmune disease characterized by chronic inflammation of the joints. In addition to the joint swelling and pain caused by the inflammatory process, most RA patients ultimately develop debilitating joint damage and deformation. Several lines of compelling pharmacological and genetic evidence in cellular and animal models strongly suggest the relevance and importance of the activated JNK in the pathogenesis of RA. First, abnormal activation of JNK was detected in both human arthritic joints from RA patients (G. Schett et al., Arthritis Rheum (2000) 43:2501-12) and rodent arthritic joints from animal models of arthritis (Z. Han et al., J. Clin. Invest. (2001) 108:73-81). In addition, inhibition of JNK activation by selective JNK inhibitors blocked proinflammatory cytokines and MMP production in human synoviocytes, macrophages and lymphocytes (Z. Han et al., (2001) supra). Importantly, administration of the selective JNK inhibitors in rats with adjuvant arthritis (Z. Han et al., (2001) supra) or in mice with collagen-induced arthritis (P. Gaillard et al., J Med. Chem. (2005) 14:4596-607) effectively protected joints from destruction and significantly reduced paw swelling by inhibiting cytokine and collagenase expression.

Asthma is a chronic inflammatory disease of airways, characterized by the presence of a cellular inflammatory process and by bronchial hyper-responsiveness associated with structural changes of the airways (B. Bradley et al., J. Allergy Clin. Immunol. (1991) 88:661-74). This disorder has been shown to be driven by many cell types in the airways, including T lymphocytes, eosinophils, mast cells, neutrophils and epithelial cells (J. Bousquet et al., Am. J. Respir. Crit. Care Med. (2000) 161:1720-45). JNKs have emerged as promising therapeutic targets for asthma based upon the recent proof-of-concept studies: it has been shown that JNK inhibitors significantly blocked RANTES production in activated human airway smooth cells (K. Kujime et al., J. Immunol. (2000) 164:3222-28). More importantly, the JNK inhibitors showed good efficacy in chronic rat and mouse models for their abilities to reduce cellular infiltration, inflammation, hyper-responsiveness, smooth muscle proliferation, and IgE production (P. Nath et al., Eur. J. Pharmacol. (2005) 506:273-83; P. Eynott et al., Br. J. Pharmacol. (2003) 140:1373-80). These observations suggest important roles of JNKs in the allergic inflammation, airway remodeling process associated with hyper-responsiveness. Therefore, blockade of JNK activity is expected to be beneficial for the treatment of asthma.

Type 2 diabetes is the most serious and prevalent metabolic disease characterized by insulin resistance and insulin secretion impairment as a result of chronic low-level inflammation and abnormal lipid metabolism associated with oxidative stress. It has been reported that JNK activity is abnormally elevated in various diabetic target tissues under obese and diabetic conditions (J. Hirosumi et al., Nature (2002) 420: 333-36; H. Kaneto, Expert. Opin. Ther. Targets (2005) 9:581-92). Activation of the JNK pathway by pro-inflammatory cytokines and oxidative stresses negatively regulates insulin signaling via phosphorylation of insulin receptor substrate-1 (IRS-1) at $Ser^{307}$, therefore contributes to insulin resistance and glucose tolerance (J. Hirosumi et al., Nature (2002) supra; Y. Lee et al., J. Biol. Chem. (2003) 278:2896-902; Y. Nakatani et al., J. Biol. Chem. (2004) 279:45803-09). Compelling genetic evidence came from elegant animal model studies using $jnk^{-/-}$ mice crossed with either genetic (ob/ob) obese mice or dietary obese mice. Loss of JNK1 ($JNK1^{-/-}$), but not JNK2 functions ($jnk2^{-/-}$), protected obese mice from body gains, increased steady-state levels of blood glucose, and decreased plasma insulin levels (J. Hirosumi et al., Nature (2002) supra). These studies demonstrated the potential utility of JNK inhibitor in the treatment of obesity/type 2 diabetes.

Neurodegenerative diseases, such as Alzheimer's (AD), Parkinson's (PD) and Stroke are CNS diseases characterized by synaptic loss, neuronal atrophy and death. The JNK pathway leading to c-Jun activation has been shown to play a causal role in apoptosis of isolated primary embryonic neurons and multiple neuronal cell lines upon induction of a variety of stimuli (D. Bozyczko-Coyne et al., Curr. Drug Targets CNS Neurol. Disord. (2002) 1:31-49). Over-activation of JNK was observed in human brains from AD patients (J. Pei et al., J. Alzheimers Dis. (2001) 3:41-48) or rodent brain sections derived from animal models of neurodegenerative diseases (M. Saporito et al., J. Neurochem. (2000)

75:1200-08). For example, increased phospho-JNKs were detected in the post-mortem brains from the AD patients. Administration of JNK inhibitory peptide (JIP-1 peptide) in the rodent model of AD induced by β-amyloid peptide administration prevented the impairment of synaptic plasticity. In the animal models of PD (MPTP model), elevated phospho-MKK4 and phospho-JNKs were observed concomitantly with the neuronal cell death. Adenoviral gene transfer of JNK inhibitory peptide (JIP-1 peptide) into striatum of mice attenuated behavioral impairment by inhibiting MPTP-mediated JNK, c-Jun and caspase activation, therefore blocking neuronal cell death in the substantia nigra (X. Xia et al., *Proc. Natl. Acad. Sci. USA*. (2001) 98:10433-38). In addition, in the animal model of ischemic stroke induced by glutamate excitotoxicity, mice deficient in JNK3, but not JNK1 or JNK2, were resistant to kainic acid (glutamate receptor agonist)-mediated seizure or neuronal death (D. D. Yang et al., *Nature* (1997) 389:865-70). These data suggest JNK3 was mainly responsible for glutamate excitotoxicity, an important component in ischemic conditions. Taken together, data has emerged suggesting JNKs as attractive target for multiple CNS diseases associated with neuronal cell death.

Uncontrolled cellular growth, proliferation and migration along with de-regulated angiogenesis lead to the formation of malignant tumors. The JNK signal transduction pathway may not act exclusively in apoptosis, sustained JNK activation leading to API activation has recently been implicated to contribute to the cellular survival of specific cancer types such as glial tumors and BCL-ABL transformed B lymphoblasts (M. Antonyak et al., *Oncogene* (2002) 21:5038-46; P. Hess et al., *Nat. Genet*. (2002) 32:201-05). In the case of glial tumors, enhanced JNK/AP1 activity was seen in most of the primary brain tumor samples. For the transformed B lymphoblasts, BCL-ABL was shown to activate the JNK pathway which in turn up-regulated expression of anti-apoptotic bcl-2 gene. Interestingly, the multi-drug resistance and hyper-proliferation seen in treatment-refractory AML patients has been causally linked to the sustained JNK activity present in these AML samples (L. Cripe et al., *Leukemia* (2002) 16:799-812). Activation of JNK in leukemic cells resulted in induced expression of efflux pumps such as mdr1 and MRP1 responsible for multidrug resistance. Also, genes with a survival benefit in response to oxidative stress including glutathione-S-transferase π and γ-glutamyl cysteine synthase were also upregulated by the activated JNK pathway.

Accordingly, JNK modulators are useful in treating a variety of diseases and/or conditions.

SUMMARY OF THE INVENTION

One aspect of the invention is a compound of the formula:

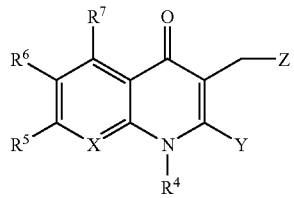

wherein
X is $CR^{11}$ or N;
Y is $-C(O)R^3$, 5-membered heteroaryl, or 5-membered heterocyclyl;
Z is phenyl, cycloalkyl, heterocyclyl or heteroaryl, and is substituted with $R^1$ and $R^2$;
$R^1$ and $R^2$ are each independently H, halo, CN, lower alkyl, or $-Y^1-Y^2-Y^3-R^8$, or $R^1$ and $R^2$ together form $-O(CH_2)_nO-$, where n is 1 or 2;
$Y^1$ is $-O-$, $-C(O)-$, $-C(O)O-$, $-C(O)NR^9-$, $-NR^9C(O)-$, $-S-$, $-SO_2-$, or a bond;
$Y^2$ is cycloalkylene, heterocycloalkylene, lower alkylene or a bond;
$Y^3$ is $-O-$, $-C(O)-$, $-C(O)O-$, $-C(O)NR^9-$, $-NR^9C(O)-$, $-SO_2-$, or a bond;
$R^8$ is H, lower alkyl, lower alkoxy, cycloalkyl, heterocycloalkyl, or $-NR^9R^{10}$, wherein $R^8$ other than H is optionally substituted with lower alkyl, halo, $-CF_3$, or $-OH$;
$R^9$ and $R^{10}$ are each independently H or lower alkyl;
$R^3$ is OH, lower alkyl, lower alkoxy, (lower alkoxy)-lower alkoxy, or $-NR^9R^{10}$;
$R^4$ is lower alkyl, phenyl, heterocyclyl, cycloalkyl, heterocycloalkyl, or heteroaryl, and is optionally substituted with lower alkyl, hydroxy, lower alkoxy, halo, nitro, amino, cyano, or halo-lower alkyl;
$R^5$ and $R^6$ are each independently H, halo, cyano, lower alkyl, $-CF_3$, lower alkoxy, $-OCHF_2$, $-NO_2$, or $-NR^9R^{10}$;
$R^7$ is H, F, Cl, methyl, or OH;
$R^{11}$ is H, lower alkyl, lower cycloalkyl, or phenyl;
or a pharmaceutically acceptable salt thereof.

Another aspect of the invention is a pharmaceutical composition comprising a compound of formula I and a pharmaceutically acceptable excipient.

Another aspect of the invention is method for modulating JNK activity, comprising contacting a cell that expresses JNK with a compound of formula I.

Another aspect of the invention is a method for treating inflammation, comprising administering to a subject in need thereof an effective amount of a compound of formula I.

DETAILED DESCRIPTION OF THE INVENTION

All publications cited in this disclosure are incorporated herein by reference in their entirety.
Definitions
Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$ alkyl. Examples of alkyl groups include, but are not limited to, methyl, ethyl, propyl, isopropyl, isobutyl, sec-butyl, tert-butyl, pentyl, n-hexyl, octyl, dodecyl, and the like. "Branched alkyl" refers to an alkyl moiety having at least one branch, for example, isopropyl, isobutyl, tert-butyl, and the like. Similarly, "lower alkoxy" refers to a moiety of the form $-OR$, and "acyl" refers to a moiety of the form $-C(O)R$, where R is lower alkyl.

"Alkylene" means a linear saturated divalent hydrocarbon moiety of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like. "Cycloalkylene" means a divalent hydrocarbon moiety of three to eight carbon atoms that incorporates a carbocyclic ring. Exemplary cycloalkylene moieties include, without limitation,

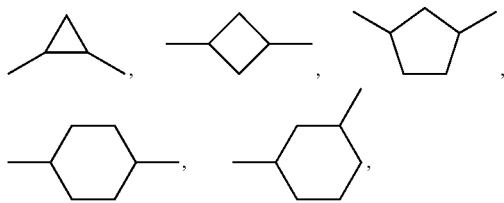

and the like. "Heterocycloalkylene" means a cycloalkylene moiety in which one, two, or three carbon atoms are replaced with heteroatoms (O, N, or S), where heterocycloalkylene moiety still contains at least two carbon atoms. Exemplary heterocycloalkylene moieties include, without limitation,

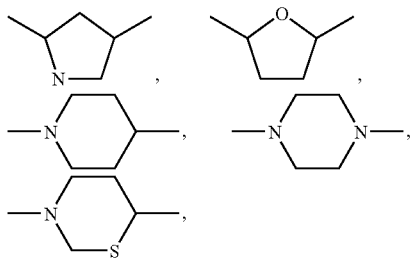

and the like.

"Alkylene dioxy" means a divalent moiety of the formula —O—R—O—, where R is alkylene as defined herein.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof.

"Cycloalkylalkyl" mean a moiety of the formula —$R^a$—$R^b$, where $R^a$ is alkylene and $R^b$ is cycloalkyl as defined herein.

"Heteroalkyl" means an alkyl moiety as defined herein, including a branched $C_4$-$C_7$ alkyl, wherein one, two or three hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl; when n is 1, $R^d$ is alkyl, cycloalkyl, or cycloalkylalkyl; and when n is 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethyl-ethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic moiety of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, thiophenyl, furanyl, pyranyl, pyridinyl, pyrrolyl, pyrazolyl, pyrimidyl, pyridazinyl, quinolinyl, isoquinolinyl, benzofuryl, benzofuranyl, benzothiophenyl, benzothiopyranyl, benzimidazolyl, benzoxazolyl, benzooxadiazolyl, benzothiazolyl, benzothiadiazolyl, benzopyranyl, indolyl, isoindolyl, indazolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

The terms "halo," "halogen," and "halide" are used interchangeably herein and refer to fluoro, chloro, bromo, and iodo.

"Haloalkyl" means alkyl as defined herein in which one or more hydrogen has been replaced with same or different halogen. Exemplary haloalkyls include —$CH_2Cl$, —$CH_2CF_3$, —$CH_2CCl_3$, perfluoroalkyl (e.g., —$CF_3$), and the like.

"Heterocyclyl" means a monovalent saturated moiety, consisting of one to two rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydroisoquinolinyl, tetrahydroquinolinyl, tetrahydrisoquinolinyl, and the like.

"Optionally substituted" means a substituent which is substituted independently with zero to three substituents selected from lower alkyl, halo, OH, cyano, amino, nitro, lower alkoxy, or halo-lower alkyl.

"Leaving group" means a group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids, such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate, sodium hydroxide, and the like.

The preferred pharmaceutically acceptable salts are the salts formed from acetic acid, hydrochloric acid, sulfuric acid, methanesulfonic acid, maleic acid, phosphoric acid, tartaric acid, citric acid, sodium, potassium, calcium, zinc, and magnesium.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "aminoprotecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. Skilled persons will know how to choose a group for the ease of removal and for the ability to withstand the following reactions.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

"Treating" or "treatment" of a disease state includes:

(i) preventing the disease state, i.e. causing the clinical symptoms of the disease state not to develop in a subject that may be exposed to or predisposed to the disease state, but does not yet experience or display symptoms of the disease state.

(ii) inhibiting the disease state, i.e., arresting the development of the disease state or its clinical symptoms, or (iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

A "JNK-mediated disorder" refers to a disease state that is caused by elevated activity or expression of JNK, and which may be relieved by inhibiting JNK activity. Examples of JNK-mediated disorders include rheumatoid arthritis, asthma, type 2 diabetes, Alzheimer's disease, Parkinson's disease, cellular hyperproliferation, and the like.

General Method

The invention provides compounds and compositions for treating inflammatory disorders, and methods of treating disorders mediated by JNK.

One aspect of the invention is compounds of the invention having general formula I:

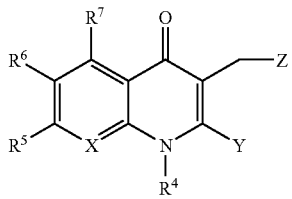

wherein

X is CR[11] or N;

Y is —C(O)R[3], 5-membered heteroaryl, or 5-membered heterocyclyl;

Z is phenyl, cycloalkyl, heterocyclyl or heteroaryl, and is substituted with R[1] and R[2];

R[1] and R[2] are each independently H, halo, CN, lower alkyl, or —Y[1]—Y[2]—Y[3]—R[8], or R[1] and R[2] together form —O(CH$_2$)$_n$O—, where n is 1 or 2;
  Y[1] is —O—, —C(O)—, —C(O)O—, —C(O)NR[9]—, —NR[9]C(O)—, —S—, —SO$_2$—, or a bond;
  Y[2] is cycloalkylene, heterocycloalkylene, lower alkylene or a bond;
  Y[3] is —O—, —C(O)—, —C(O)O—, —C(O)NR[9]—, —NR[9]C(O)—, —SO$_2$—, or a bond;
  R[8] is H, lower alkyl, lower alkoxy, cycloalkyl, heterocycloalkyl, or —NR[9]R[10], wherein R[8] other than H is optionally substituted with lower alkyl, halo, —CF$_3$, or —OH;
  R[9] and R[10] are each independently H or lower alkyl;

R[3] is OH, lower alkyl, lower alkoxy, (lower alkoxy)-lower alkoxy, or —NR[9]R[10];

R[4] is lower alkyl, phenyl, heterocyclyl, cycloalkyl, heterocycloalkyl, or heteroaryl, and is optionally substituted with lower alkyl, hydroxy, lower alkoxy, halo, nitro, amino, cyano, or halo-lower alkyl;

R[5] and R[6] are each independently H, halo, cyano, lower alkyl, —CF$_3$, lower alkoxy, —OCHF$_2$, —NO$_2$, or —NR[9]R[10];

R[7] is H, F, Cl, methyl, or OH;

R[11] is H, lower alkyl, lower cycloalkyl, or phenyl;

and the pharmaceutically acceptable salts thereof.

In presently preferred compounds of the invention, R[6] and R[7] are each H. In other preferred compounds of the invention, R[11] is also H.

In some presently preferred compounds of the invention, R[5] is halo, lower alkyl, or trifluoromethyl.

In some presently preferred compounds of the invention, R[4] is phenyl or heteroaryl. In some presently preferred compounds, Y is —C(O)R[3], where R[3] is lower alkoxy.

In one group of presently preferred compounds of the invention, Z is phenyl and R[2] is H. In some presently preferred compounds, R[1] is —Y[1]—Y[2]—Y[3]—R[8], where Y[1] is sulfonyl. In some presently preferred compounds of this group, Y[2] is heterocycloalkylene and Y[3] is —O—. In other presently preferred compounds, Y[2] is lower alkylene and Y[3] is a bond. In other preferred compounds, Y[1] is —C(O)NH—.

In another group of presently preferred compounds of the invention, Z is heterocyclyl.

Another aspect of the invention is a pharmaceutical composition, comprising a compound of Formula I in combination with a pharmaceutically acceptable excipient.

Another aspect of the invention is a method for treating a JNK-mediated disease, comprising administering an effective amount of a compound of Formula I to a subject in need thereof. A presently preferred method of the invention is the method of treating a JNK-mediated disease selected from the group consisting of rheumatoid arthritis and Crohn's disease.

Another aspect of the invention is a method for inhibiting the activity of JNK, comprising contacting said JNK with an effective amount of a compound of Formula I.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reaction described herein preferably are conducted under inert atmosphere, at atmospheric pressure, at a reaction temperature range of from about −78° C. to about 180° C., and most preferably and conveniently at room (or ambient) temperature, e.g., about 20° C.

Compounds of the invention are prepared according to the schemes shown below, and by using the procedures set forth in the examples. In the following schemes are depicted some of the possible synthetic routes leading to the compounds object of the invention. The radicals R[1], R[2], R[3], R[5], R[6], and R[7] are as defined above unless specified otherwise.

SCHEME I:

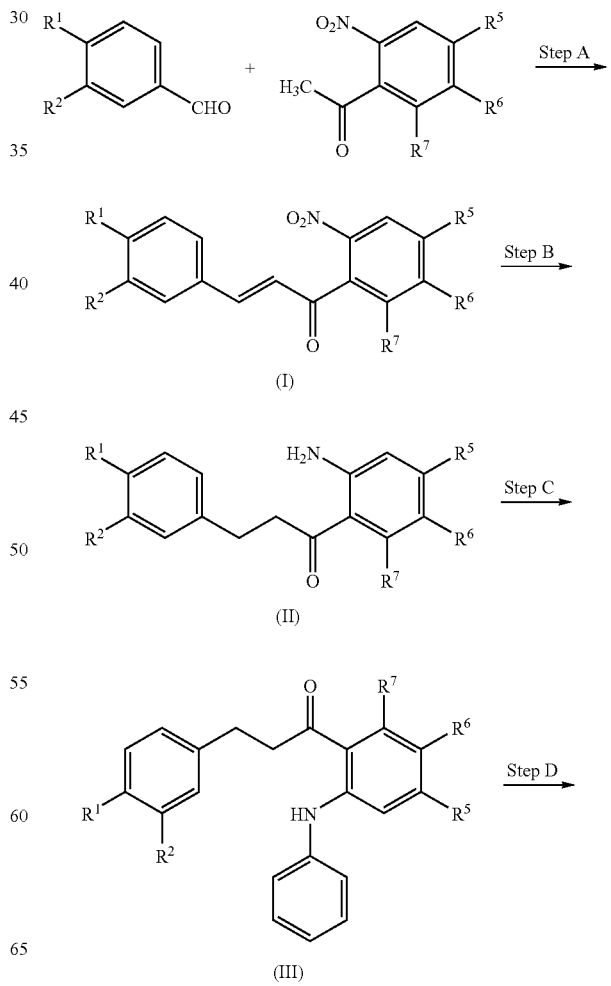

-continued

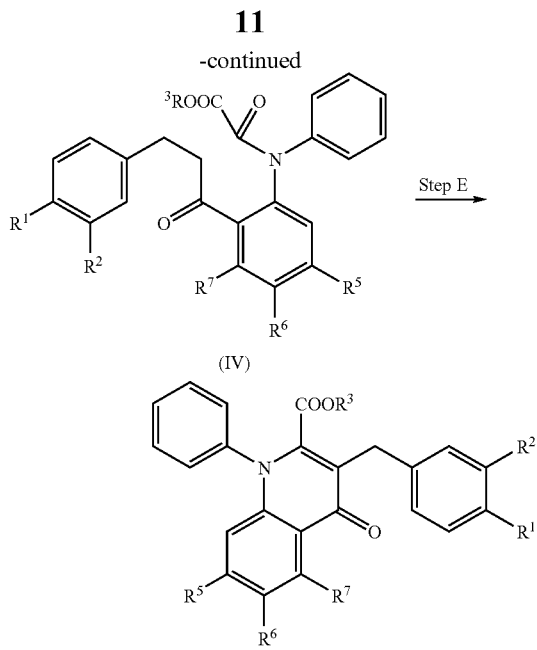

In Step A, a substituted benzaldehyde undergoes an aldol condensation with a substituted 2-nitroacetophenone in the presence of an inorganic base, such as NaOH, in a polar protic solvent such as a methanol/water mixture, to give the corresponding α,β-unsaturated ketone of formula (I). This product can then be reduced to the corresponding saturated aniline (II) by hydrogenation in the presence of a catalyst such as platinum (IV) oxide in a polar solvent such as methanol or tetrahydrofuran or a mixture of the above as described in Step B. The aniline (II) can be coupled with iodobenzene by heating at 160° C. in the presence of copper (0), potassium iodide and potassium carbonate in a polar solvent such as butyl ether as described in Step C. In Step D, the aniline of formula (IV) can be acylated by heating at reflux in the presence of an acyl chloride, such as methyl oxalyl chloride, in an apolar solvent such as toluene. The amide (IV) can cyclize by heating at reflux in a polar protic solvent, such as methanol, in the presence of an inorganic base such as potassium carbonate as described in Step E to afford the corresponding 1,4-dihydroquinoline.

SCHEME II:

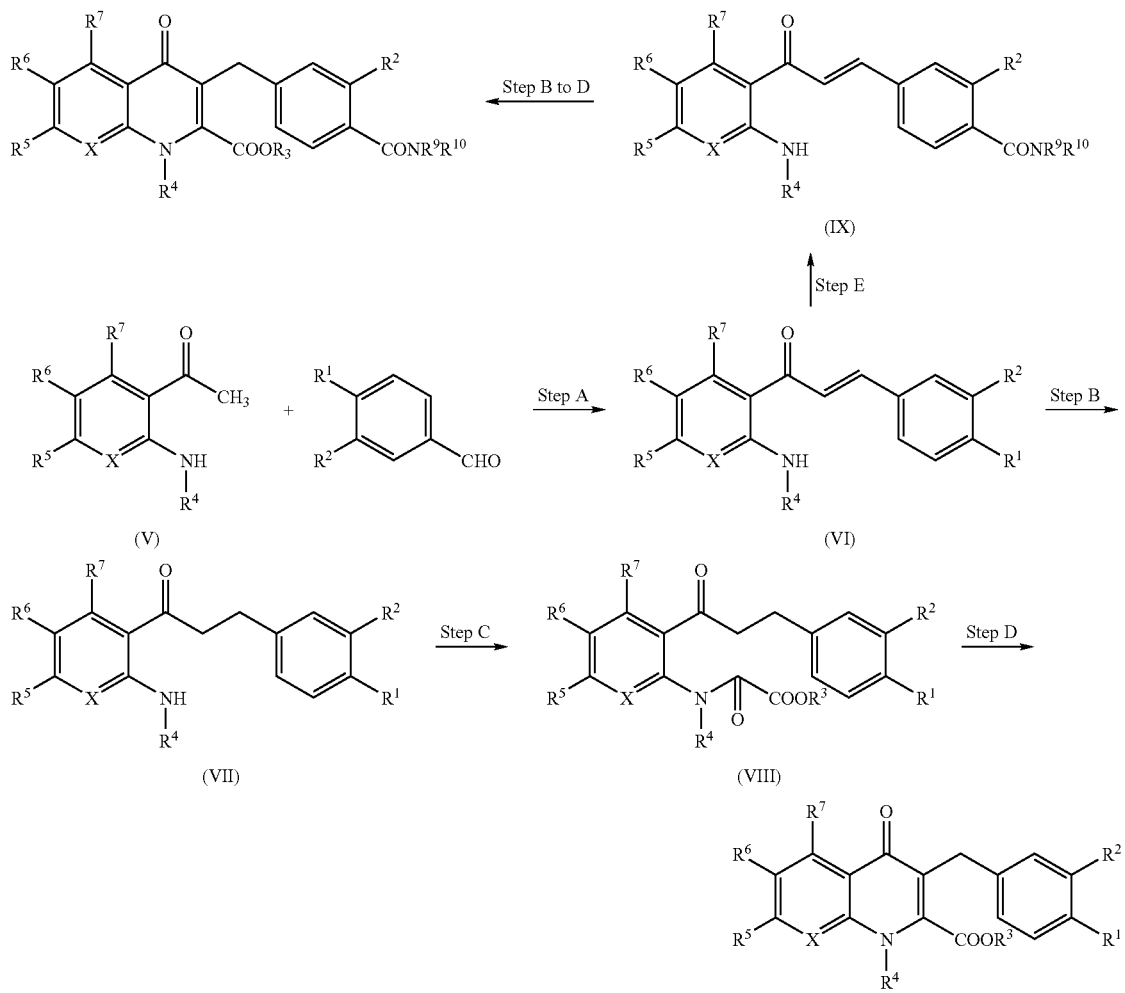

In Step A, a substituted benzaldehyde is condensed with a substituted acetophenone or 1-pyridin-3-yl-ethanone (V), in the presence of an inorganic base such as NaOH, in a polar protic solvent such as MeOH, to give the corresponding α,β-unsaturated ketone of formula (VI). This product can be reduced to the corresponding saturated ketone by hydrogenation in presence of a catalyst, such as platinum (IV) oxide, in a mixture of polar solvents, such as ethanol and EtOAc, as described in Step B. When $R^1$ or $R^2$ are chloro, this moiety can simultaneously be reduced using palladium on carbon as a catalyst instead of platinum (IV) oxide. In step C, the aniline (VII) can be acylated by heating at reflux in the presence of an acyl chloride such as methyl oxalyl chloride in an apolar solvent such as toluene. The amide (VIII) can cyclize by heating at reflux in a polar protic solvent, such as methanol, in the presence of an inorganic base, such as potassium carbonate, as described in Step D to afford the corresponding 1,4-dihydroquinoline. When $R^1$ is a carboxylic ester moiety in the coupling Step A, both the ester and corresponding carboxylic acid can be formed by hydrolysis; the acid can then be coupled with an amine $NHR^9R^{10}$ in the presence of coupling agents such as EDCI and BOP and an organic base such as diisopropylethylamine in a polar solvent such as tetrahydrofuran. The amide of generic formula (IX) can undergo the same Steps described above from B to D to give the corresponding 1,4-dihydroquinoline.

When $R^1$ is an ester moiety, the 1,4-dihydroquinoline of generic formula (X) can be hydrolyzed to the corresponding carboxylic acid (XI) in the presence of an inorganic base, such as lithium hydroxide, in a polar protic solvent, such as methanol, as described in Step A. The carboxylic acid (XI) can be coupled with an amine $NHR^9R^{10}$ in the presence of a coupling agent, such as BOP, and an organic base, such as diisopropylethylamine, in a polar solvent, such as tetrahydrofuran, to give the corresponding amide as described in Step B. When $R^1$ is a mercaptoalkyl moiety, the 1,4-dihydroquinoline of formula (IX) can be oxidized to the corresponding sulfone using as oxidizer OXONE™ in a mixture of polar solvents such as tetrahydrofuran, methanol and water as described in Step C.

The following Table lists representative compounds of the invention:

SCHEME III:

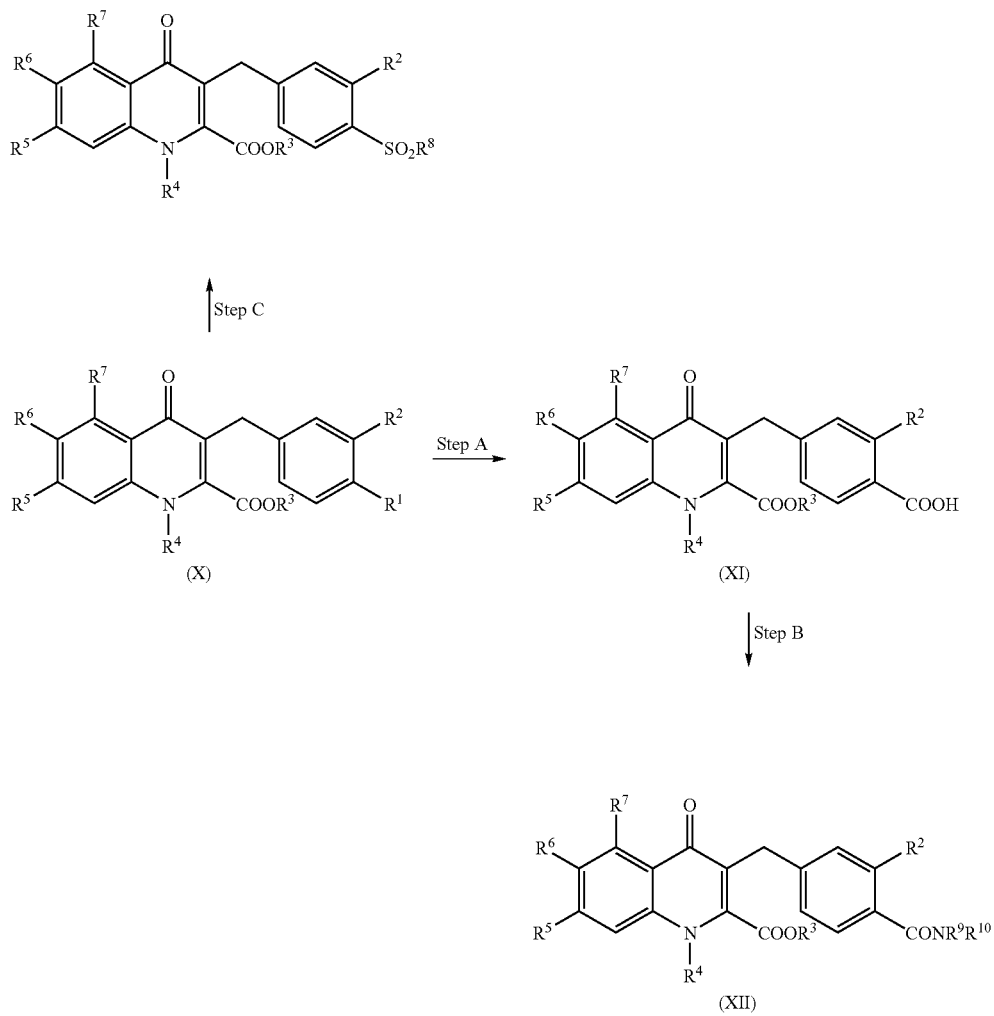

TABLE 1

| Compound | Structure | Data |
|---|---|---|
| 1 | 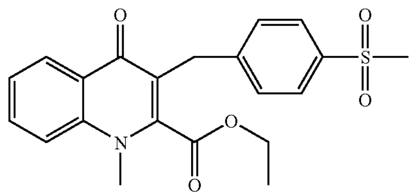 | |
| 2 | 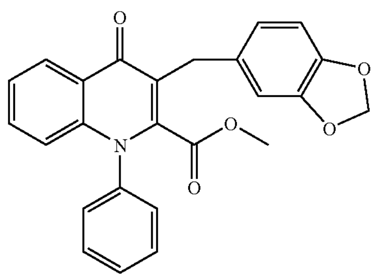 | |
| 3 | 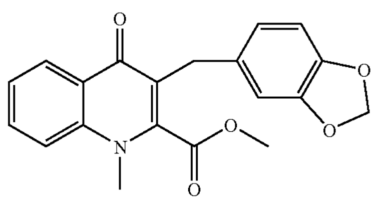 | |
| 4 | 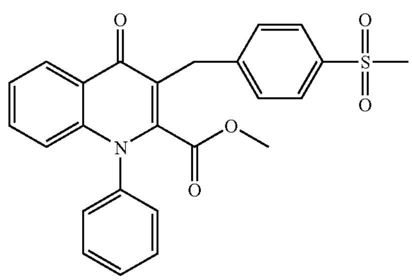 | |
| 5 | 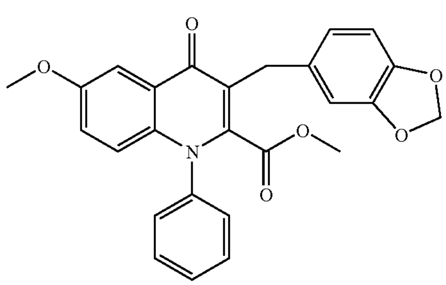 | |
| 6 | 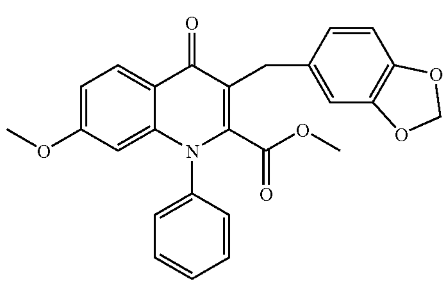 | |

TABLE 1-continued

EXEMPLARY COMPOUNDS

| Compound | Structure | Data |
|---|---|---|
| 7 | 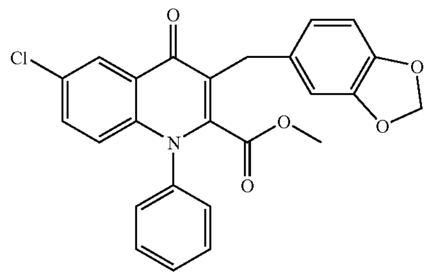 | |
| 8 | 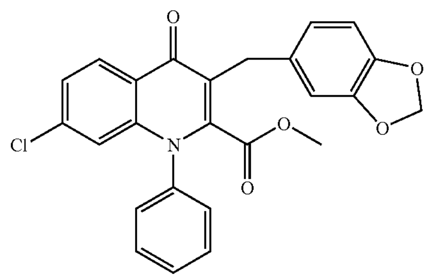 | |
| 9 | 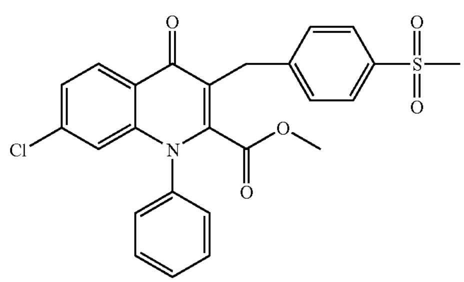 | |
| 10 | 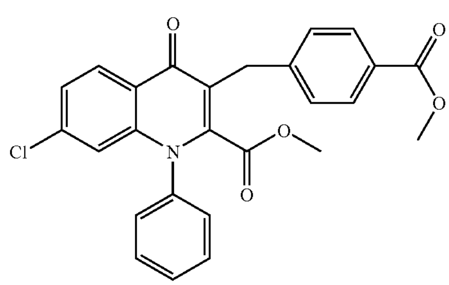 | |
| 11 | 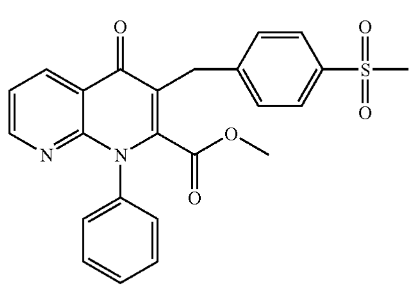 | |

TABLE 1-continued

EXEMPLARY COMPOUNDS

| Compound | Structure | Data |
|---|---|---|
| 12 | 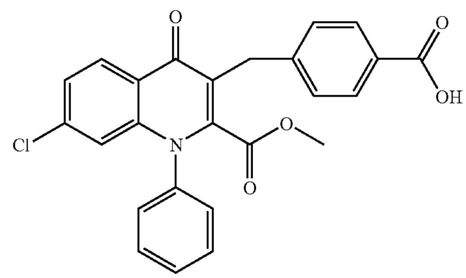 | |
| 13 | 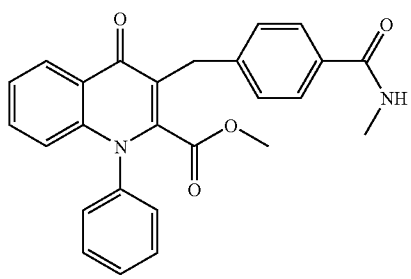 | |
| 14 | 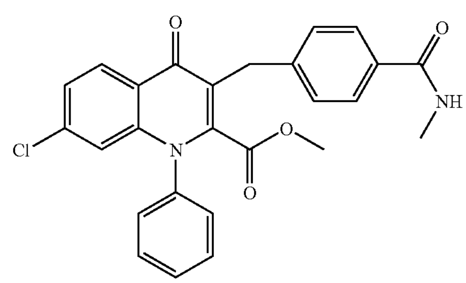 | |
| 15 | 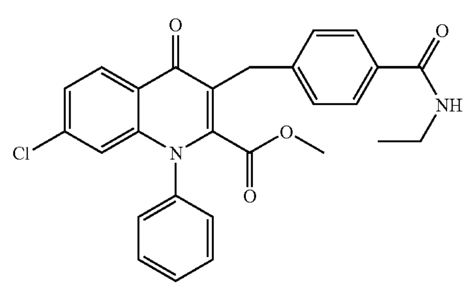 | |
| 16 | 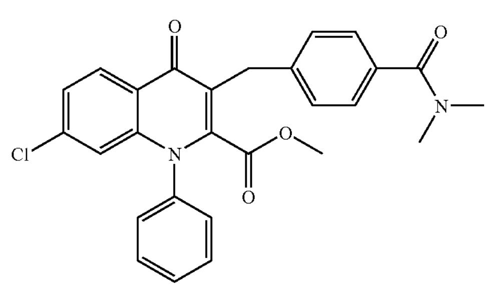 | |

TABLE 1-continued

EXEMPLARY COMPOUNDS

| Compound | Structure | Data |
|---|---|---|
| 17 | 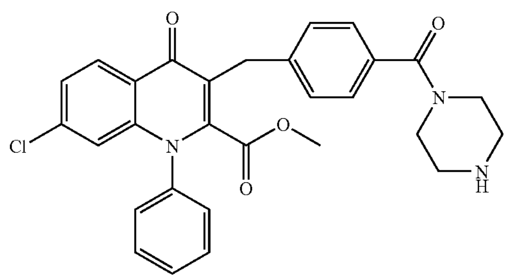 | |
| 18 | 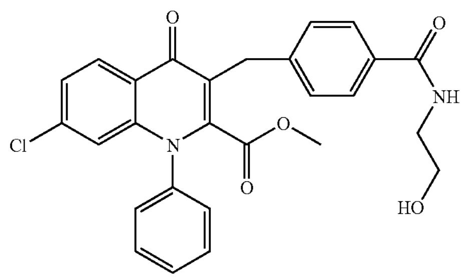 | |
| 19 | 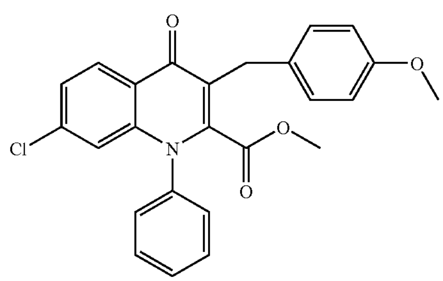 | |
| 20 | 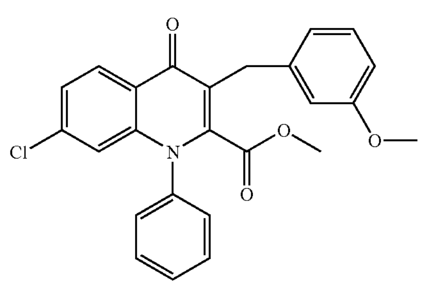 | |
| 21 | 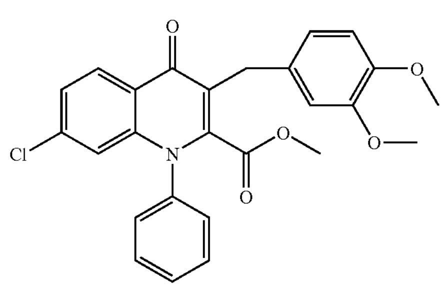 | |

TABLE 1-continued

EXEMPLARY COMPOUNDS

| Compound | Structure | Data |
|---|---|---|
| 22 | 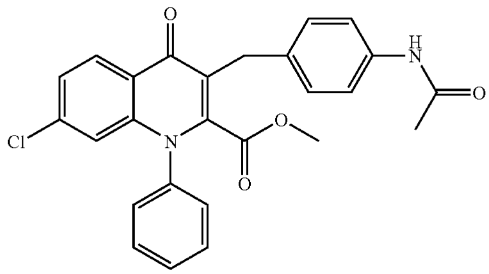 | |
| 23 | 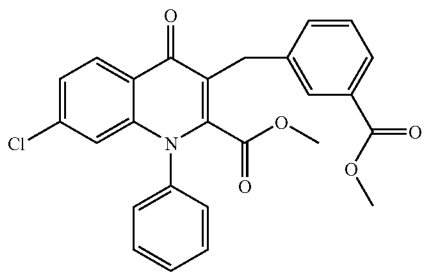 | |
| 24 | 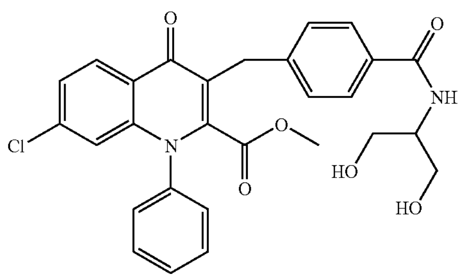 | |
| 25 | 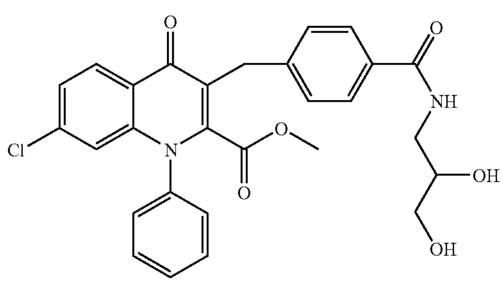 | |
| 26 | 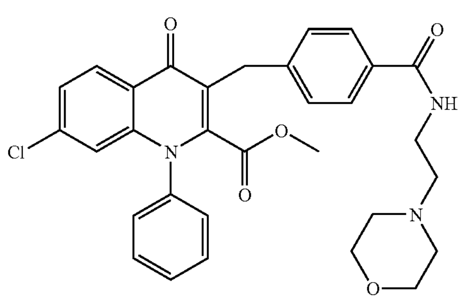 | |

TABLE 1-continued

EXEMPLARY COMPOUNDS

| Compound | Structure | Data |
|---|---|---|
| 27 | 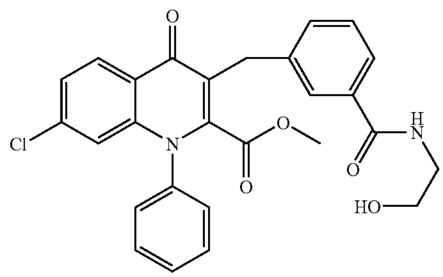 | |
| 28 | 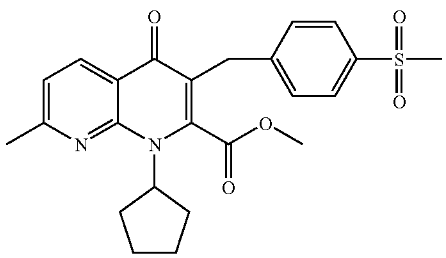 | |
| 29 | 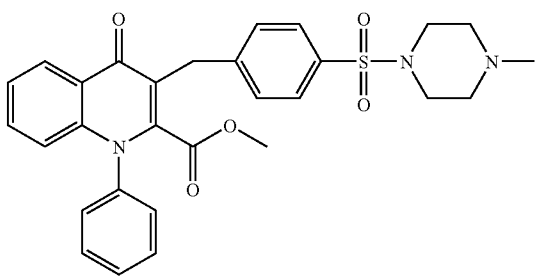 | |
| 30 | 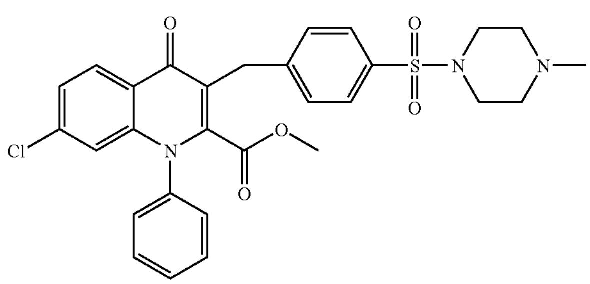 | |
| 31 | 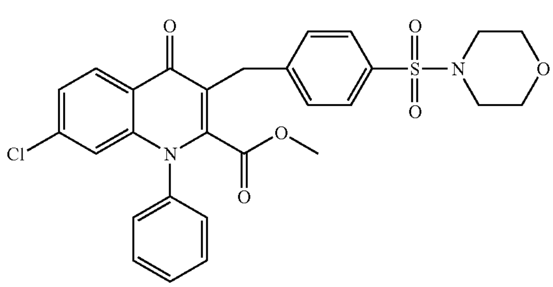 | |

TABLE 1-continued
EXEMPLARY COMPOUNDS
| Compound | Structure | Data |
|---|---|---|
| 32 | 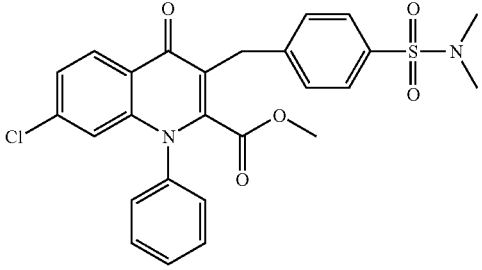 | |
| 33 | 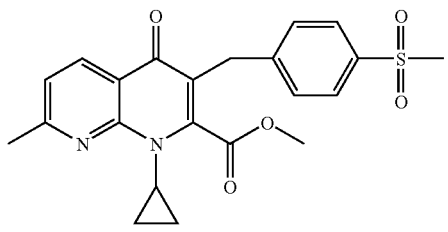 | |
| 34 | 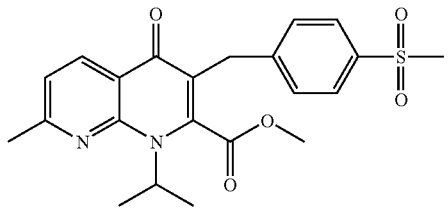 | |
| 35 | 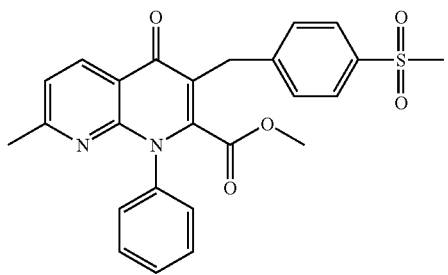 | |
| 36 | 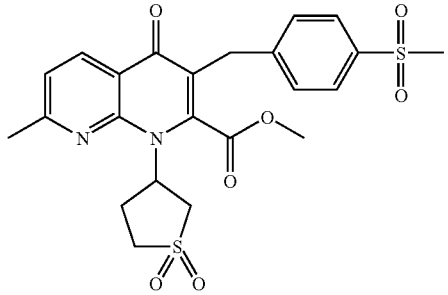 | |

TABLE 1-continued

EXEMPLARY COMPOUNDS

| Compound | Structure | Data |
|---|---|---|
| 37 | 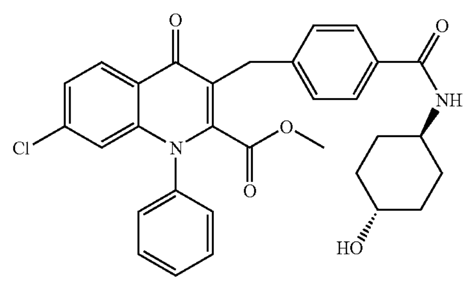 | |
| 38 | 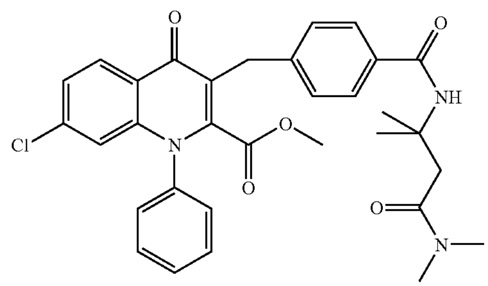 | |
| 39 | 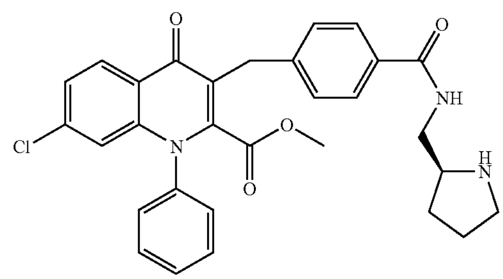 | |
| 40 | 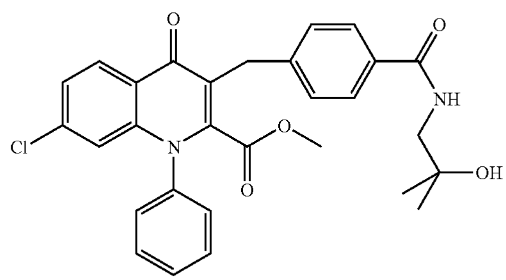 | |
| 41 | 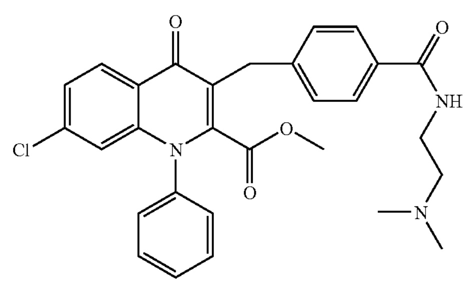 | |

TABLE 1-continued

EXEMPLARY COMPOUNDS

| Compound | Structure | Data |
|---|---|---|
| 42 | 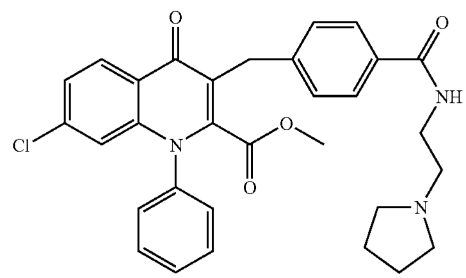 | |
| 43 | 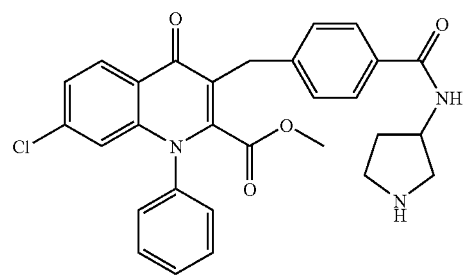 | |
| 44 | 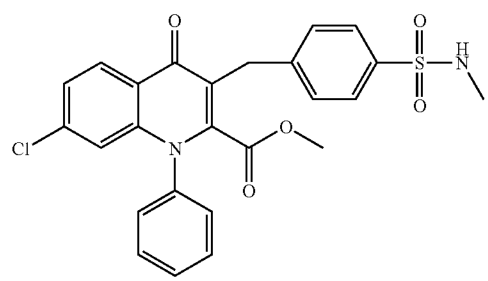 | |
| 45 | 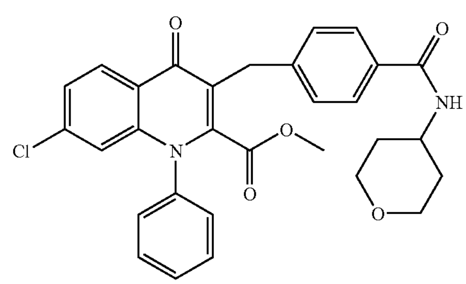 | |
| 46 | 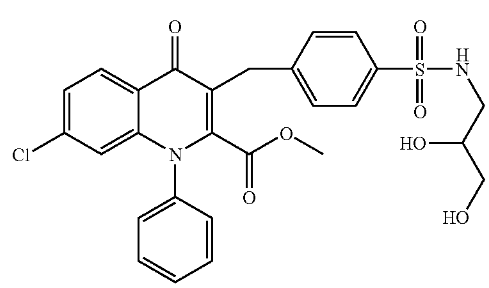 | |

TABLE 1-continued

EXEMPLARY COMPOUNDS

| Compound | Structure | Data |
|---|---|---|
| 47 | 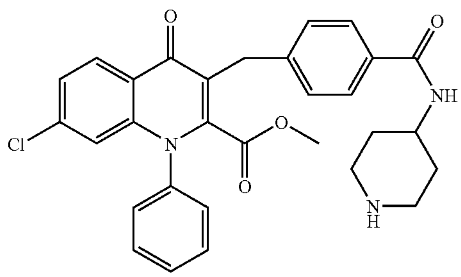 | |
| 48 | 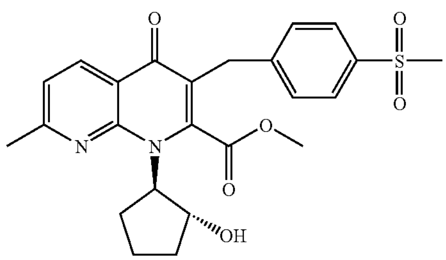 | |
| 49 | 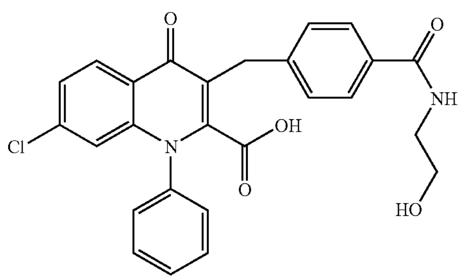 | |
| 50 | 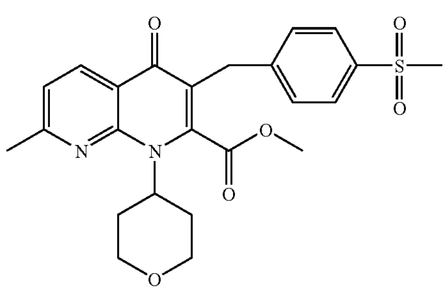 | |
| 51 | 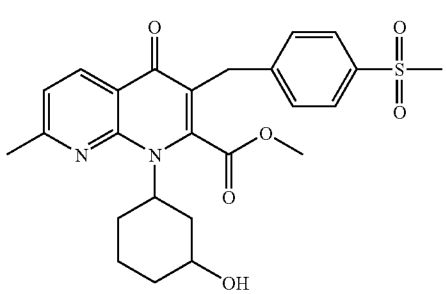 | |

TABLE 1-continued

EXEMPLARY COMPOUNDS

| Compound | Structure | Data |
|---|---|---|
| 52 | 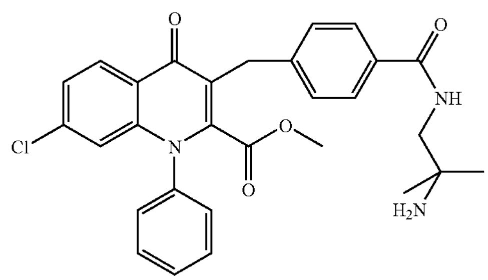 | |
| 53 | 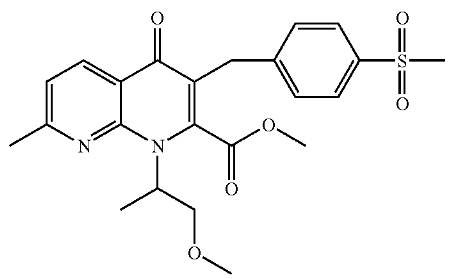 | |
| 54 | 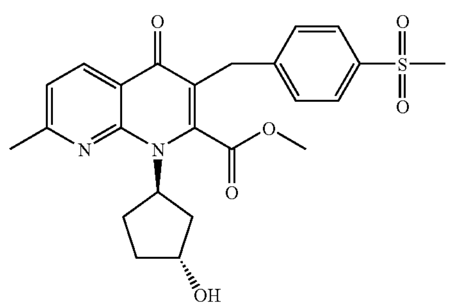 | |
| 55 | 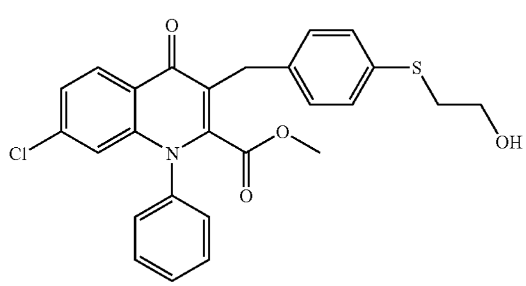 | |
| 56 | 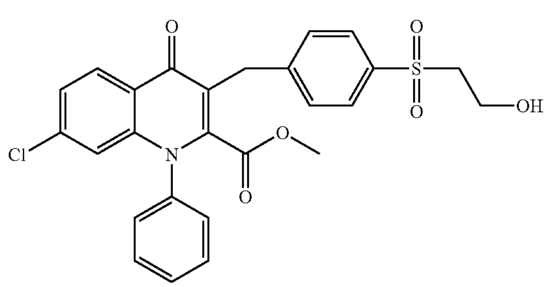 | |

TABLE 1-continued

EXEMPLARY COMPOUNDS

| Compound | Structure | Data |
|---|---|---|
| 57 | 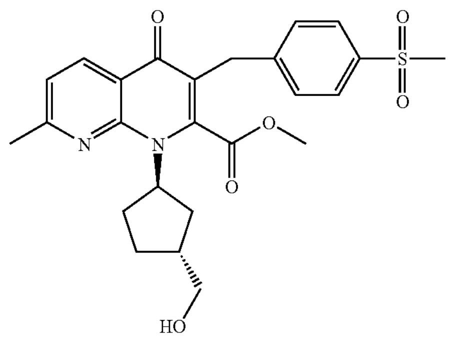 | |
| 58 | 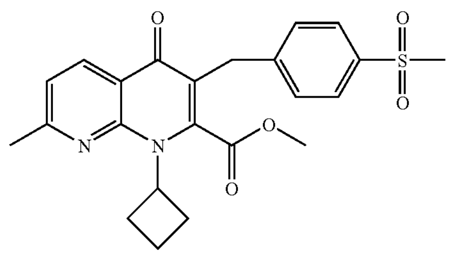 | |
| 59 | 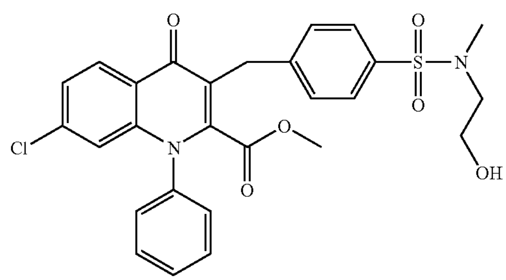 | |
| 60 | 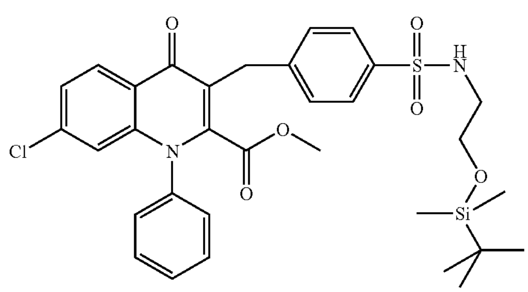 | |
| 61 | 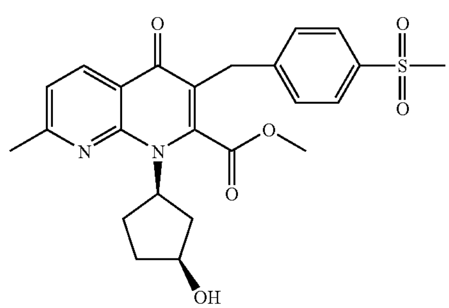 | |

TABLE 1-continued

EXEMPLARY COMPOUNDS

| Compound | Structure | Data |
|---|---|---|
| 62 | 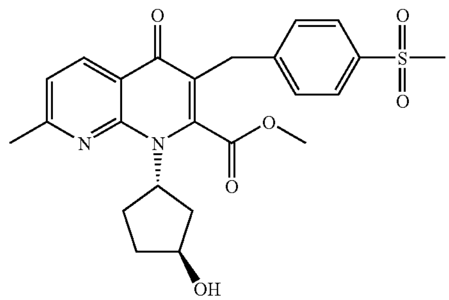 | |
| 63 | 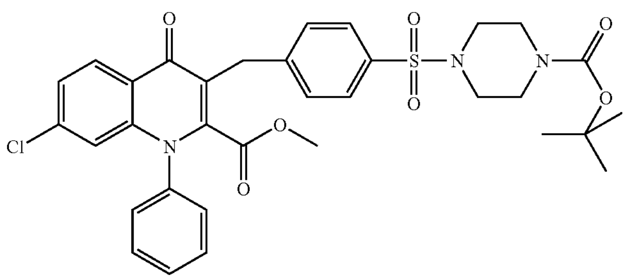 | |
| 64 | 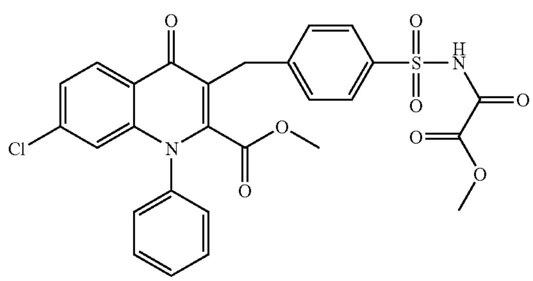 | |
| 65 | 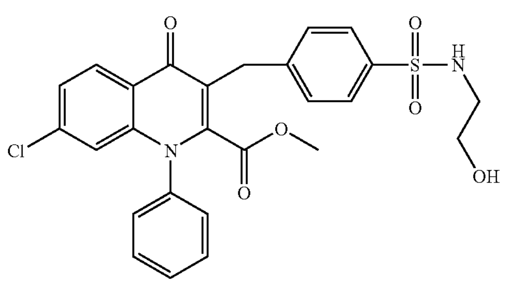 | |
| 66 | 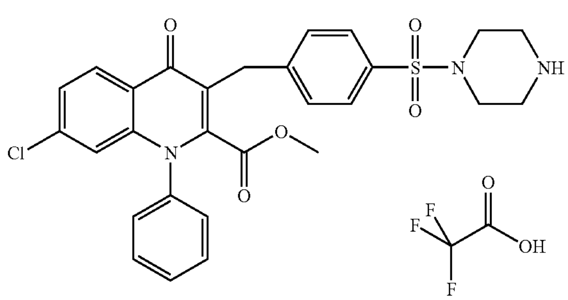 | |

TABLE 1-continued
EXEMPLARY COMPOUNDS
| Compound | Structure | Data |
|---|---|---|
| 67 | 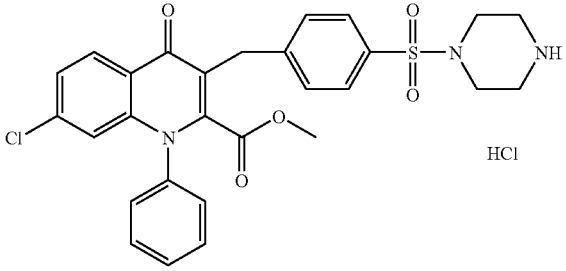 | HCl |
| 68 | 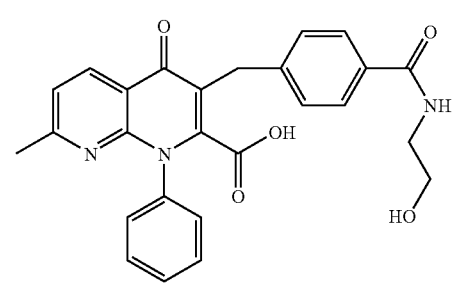 | |
| 69 | 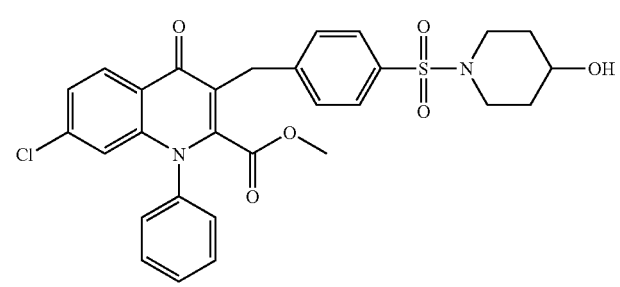 | |
| 70 | 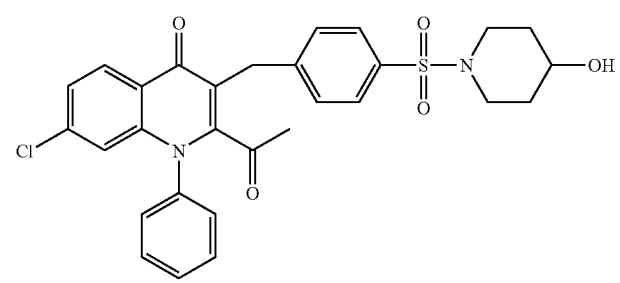 | |
| 71 | 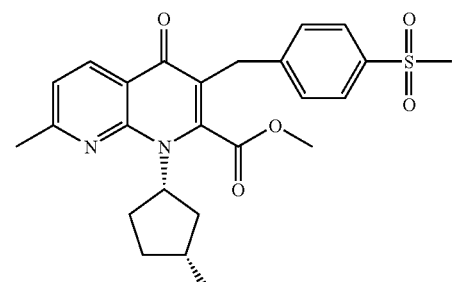 | |

TABLE 1-continued

EXEMPLARY COMPOUNDS

| Compound | Structure | Data |
|---|---|---|
| 72 | 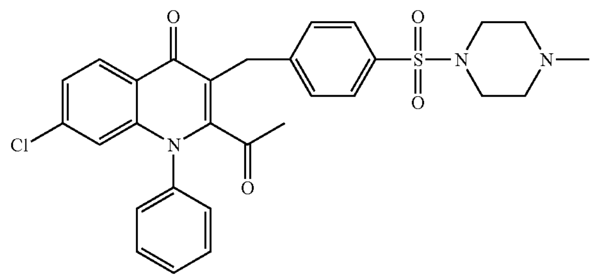 | |
| 73 | 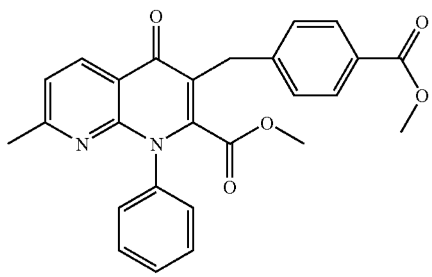 | |
| 74 | 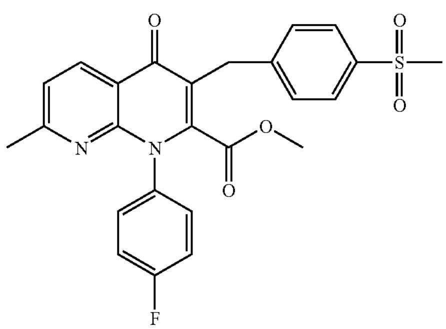 | |
| 75 | 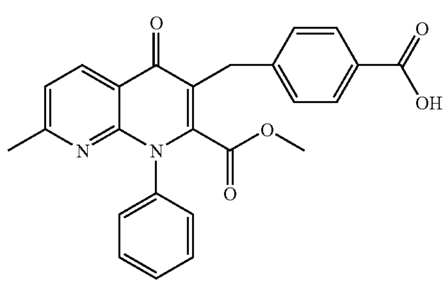 | |
| 76 | 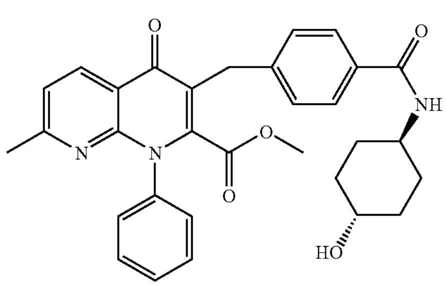 | |

TABLE 1-continued

EXEMPLARY COMPOUNDS

| Compound | Structure | Data |
|---|---|---|
| 77 | 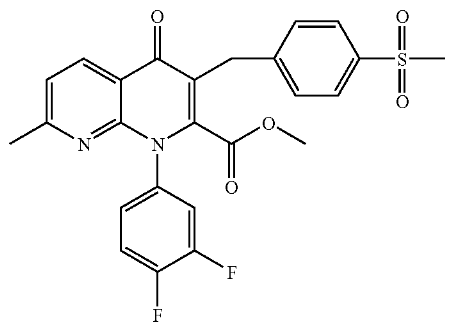 | |
| 78 | 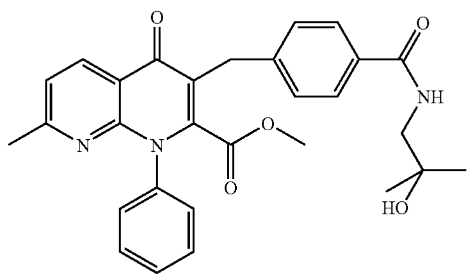 | |
| 79 | 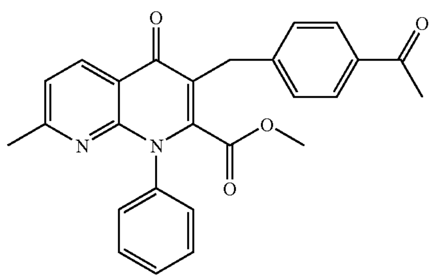 | |
| 80 | 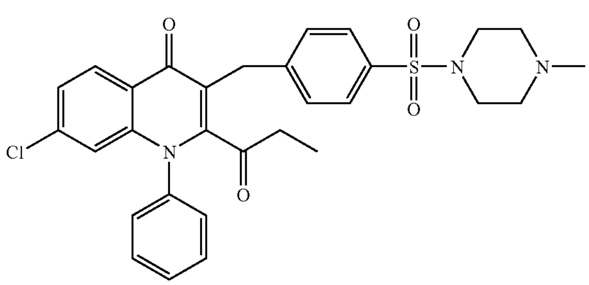 | |
| 81 | 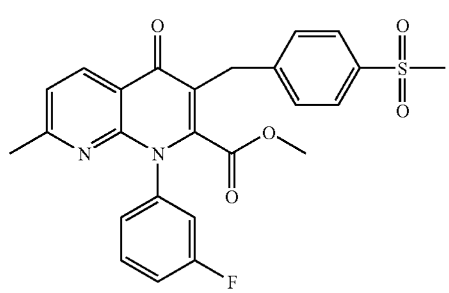 | |

TABLE 1-continued

EXEMPLARY COMPOUNDS

| Compound | Structure | Data |
|---|---|---|
| 82 | 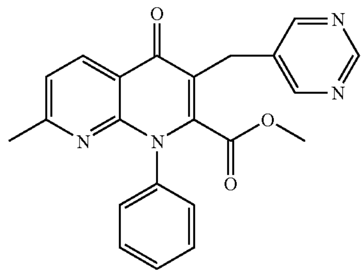 | |
| 83 | 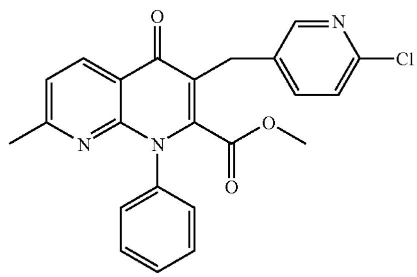 | |
| 84 | 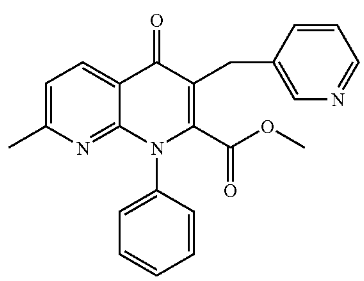 | |
| 85 | 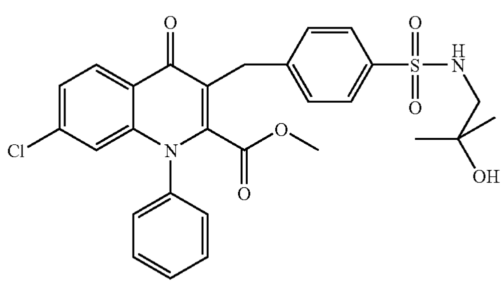 | |
| 86 | 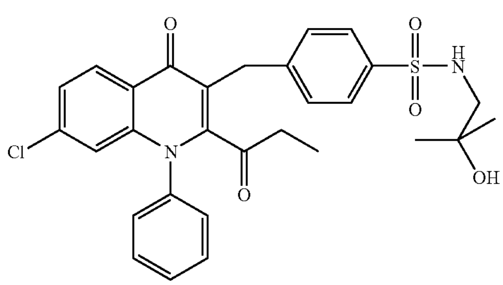 | |

TABLE 1-continued
EXEMPLARY COMPOUNDS
| Compound | Structure | Data |
|---|---|---|
| 87 | 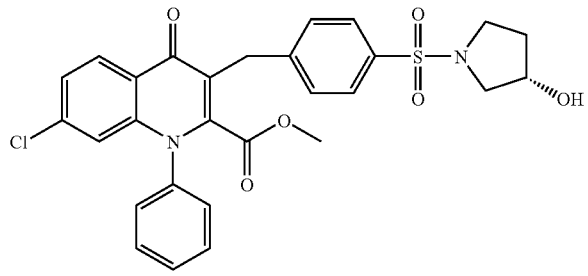 | |
| 88 | 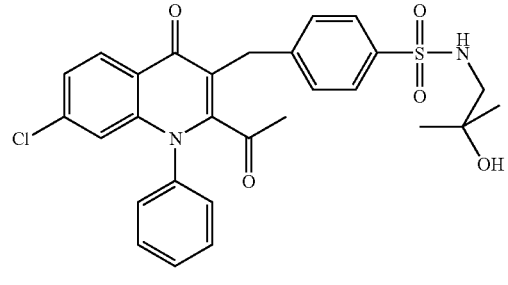 | |
| 89 | 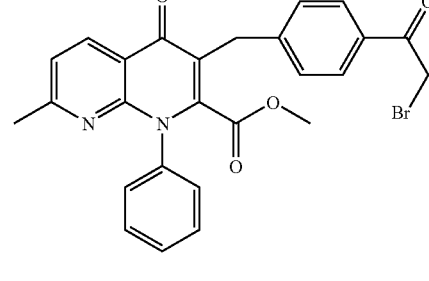 | |
| 90 | 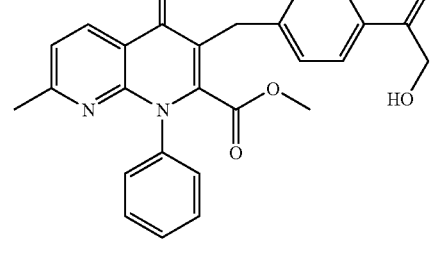 | |
| 91 | 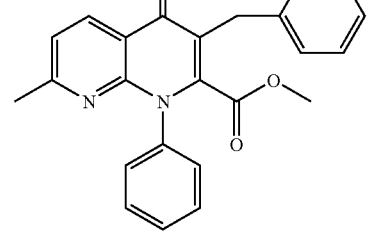 | |

TABLE 1-continued

EXEMPLARY COMPOUNDS

| Compound | Structure | Data |
|---|---|---|
| 92 | 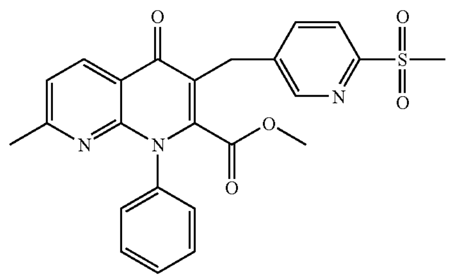 | |
| 93 | 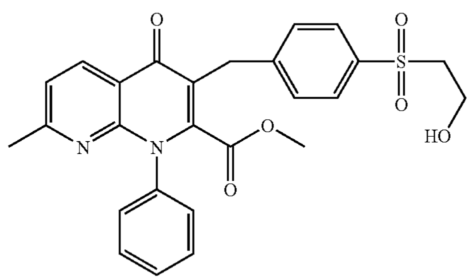 | |
| 94 | 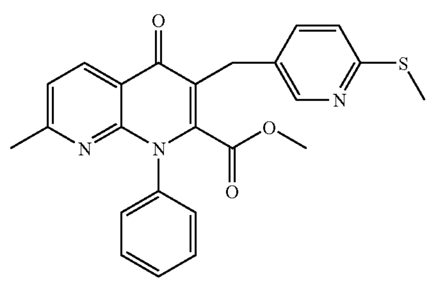 | |
| 95 | 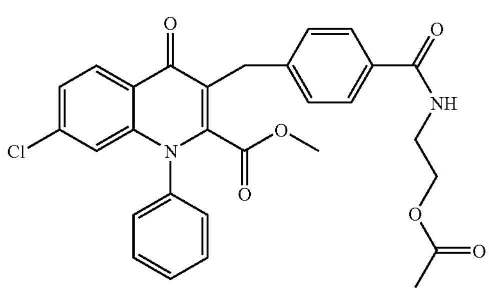 | |
| 96 | 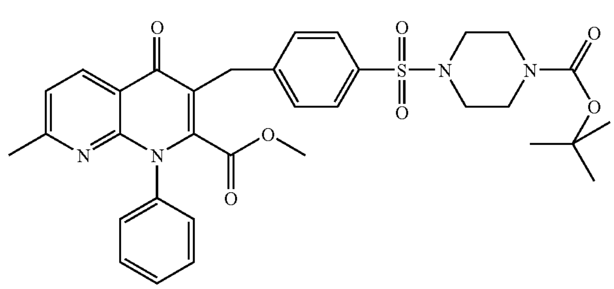 | |

TABLE 1-continued
EXEMPLARY COMPOUNDS
| Compound | Structure | Data |
|---|---|---|
| 97 | 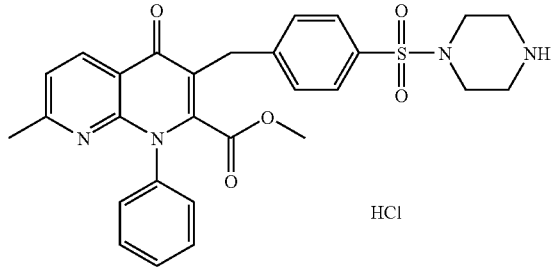 HCl | |
| 98 | 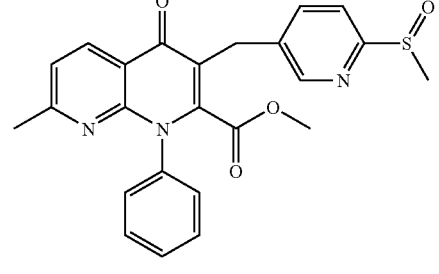 | |
| 99 | 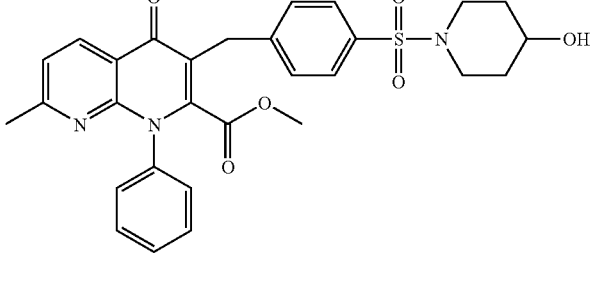 | |
| 100 | 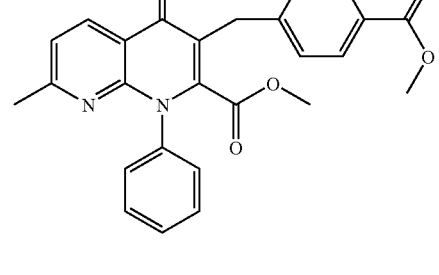 | Mp = 177-178° C. |
| 101 | 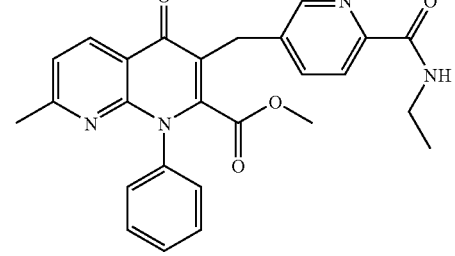 | Mp = 208-209° C. |

TABLE 1-continued

EXEMPLARY COMPOUNDS

| Compound | Structure | Data |
|---|---|---|
| 102 | 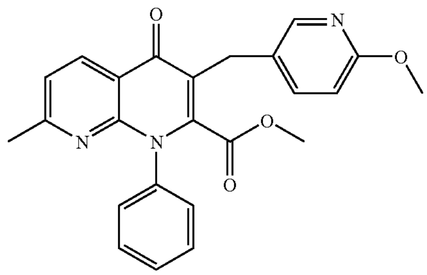 | |
| 103 | 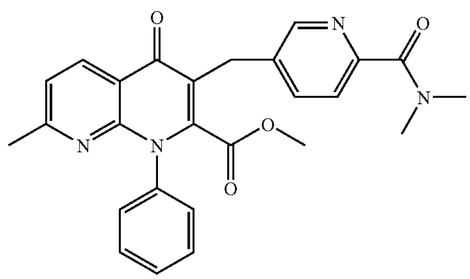 | Mp = 235-236° C. |
| 104 | 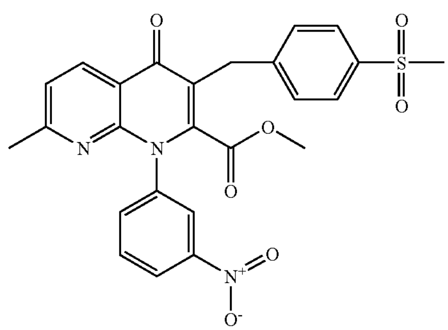 | M + H = 508 |
| 105 | 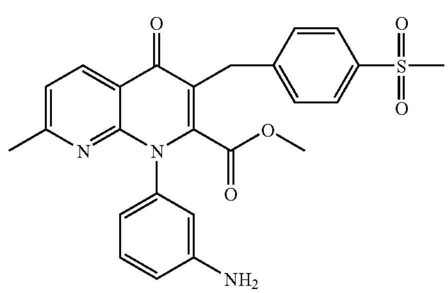 | M + H = 478 |
| 106 | 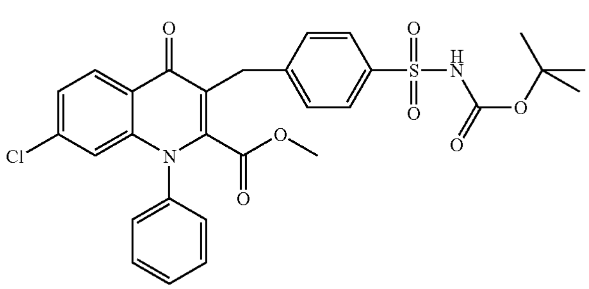 | M + H = 583 |

TABLE 1-continued

EXEMPLARY COMPOUNDS

| Compound | Structure | Data |
|---|---|---|
| 107 | 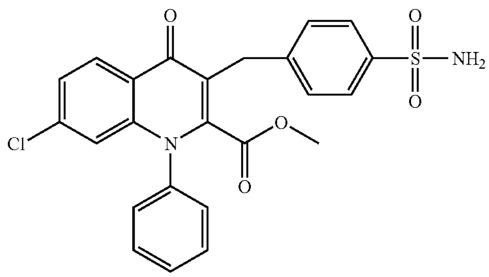 | M + H = 483 |
| 108 | 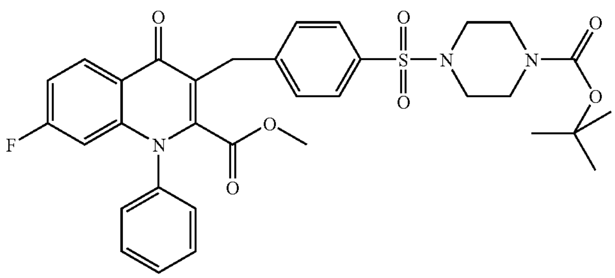 | Mp = 120-121° C.<br>M + H = 636 |
| 109 | 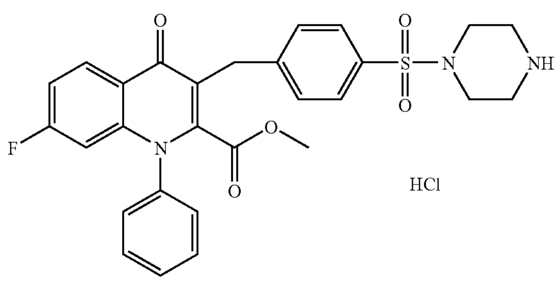 | Mp = 214-215° C.<br>M + H = 536 |
| 110 | 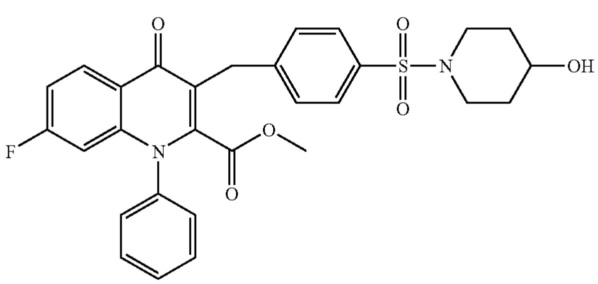 | Mp = 232-233° C.<br>M + H = 551 |
| 111 | 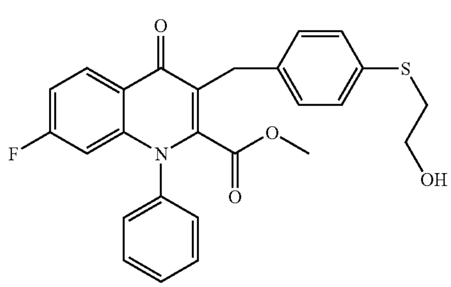 | Mp = 163-164° C.<br>M + H = 464 |

TABLE 1-continued

EXEMPLARY COMPOUNDS

| Compound | Structure | Data |
|---|---|---|
| 112 | 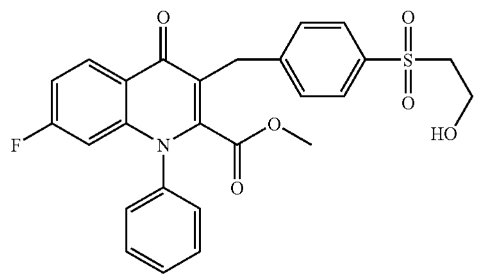 | Mp = 165-166° C.<br>M + H = 496 |
| 113 | 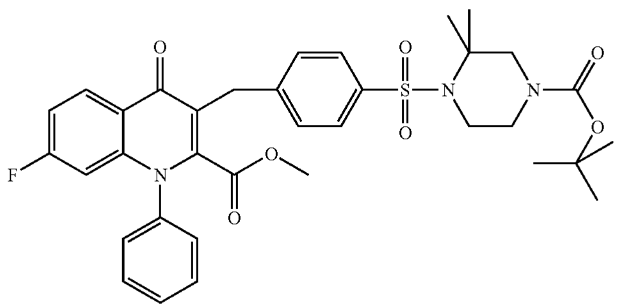 | Mp = 116-117° C.<br>M + H = 664 |
| 114 | 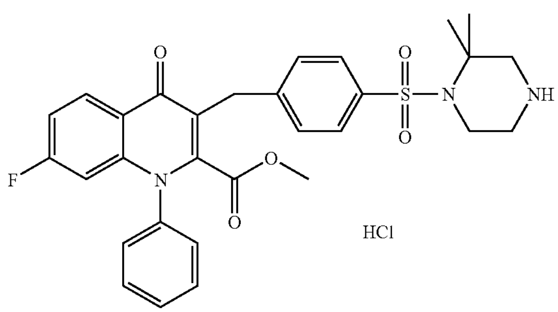 | Mp = 211-212° C.<br>M + H = 564 |
| 115 | 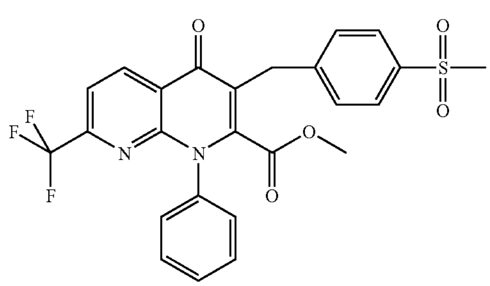 | Mp = 193-195° C.<br>M + H = 517 |
| 116 | 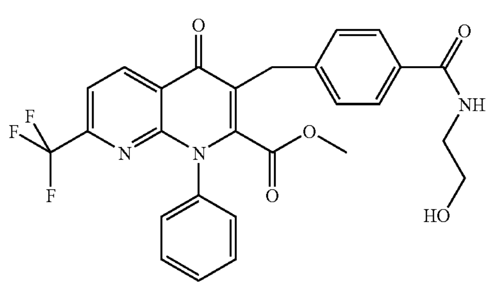 | Mp = 170-173° C.<br>M + H = 526 |

…
TABLE 1-continued
EXEMPLARY COMPOUNDS
| Compound | Structure | Data |
|---|---|---|
| 117 | 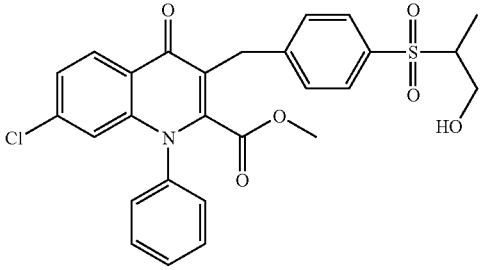 | Mp = 175.3-180.3° C.<br>M + H = 526 |
| 118 | 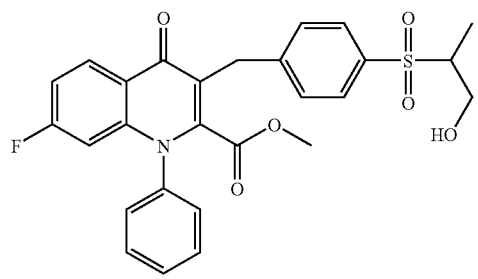 | Mp = 193.6-194.9° C.<br>M + H = 510 |
| 119 | 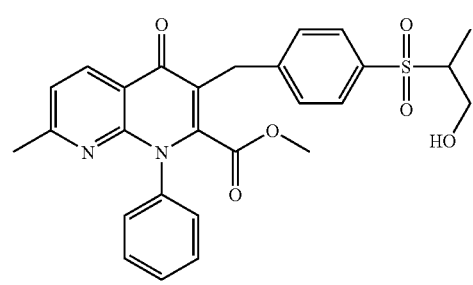 | Mp = 195.9-197.2° C.<br>M + H = 507 |
| 120 | 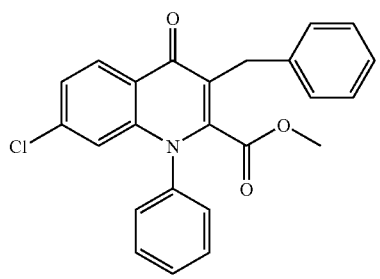 | Mp = 200.0-201.0° C. |
| 121 | 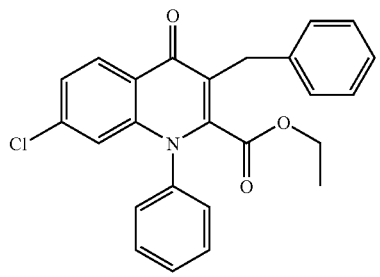 | Mp = 179.0-180.0° C. |

TABLE 1-continued

EXEMPLARY COMPOUNDS

| Compound | Structure | Data |
|---|---|---|
| 122 | 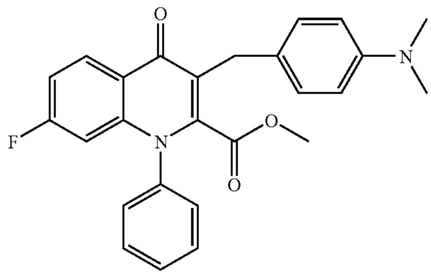 | M + H = 404 |
| 123 | 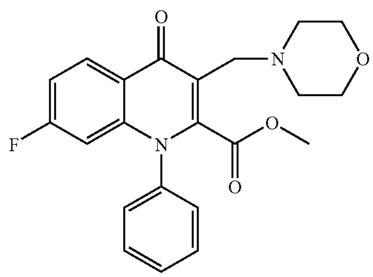 | Mp = 169.0-170.0° C.<br>M + H = 397 |
| 124 | 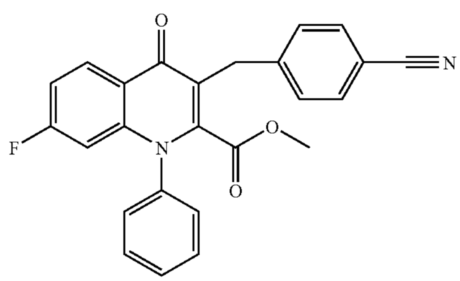 | Mp = 218.0-219.0° C.<br>M + H = 413 |
| 125 | 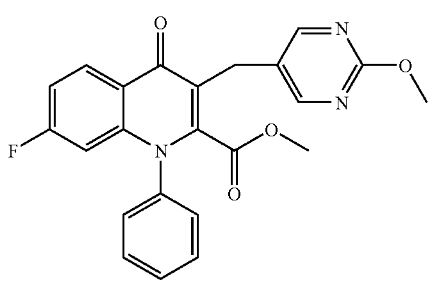 | Mp = 206.0-207.0° C.<br>M + H = 420 |
| 126 | 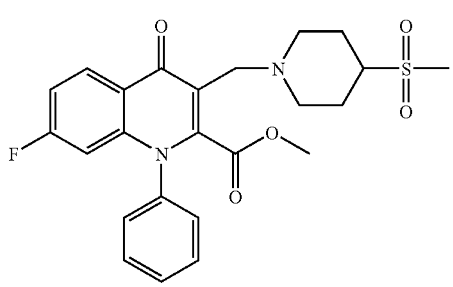 | Mp = 190.0-191.0° C.<br>M + H = 473 |

TABLE 1-continued

EXEMPLARY COMPOUNDS

| Compound | Structure | Data |
|---|---|---|
| 127 | 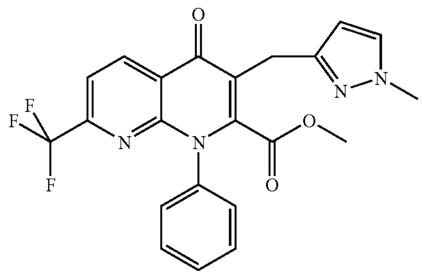 | M + H = 443 |
| 128 | 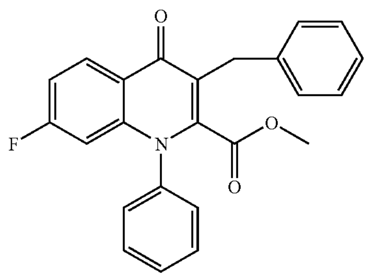 | M + H = 388 |
| 129 | 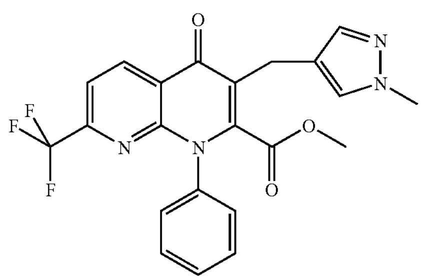 | M + H = 443 |
| 130 | 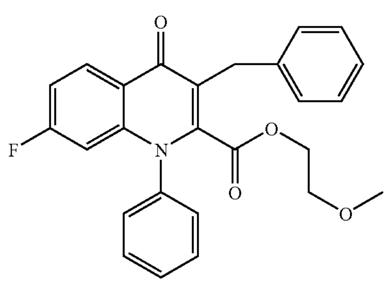 | Mp = 168.0-169.0° C.<br>M + H = 432 |
| 131 | 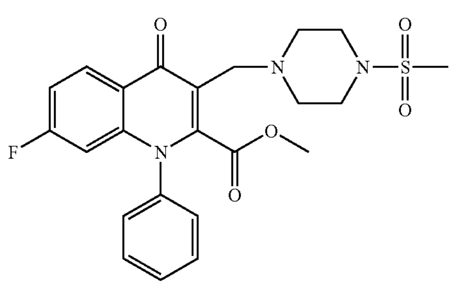 | Mp = 205.0-207.0° C.<br>M + H = 474 |

TABLE 1-continued

EXEMPLARY COMPOUNDS

| Compound | Structure | Data |
|---|---|---|
| 132 | 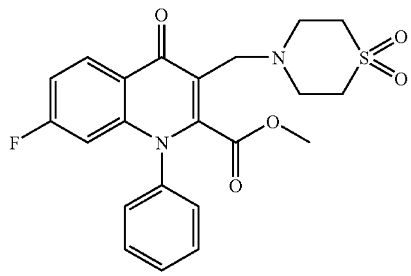 | Mp = 119.0-120.0° C.<br>M + H = 445 |
| 133 | 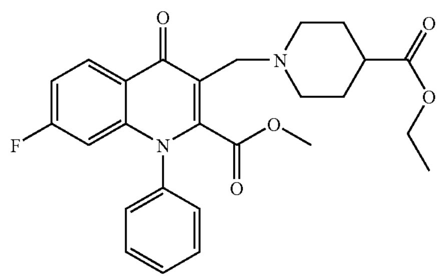 | Mp = 136.0-137.0° C.<br>M + H = 467 |
| 134 | 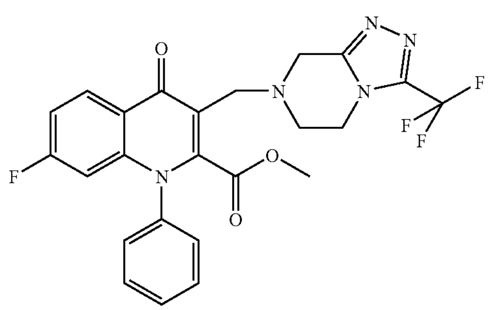 | Mp = 107.0-110.0° C.<br>M + H = 502 |
| 135 | 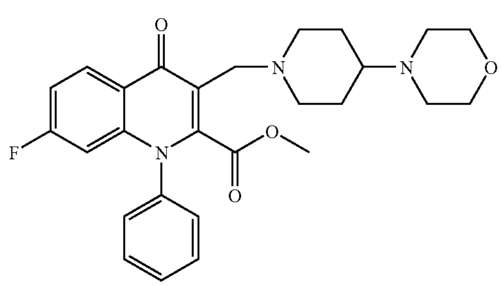 | Mp = 161.0-163.0° C.<br>M + H = 480 |
| 136 | 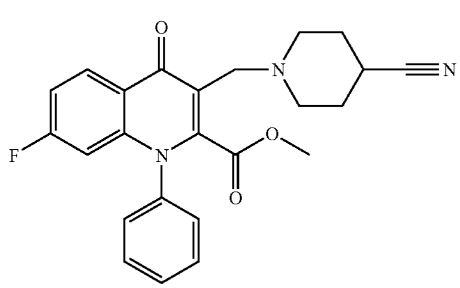 | Mp = 159.0-160.0° C.<br>M + H = 420 |

TABLE 1-continued

EXEMPLARY COMPOUNDS

| Compound | Structure | Data |
|---|---|---|
| 137 | 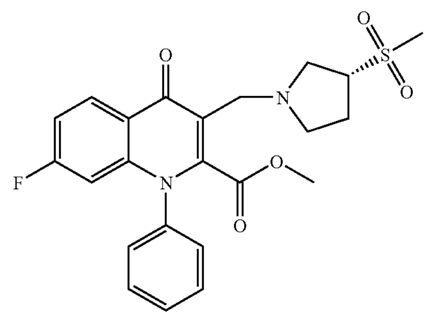 | M + H = 459 |
| 138 | 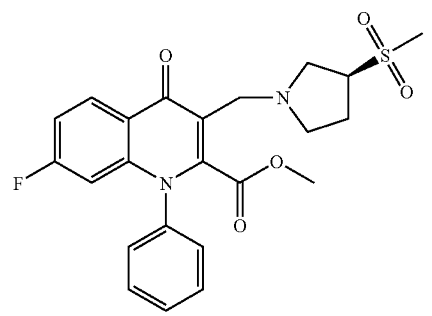 | M + H = 459 |
| 139 | 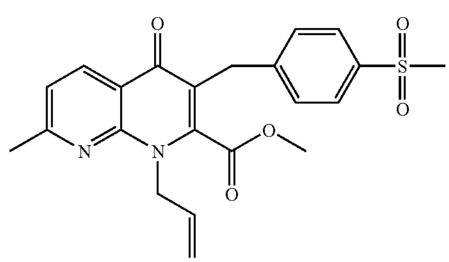 | Mp = 168.0-169.0° C. |
| 140 | 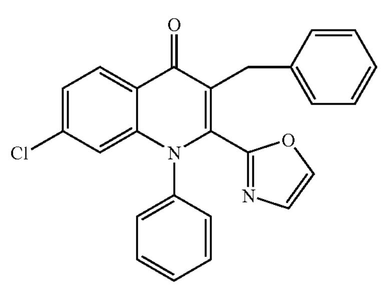 | Mp = 219.0-220.0° C. |
| 141 | 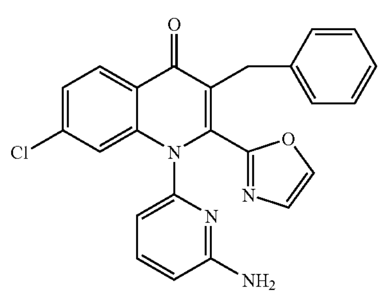 | Mp = 279.3-282.3° C. |

TABLE 1-continued

EXEMPLARY COMPOUNDS

| Compound | Structure | Data |
|---|---|---|
| 142 | 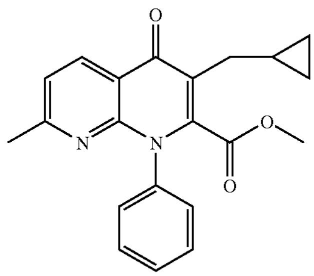 | M + H = 349 |

Utility

The compounds of this invention are JNK modulators and as such are expected to be effective in the treatment of a wide range of JNK mediated disorders. Exemplary JNK mediated disorders include, but are not limited to, autoimmune disorders, inflammatory disorders, metabolic disorders, neurological disease, and cancer. Accordingly, compounds of the invention can be used to treat one or more of such disorders. In some embodiments, compounds of the invention can be used to treat a JNK mediated disorder such as rheumatoid arthritis, asthma, type II diabetes, Alzheimer's disease, Parkinson's disease or stroke.

Administration and Pharmaceutical Compositions

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use.

Formulations containing about one (1) mg of active ingredient or, more broadly, about 0.01 to about one hundred (100) mg, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the invention may also be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described below.

Additional objects, advantages, and novel features of this invention will become apparent to those skilled in the art upon examination of the following examples thereof, which are not intended to be limiting.

EXAMPLES

The following preparations and examples are given to enable those skilled in the art to more clearly understand and to practice the present invention. They should not be consid- List of Abbreviations

| | |
|---|---|
| AcOH | Acetic acid |
| BINAP | 2,2'-bis(diphenylphosphino)-1,1'-binaphthyl |
| BOP | Benzotriazol-1-yloxytris(dimethylamino)phosphonium hexafluorophosphate |
| Bu$_2$O | Dibutyl ether |
| DCM | Dichloromethane/Methylene chloride |
| DIPEA | Diisopropylethylamine |
| DMF | N,N-dimethylformamide |
| EDCI | 1-(3-Dimethylaminopropyl)-3-ethylcarbodiimide hydrochloride |
| Et$_2$O | Diethyl ether |
| EtOH | Ethanol/Ethyl alcohol |
| EtOAc | Ethyl acetate |
| HOBt | 1-Hydroxybenzotriazole |
| MeOH | Methanol/Methyl alcohol |
| MW | Microwaves |
| NMP | 1-Methyl-2-pyrrolidinone |
| RT | Room temperature |
| NaHCO$_3$ | sodium bicarbonate |
| TEA | Triethyl amine |
| THF | Tetrahydrofuran |
| TLC | Thin layer chromatography |

Preparation 1: Synthesis of 1-(2-amino-4-chlorophenyl)-ethanone

The synthesis of 1-(2-amino-4-chlorophenyl)-ethanone was carried out according to the process shown in Scheme 1 below.

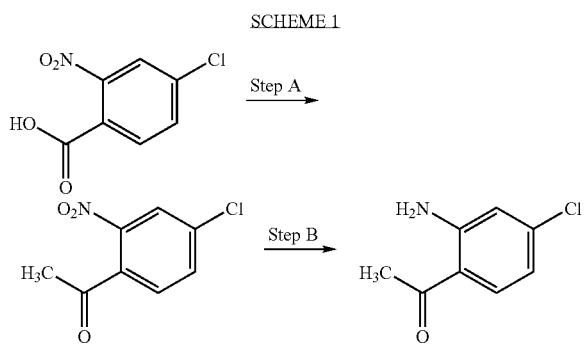

SCHEME 1

Step A: Synthesis of 1-(4-chloro-2-nitro-phenyl)-ethanone: To a solution of 4-chloro-2-nitrobenzoic acid (30.0 g, 0.15 mol) in THF (400 mL) was added oxalyl chloride (26 mL, 0.3 mol) at 0° C., followed by DMF (2 drops). After stirring for 10 min at 0° C., the ice bath was removed and the reaction mixture was heated at reflux for 3 h. The resulting mixture was then cooled and evaporated under reduced pressure. A second 1 L round bottom flask was loaded with diethyl malonate (22.8 mL, 0.15 mol) and THF (150 mL); sodium hydride (60% dispersion in mineral oil, 7.2 g, 0.18 mol) was then added at 0° C., portionwise over a period of 30 minutes. The ice bath was then removed, and the mixture was heated at reflux for 3 h. The acyl chloride, dissolved in 2 portions of THF, was added and the resulting mixture was heated at reflux for 3 h and then stirred at room temperature overnight. The reaction mixture was partitioned between water and EtOAc; the organic layer was separated and the aqueous layer was extracted twice with EtOAc. The combined organic extracts were washed with brine, dried over anhydrous sodium sulfate, filtered and evaporated under reduced pressure. A mixture of glacial AcOH (50 mL) and sulfuric acid (20% in water, 50 mL) was added to the residue, and the resulting mixture was heated at reflux for 6 h and then stirred at 80° C. overnight. The reaction mixture was basified to pH 10 by adding NaOH (aq) and then was extracted 3 times with EtOAc. The combined organic extracts were washed with brine, dried over anhydrous sodium sulfate, filtered and evaporated under reduced pressure. The crude residue was purified by flash chromatography (EtOAc/hexane) to give 7.1 g of 1-(4-chloro-2-nitro-phenyl)-ethanone.

Preparation 2: Synthesis of 4-(4-methyl-piperazine-1-sulfonyl)-benzaldehyde

The synthesis of 4-(4-methyl-piperazine-1-sulfonyl)-benzaldehyde was carried out according to the process shown in Scheme 2.

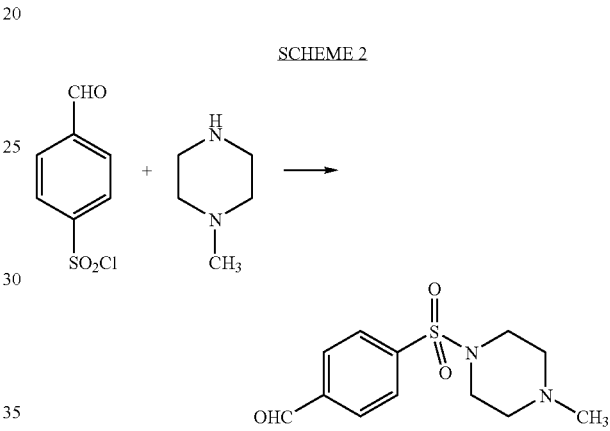

SCHEME 2

To a solution of 4-formylbenzenesulfonyl chloride (1.0 g) in DCM (10 mL) was added NaHCO$_3$ (sat'd aq, 10 mL) followed by 1-methyl-piperazine (0.6 mL). The reaction mixture was vigorously stirred for 1 h, the organic layer separated, and the aqueous layer extracted with DCM (2×20 mL). The combined organic extracts were washed with brine, dried over anhydrous Na$_2$SO$_4$, filtered and evaporated under reduced pressure to give 4-(4-methyl-piperazine-1-sulfonyl)-benzaldehyde (1.28 g) without further purification.

In the same manner, using the appropriate starting materials, the following compounds were prepared:

- N-(2,2-dimethyl-[1,3]dioxolan-4-ylmethyl)-4-formyl-benzenesulfonamide;
- 4-(Morpholine-4-sulfonyl)-benzaldehyde;
- 4-Formyl-N-methyl-benzenesulfonamide;
- 4-Formyl-N,N-dimethylbenzenesulfonamide;
- 4-Formyl-N-(2-hydroxy-ethyl)-N-methyl-benzenesulfonamide; and
- N-[2-(tert-Butyl-dimethyl-silanyloxy)-ethyl]-4-formyl-benzenesulfonamide (for the amine synthesis see Bioorg. & Med. Chem. (2005) 13(11):3801-39); and
- 4-(4-Formyl-benzenesulfonyl)-piperazine-1-carboxylic acid tert-butyl ester;

Preparation 3: Synthesis of 1-(4-chloro-2-phenylamino-phenyl)-ethanone

The synthesis of 1-(4-chloro-2-phenylamino-phenyl)-ethanone was carried out according to the process shown in Scheme 3.

SCHEME 3

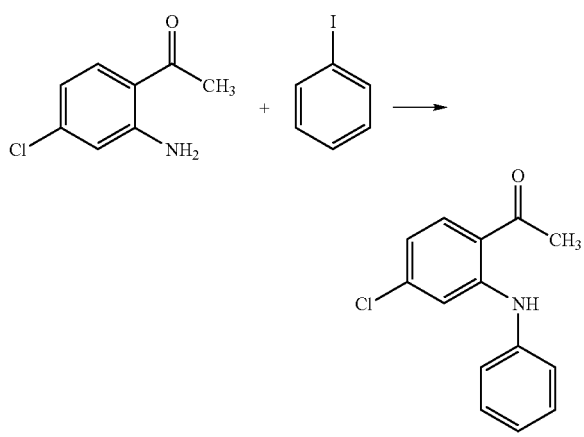

A mixture of 1-(2-amino-4-chlorophenyl)-ethanone (1.85 g), copper powder (140 mg), KI (360 mg), K$_2$CO$_3$ (3.06 g) and iodobenzene (4.8 mL) in dibutyl ether (40 mL) was heated at 160° C. (oil bath temperature) overnight. More copper powder (140 mg), KI (360 mg), K$_2$CO$_3$ (3.06 g) and iodobenzene (4.8 mL) were added and the reaction mixture was heated at reflux overnight. The resulting mixture was then cooled and concentrated under reduced pressure. The residue was partitioned between water and ethyl acetate, the organic layer was separated and the aqueous layer was extracted with ethyl acetate (2×50 mL). The combined organic extracts were washed with brine, dried over anhydrous sodium sulfate, filtered and evaporated under reduced pressure. The crude residue was purified by flash chromatography (EtOAc/hexane) to afford 2.2 g of 1-(4-chloro-2-phenylamino-phenyl)-ethanone.

Following the above described procedure and the appropriate starting materials, the following compounds were prepared:

1-(2-Phenylamino-phenyl)-ethanone;
1-(4-Methoxy-2-phenylamino-phenyl)-ethanone;
1-(5-Chloro-2-phenylamino-phenyl)-ethanone;
1-(5-Methoxy-2-phenylamino-phenyl)-ethanone;
1-(2-Phenylamino-pyridin-3-yl)-ethanone; MS=213 [M+H]$^+$; and
1-(6-Methyl-2-phenylamino-pyridin-3-yl)-ethanone.

Preparation 4: Synthesis of
4-(2-hydroxy-ethylsulfanyl)-benzaldehyde

The synthesis of 4-(2-hydroxy-ethylsulfanyl)-benzaldehyde was carried out according to the process shown in Scheme 4.

SCHEME 4

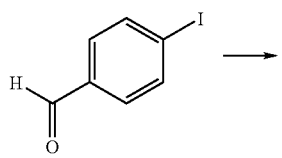

-continued

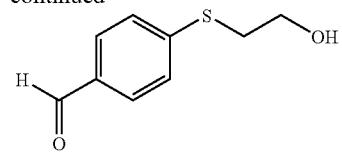

To a mixture of 4-iodobenzaldehyde (1.0 g) and copper (0) powder (2.34 g) was added DMF (10 mL), and the resulting mixture was heated at 140° C. under argon for 3 h. 2-hydroxyethyl disulfide (0.82 mL) was added, and the resulting mixture was stirred at 140° C. overnight under argon. The reaction mixture was cooled and filtered through glass-fiber filter paper. The filtrate was evaporated under high vacuum and the residue purified by flash chromatography (EtOAc/hexane) to provide 4-(2-hydroxy-ethylsulfanyl)-benzaldehyde (0.784 g, quantitative yield).

Preparation 5: Synthesis of
3-Amino-3,N,N-trimethyl-butyramide

The synthesis of 3-Amino-3,N,N-trimethyl-butyramide was carried out according to the process shown in Scheme 5.

SCHEME 5

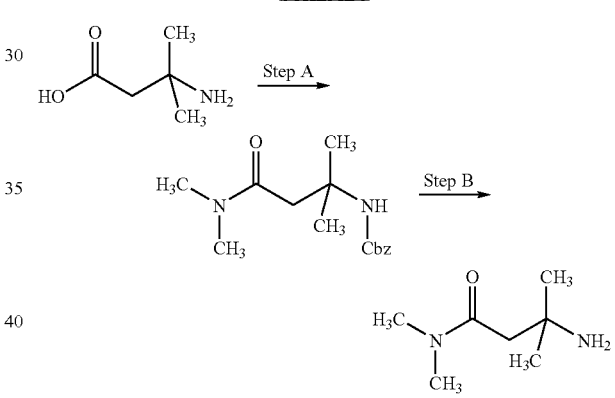

Step A: Synthesis of 3-benzyloxycarbonylamino-3-methyl-butyric acid. 3-Amino-3-methylbutyric acid (2.40 g, 20.49 mmol) was dissolved in NaOH (2 M aq, 35 mL), the resulting mixture cooled to 0° C., and benzyl chloroformate (5.77 mL, 40.97 mmol) added. The reaction mixture was stirred vigorously at 0° C. for 1 h and at RT for 3 h. Et$_2$O (50 mL) was then added, and the layers separated. The organic layer was discarded. The aqueous layer was acidified to pH 2, brine added, and the resulting mixture extracted with EtOAc. The combined organic extracts were dried over anhydrous Na$_2$SO$_4$, filtered and evaporated under reduced pressure to give 3-benzyloxycarbonylamino-3-methyl-butyric acid (2.33 g, 46% yield) without further purification.

Step B: Synthesis of (2-dimethylcarbamoyl-1,1-dimethylethyl)-carbamic acid benzyl ester. HOBt (1.242 g, 9.193 mmol) and EDCI (2.35 g, 12.26 mmol) were added to a solution of 3-benzyloxycarbonylamino-3-methyl-butyric acid (1.54 g, 6.129 mmol) in DCM (45 mL) at 0° C. The resulting mixture was stirred at 0° C. for 30 min, and a solution of Me$_2$NH (2 M in THF, 12.26 mL, 24.51 mmol) was added. The reaction mixture was warmed up to RT and stirred overnight. The solvent was evaporated under reduced pressure, and the residue partitioned between EtOAc and a mixture of water, brine and NaHCO₃ (sat aq). The organic layer was separated, washed with HCl (1 M), dried over anhydrous MgSO₄, filtered and evaporated under reduced pressure. The crude residue was purified by flash chromatography (EtOAc/hexane) to afford (2-dimethylcarbamoyl-1,1-dimethylethyl)-carbamic acid benzyl ester (1.14 g, 67% yield).

Step C: Synthesis of 3-amino-3,N,N-trimethyl-butyramide. A mixture of (2-dimethyl-carbamoyl-1,1-dimethylethyl)-carbamic acid benzyl ester (1.14 g) and Pd/C (10%, 114 mg) was stirred under H₂ (balloon pressure) for 18 h at RT. The reaction mixture was filtered through a CELITE™ pad, and the filtrate evaporated under reduced pressure to give 3-amino-3,N,N-tri-methyl-butyramide (366 mg, 62% yield).

Preparation 6: Synthesis of 1-[2-((1R,2R)-2-Hydroxy-cyclopentylamino)-6-methyl-pyridin-3-yl]-ethanone The synthesis of 1-[2-((1R,2R)-2-hydroxy-cyclopentylamino)-6-methyl-pyridin-3-yl]-ethanone was carried out according to the process shown in Scheme 6.

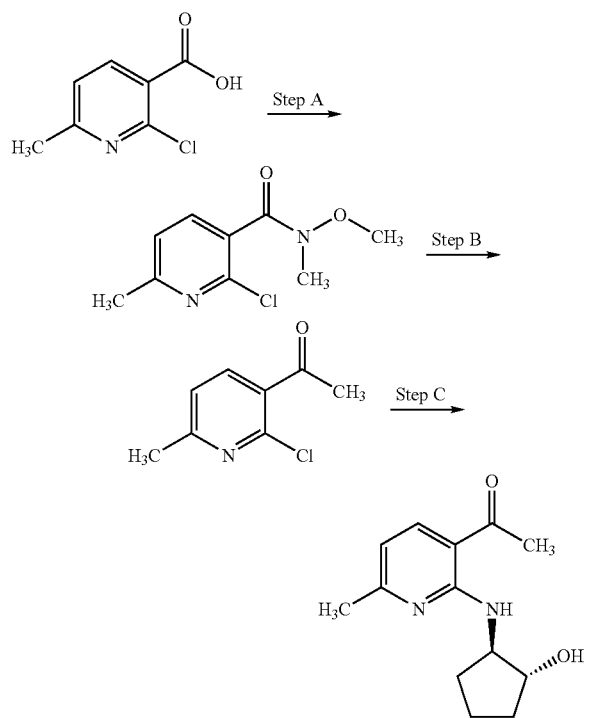

SCHEME 6

Step A: Synthesis of 2-chloro-N-methoxy-6,N-dimethyl-nicotinamide. A mixture of 2-chloro-6-methyl-nicotinic acid (2 g, 12 mmol), N,O-dimethylhydroxylamine hydrochloride (1.14 g, 12 mmol), EDCI (2.68 g, 14 mmol), HOBt (81 mg, 16 mmol) and DIPEA (1 mL) in DCM (100 mL) was stirred at RT overnight. The reaction mixture was then partitioned between water and DCM, the organic layer separated, dried over anhydrous Na₂SO₄, filtered, and evaporated under reduced pressure. The crude residue was purified by flash chromatography (EtOAc/hexane, gradient from 0 to 25% in 25 minutes) to afford 2.4 g of 2-chloro-N-methoxy-6,N-dimethyl-nicotinamide as a white solid.

Step B: Synthesis of 1-(2-chloro-6-methyl-pyridin-3-yl)-ethanone. A solution of methyl magnesium chloride (3 M in THF, 10 mL) was slowly added at 0° C. to a solution of 2-chloro-N-methoxy-6,N-dimethyl-nicotinamide (2.4 g) in THF (100 mL). The reaction mixture was stirred at 0° C. for 1 h, then quenched with water. The resulting mixture was extracted with EtOAc, the combined organics dried over anhydrous Na₂SO₄, filtered and evaporated under reduced pressure. The crude residue was purified by flash chromatography (EtOAc/hexane, gradient from 0 to 25% in 25 minutes) to give 1-(2-chloro-6-methylpyridin-3-yl)-ethanone (0.85 g) as a brown oil.

Step C: Synthesis of 1-[2-((1R,2R)-2-hydroxy-cyclopentylamino)-6-methyl-pyridin-3-yl]-ethanone. (1R,2R)-2-Amino-cyclopentanol HCl salt (1.0 g) was treated with K₂CO₃ (sat aq) and the mixture extracted 3× with EtOAc. The combined organic extracts were dried over anhydrous Na₂SO₄, filtered, and evaporated under reduced pressure. The product was combined with 1-(2-chloro-6-methyl-pyridin-3-yl)-ethanone (0.4 g) and 1-methyl-2-pyrrolidinone (1 mL), and the mixture heated to 180° C. in a microwave reactor for 2 h. The reaction mixture was then partitioned between water and EtOAc, the organic layer separated and washed 3× with water, dried over anhydrous Na₂SO₄, filtered, and evaporated under reduced pressure. The crude residue was purified by flash chromatography (EtOAc/hexane, gradient from 0 to 25% in 20 min) to give 1-[2-((1R,2R)-2-hydroxy-cyclopentylamino)-6-methylpyridin-3-yl]-ethanone (507 mg, 92% yield). MS=235 [M+H]⁺.

Using the above described procedure and the appropriate starting materials the following compounds were prepared:

1-[2-(3-Hydroxy-cyclohexylamino)-6-methyl-pyridin-3-yl]-ethanone;

1-(2-Cyclopentylamino-6-methyl-pyridin-3-yl)-ethanone;

1-[6-Methyl-2-(tetrahydro-pyran-4-ylamino)-pyridin-3-yl]-ethanone;

1-[2-((1R,3R)-3-Hydroxy-cyclopentylamino)-6-methyl-pyridin-3-yl]-ethanone (using (1R,3R)-3-amino-cyclopentanol commercially available from AFID Therapeutics);

1-(2-Isopropylamino-6-methyl-pyridin-3-yl)-ethanone;

1-[2-(1,1-Dioxo-tetrahydro-1λ⁶-thiophen-3-ylamino)-6-methyl-pyridin-3-yl]-ethanone;

1-(2-Cyclopropylamino-6-methyl-pyridin-3-yl)-ethanone;

1-[2-(2-Methoxy-1-methylethylamino)-6-methylpyridin-3-yl]-ethanone;

1-(2-Methylaminophenyl)-ethanone;

1-(2-Cyclobutylamino-6-methyl-pyridin-3-yl)-ethanone;

1-[2-((1R,3S)-3-Hydroxy-cyclopentylamino)-6-methyl-pyridin-3-yl]-ethanone;

1-[2-((1S,3S)-3-Hydroxy-cyclopentylamino)-6-methyl-pyridin-3-yl]-ethanone; and

1-[2-((1R,3R)-3-Hydroxymethyl-cyclopentylamino)-6-methyl-pyridin-3-yl]-ethanone.

Preparation 7: Synthesis of 4-Formyl-benzenesulfonamide

The synthesis of 4-formyl-benzenesulfonamide was carried out according to the process shown in Scheme 7.

SCHEME 7

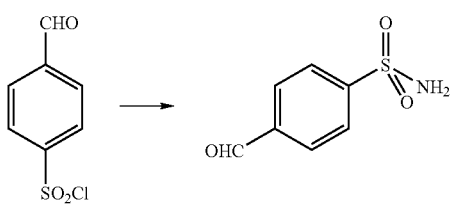

A solution of ammonia (0.5 M in 1,4-dioxane, 5 mL) was added to 4-formylbenzenesulfonyl chloride (0.5 g), followed by DCM (10 mL). The reaction mixture was stirred vigorously for 3 h at RT, then concentrated under reduced pressure. The crude residue was purified by flash chromatography to afford 4-formyl-benzenesulfonamide. MS=183.9 [M–H]⁻.

Example 1

Synthesis of 7-Chloro-3-[4-(4-methylpiperazine-1-sulfonyl)-benzyl]-4-oxo-1-phenyl-1,4-dihydroquinoline-2-carboxylic acid methyl ester The synthesis of 7-chloro-3-[4-(4-methyl-piperazine-1-sulfonyl)-benzyl]-4-oxo-1-phenyl-1,4-dihydroquinoline-2-carboxylic acid methyl ester (compound 30) was carried out according to the process shown in Scheme 8:

SCHEME 8

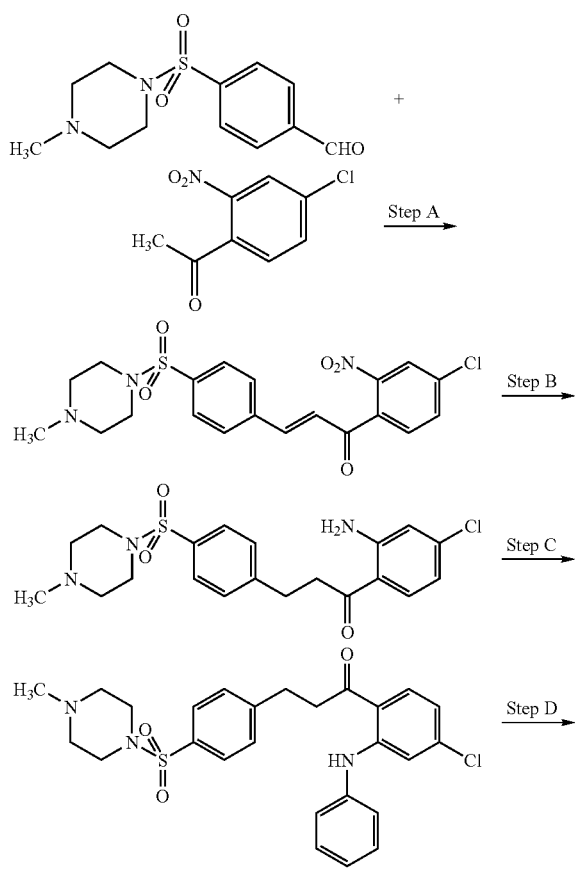

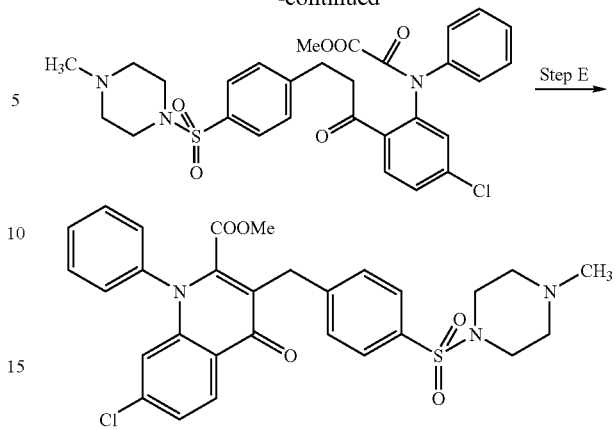

Step A: To a solution of 4-(4-methylpiperazine-1-sulfonyl) benzaldehyde (1.23 g) and 1-(4-chloro-2-nitrophenyl)ethanone (0.938 g) in MeOH (50 mL) was added NaOH (2 M aq, 4.3 mL), and the resulting mixture stirred for 15 min. The light brown solid which crashed out of solution was collected by filtration and washed with water. The solid material was taken up in MeOH, and the mixture evaporated under reduced pressure to azeotropically remove residual water. The solid residue was dried under reduced pressure to give (E)-1-(4-chloro-2-nitro-phenyl)-3-[4-(4-methylpiperazine-1-sulfonyl)phenyl]propenone (1.20 g) without further purification.

Step B: A mixture of (E)-1-(4-chloro-2-nitrophenyl)-3-[4-(4-methylpiperazine-1-sulfonyl)-phenyl]-propenone (1.167 g) and platinum (IV) oxide (50 mg) in a mixture of EtOH and THF (10/1, 110 mL) was stirred under H₂ (balloon pressure) overnight. The reaction mixture was then filtered, and the filtrate was evaporated under reduced pressure to afford 1-(2-amino-4-chlorophenyl)-3-[4-(4-methylpiperazine-1-sulfonyl)-phenyl]-propan-1-one (1.28 g) as a yellow solid.

Step C: A mixture of 1-(2-amino-4-chlorophenyl)-3-[4-(4-methylpiperazine-1-sulfonyl)-phenyl]-propan-1-one (1.268 g), copper powder (38 mg), KI (99 mg), K₂CO₃ (829 mg) and iodobenzene (1.35 mL) in dibutyl ether (25 mL) was heated to 160° C. (oil bath temperature) overnight. Additional copper powder (38 mg), KI (99 mg), K₂CO₃ (829 mg) and iodobenzene (1.35 mL) were added, and the resulting mixture was again stirred at 160° C. overnight. The reaction mixture was then cooled and concentrated under reduced pressure. The residue was partitioned between water and EtOAc, the organic layer was separated, and the aqueous layer was extracted 2× with EtOAc (50 mL). The combined organic extracts were washed with brine, dried over anhydrous Na₂SO₄, filtered, and evaporated under reduced pressure. The crude residue was purified by flash chromatography (DCM/MeOH, 100/0 for 5 minutes, 98/2 from minute 8 to 20) to give 1-(4-chloro-2-phenylaminophenyl)-3-[4-(4-methylpiperazine-1-sulfonyl)-phenyl]-propan-1-one (1.02 g; 68% yield). MS=498.0 [M+H]⁺.

Step D: Methyl oxalyl chloride (1.6 mL) was added to a solution of 1-(4-chloro-2-phenylamino-phenyl)-3-[4-(4-methylpiperazine-1-sulfonyl)-phenyl]-propan-1-one (0.563 g, 1.1 mmol) in toluene (40 mL). The reaction mixture was heated to reflux overnight, then evaporated under reduced pressure to give N-(5-chloro-2-{3-[4-(4-methylpiperazine-1-sulfonyl)-phenyl]-propionyl}-phenyl)-N-phenyl-oxalamic acid methyl ester without further purification.

Step E: A mixture of N-(5-chloro-2-{3-[4-(4-methylpiperazine-1-sulfonyl)-phenyl]-propionyl}-phenyl)-N-phenyloxalamic acid methyl ester (1.1 mmol) and K₂CO₃ (282 mg) in MeOH (60 mL) was heated at reflux for 1 h. The reaction mixture was then cooled and evaporated under reduced pressure. The residue was partitioned between water and EtOAc, the organic layer separated, and the aqueous layer extracted with EtOAc (2×25 mL). The combined organic extracts were washed with brine, dried over anhydrous Na₂SO₄, filtered, and evaporated under reduced pressure to give an orange-brown oil. The crude residue was purified twice by flash chromatography (DCM/MeOH) to give 7-chloro-3-[4-(4-methyl-piperazine-1-sulfonyl)-benzyl]-4-oxo-1-phenyl-1,4-dihydroquinoline-2-carboxylic acid methyl ester as light brown solid. MS=566 [M+H]⁺; MP=223.3-226.6° C.

Using the procedure described above, substituting appropriate starting materials, the following compounds were prepared:

7-Chloro-3-[4-(morpholine-4-sulfonyl)-benzyl]-4-oxo-1-phenyl-1,4-dihydroquinoline-2-carboxylic acid methyl ester (off-white powder), MS=553.0 [M+H]⁺; MP=237.9-238.8° C. (compound 31); and 7-Chloro-3-(4-dimethylsulfamoyl-benzyl)-4-oxo-1-phenyl-1,4-dihydroquinoline-2-carboxylic acid methyl ester (light brown powder) (compound 32), MS=511.0 [M+H]⁺; MP=218.1-219.5° C.

Example 2

Synthesis of 7-chloro-3-[4-(2,3-dihydroxy-propyl-sulfamoyl)-benzyl]-4-oxo-1-phenyl-1,4-dihydro-quinoline-2-carboxylic acid methyl ester The synthesis of 7-chloro-3-[4-(2,3-dihydroxy-propylsulfamoyl)-benzyl]-4-oxo-1-phenyl-1,4-dihydroquinoline-2-carboxylic acid methyl ester (compound 46) was carried out according to the process shown in Scheme 9.

SCHEME 9

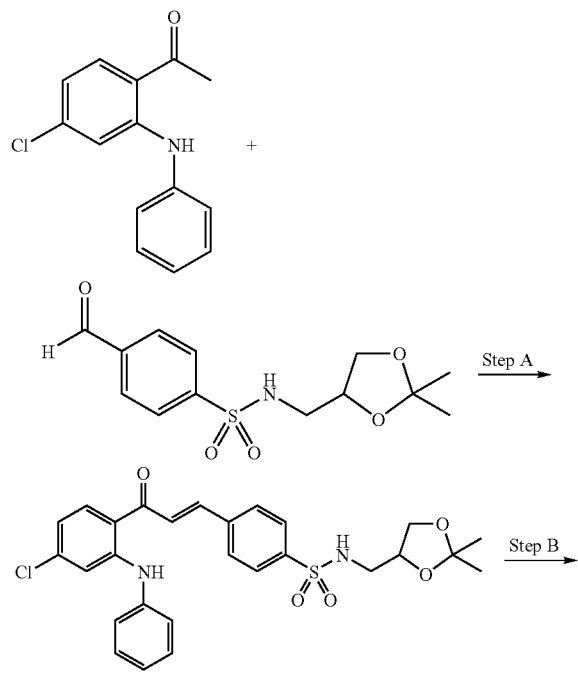

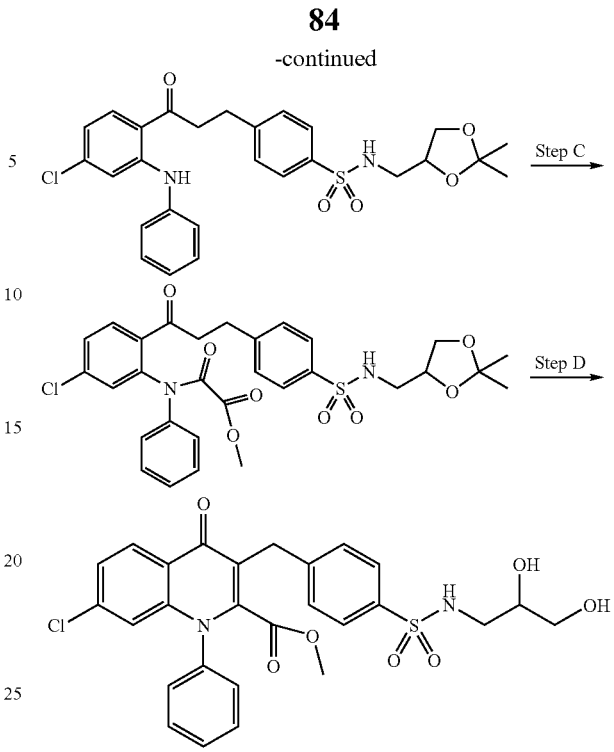

Step A: NaOH (2 M aq, 0.91 mL, 1.8 mmol) was added to a solution of N-(2,2-dimethyl-[1,3]dioxolan-4-ylmethyl)-4-formyl-benzenesulfonamide (305 mg, 1 mmol) and 1-(4-chloro-2-phenylamino-phenyl)-ethanone (250 mg, 1 mmol) in MeOH (10 mL), and the resulting mixture stirred at RT overnight. A second aliquot of NaOH (2 M aq, 0.1 mL) was added, and the reaction mixture was again stirred at RT overnight. The resulting mixture was evaporated under reduced pressure, and the crude residue partitioned between water and EtOAc. The organic layer was separated, and the aqueous layer was extracted twice with EtOAc. The combined organic extracts were washed with brine, dried over anhydrous Na₂SO₄, filtered and evaporated under reduced pressure to give an oil. The crude residue was purified twice by flash chromatography (EtOAc/hexane) to give 4-[(E)-3-(4-chloro-2-phenylamino-phenyl)-3-oxo-propenyl]-N-(2,2-dimethyl [1,3]dioxolan-4-ylmethyl)-benzenesulfonamide (70 mg).

Step B: Platinum (IV) oxide (50 mg) was added to 4-[(E)-3-(4-chloro-2-phenylamino-phenyl)-3-oxopropenyl]-N-(2,2-dimethyl-[1,3]dioxolan-4-ylmethyl)-benzenesulfonamide (66 mg) in a mixture of EtOH and EtOAc (1:1, 50 mL) and the resulting mixture was stirred under H₂ (balloon pressure) for 1.5 h. The reaction mixture was then filtered through glass-fiber paper on a Büchner funnel. The filtrate was evaporated under reduced pressure to afford 52 mg of a 2:1 mixture (by NMR) of the unprotected diol: 4-[3-(4-chloro-2-phenylaminophenyl)-3-oxopropyl]-N-(2,3-dihydroxypropyl)-benzenesulfonamide, and the protected compound-4-[3-(4-chloro-2-phenylaminophenyl)-3-oxopropyl]-N-(2,2-dimethyl-[1,3]dioxolan-4-ylmethyl)-benzenesulfonamide.

Step C: Methyl oxalyl chloride (80 µL) was added to a 2:1 mixture of 4-[3-(4-chloro-2-phenylaminophenyl)-3-oxopropyl]-N-(2,3-dihydroxypropyl)-benzenesulfonamide and 4-[3-(4-chloro-2-phenylamino-phenyl)-3-oxo-propyl]-N-(2,2-dimethyl-[1,3]dioxolan-4-ylmethyl)-benzenesulfonamide (25 mg) in toluene (5 mL), and the resulting mixture heated to 120° C. for 1.5 h. The reaction mixture was evaporated under reduced pressure to give N-(5-chloro-2-{3-[4-(2,3-dihydroxy-propylsulfamoyl)-phenyl]-propionyl}-phenyl)-N-phenyl-oxalamic acid methyl ester and the protected compound, N-(5-chloro-2-{3-[4-(2,2-dimethyl-[1,3]dioxolan-4-ylmethylsulfamoyl)-phenyl]-propionyl}-phenyl)-N-phenyl-oxalamic acid methyl ester, which was used without further purification.

Step D: $K_2CO_3$ (12 mg) was added the mixture of N-(5-chloro-2-{3-[4-(2,3-dihydroxy-propylsulfamoyl)-phenyl]-propionyl}-phenyl)-N-phenyl-oxalamic acid methyl ester and N-(5-chloro-2-{3-[4-(2,2-dimethyl-[1,3]dioxolan-4-yl-methylsulfamoyl)-phenyl]-propionyl}-phenyl)-N-phenyl-oxalamic acid methyl ester (0.05 mmol) in MeOH (5 mL), and the resulting mixture stirred at 80° C. for 1.5 h. The reaction mixture was then cooled and evaporated under reduced pressure. The residue was partitioned between water and EtOAc, the organic layer separated, and the aqueous layer extracted with EtOAc (2×25 mL). The combined organic extracts were washed with brine, dried over $Na_2SO_4$, filtered and evaporated under reduced pressure. The crude residue was purified twice by preparative TLC (DCM/MeOH, 9:1) and then (DCM/MeOH, 95:5) to provide 7-chloro-3-[4-(2,3-dihydroxy-propylsulfamoyl)-benzyl]-4-oxo-1-phenyl-1,4-di-hydroquinoline-2-carboxylic acid methyl ester as light brown powder. MS=556.8 [M+H]$^+$ and 554.9 [M−H]$^-$.

Using the procedure set forth above, substituting appropriate starting materials, the following compounds were prepared:

7-Chloro-3-[4-(2-hydroxyethylsulfanyl)-benzyl]-4-oxo-1-phenyl-1,4-dihydroquinoline-2-carboxylic acid methyl ester (light yellow powder); MS=479.8 [M+H]$^+$; MP=204.0-205.0° C. (compound 55);

7-Chloro-3-(4-methylsulfamoyl-benzyl)-4-oxo-1-phenyl-1,4-dihydroquinoline-2-carboxylic acid methyl ester (light yellow powder); MS=497 [M+H]$^+$ (compound 44);

7-Chloro-3-(4-methoxycarbonyl-benzyl)-4-oxo-1-phenyl-1,4-dihydroquinoline-2-carboxylic acid methyl ester (off-white solid); MS=462 [M+H]$^+$; MP=194.7-195.2° C. (compound 10);

7-Chloro-3-(3-methoxycarbonyl-benzyl)-4-oxo-1-phenyl-1,4-dihydroquinoline-2-carboxylic acid methyl ester (white powder); MS=462 [M+H]$^+$; MP=183-185° C. (compound 23);

7-Chloro-3-(4-methoxy-benzyl)-4-oxo-1-phenyl-1,4-dihydroquinoline-2-carboxylic acid methyl ester (off-white powder); MS=434 [M+H]$^+$; MP=198-200° C. (compound 19);

3-Benzo[1,3]dioxol-5-ylmethyl-4-oxo-1-phenyl-1,4-dihydroquinoline-2-carboxylic acid methyl ester (light yellow powder); MS=414 [M+H]$^+$ (compound 2);

3-(4-Methanesulfonyl-benzyl)-4-oxo-1-phenyl-1,4-dihydroquinoline-2-carboxylic acid methyl ester (off-white powder); MS=448 [M+H]$^+$ (compound 4);

7-Chloro-3-(3,4-dimethoxy-benzyl)-4-oxo-1-phenyl-1,4-dihydroquinoline-2-carboxylic acid methyl ester (light brown solid); MS=464 [M+H]$^+$; MP=153.0-154.5° C. (compound 21);

7-Chloro-3-(3-methoxy-benzyl)-4-oxo-1-phenyl-1,4-dihydroquinoline-2-carboxylic acid methyl ester (white powder); MS=434 [M+H]$^+$; MP=178.5-180.9° C. (compound 20);

7-Chloro-3-(4-methanesulfonyl-benzyl)-4-oxo-1-phenyl-1,4-dihydroquinoline-2-carboxylic acid methyl ester (white solid); MS=482 [M+H]$^+$; MP=215.5-219.0° C. (compound 9);

3-Benzo[1,3]dioxol-5-ylmethyl-7-methoxy-4-oxo-1-phenyl-1,4-dihydroquinoline-2-carboxylic acid methyl ester (off-white powder); MS=444 [M+H]$^+$; MP=171.0-172.1° C. (compound 6);

3-Benzo[1,3]dioxol-5-ylmethyl-6-chloro-4-oxo-1-phenyl-1,4-dihydroquinoline-2-carboxylic acid methyl ester (off-white powder); MS=448 [M+H]$^+$; MP=172.2-177.7° C. (compound 7);

3-Benzo[1,3]dioxol-5-ylmethyl-6-methoxy-4-oxo-1-phenyl-1,4-dihydroquinoline-2-carboxylic acid methyl ester (brown solid); MS=444 [M+H]$^+$; MP=171.9-173.5° C. (compound 5);

1-((1R,2R)-2-Hydroxy-cyclopentyl)-3-(4-methanesulfonyl-benzyl)-7-methyl-4-oxo-1,4-dihydro-[1,8]naphthyridine-2-carboxylic acid methyl ester (yellow solid); MS=471 [M+H]$^+$; MP=200.2-204.6° C. (compound 48);

3-(4-Methanesulfonyl-benzyl)-4-oxo-1-phenyl-1,4-dihydro-[1,8]naphthyridine-2-carboxylic acid methyl ester (off-white solid); MS=449 [M+H]$^+$; MP=235-237° C. (compound 11);

3-(4-Methanesulfonyl-benzyl)-7-methyl-4-oxo-1-phenyl-1,4-dihydro-[1,8]naphthyridine-2-carboxylic acid methyl ester (yellow solid); MS=463 [M+H]$^+$; MP=202-204° C. (compound 35);

1-(3-Hydroxy-cyclohexyl)-3-(4-methanesulfonyl-benzyl)-7-methyl-4-oxo-1,4-dihydro-[1,8]naphthyridine-2-carboxylic acid methyl ester (brown solid); MS=485 [M+H]$^+$; MP=196.6-198° C. (compound 51);

1-Cyclopentyl-3-(4-methanesulfonyl-benzyl)-7-methyl-4-oxo-1,4-dihydro[1,8]naphthyridine-2-carboxylic acid methyl ester (off-white foam); MS=455 [M+H]$^+$; MP=75.0-77.2° C. (compound 28);

3-(4-Methanesulfonyl-benzyl)-7-methyl-4-oxo-1-(tetrahydropyran-4-yl)-1,4-dihydro-[1,8]naphthyridine-2-carboxylic acid methyl ester (yellow foam); MS=471 [M+H]$^+$; MP=207.2-209.2° C. (compound 50);

1-((1R,3R)-3-Hydroxy-cyclopentyl)-3-(4-methanesulfonyl-benzyl)-7-methyl-4-oxo-1,4-dihydro[1,8]naphthyridine-2-carboxylic acid methyl ester (yellow solid); MS=471 [M+H]$^+$; MP=195.1-197.8° C. (compound 54);

1-Isopropyl-3-(4-methanesulfonyl-benzyl)-7-methyl-4-oxo-1,4-dihydro[1,8]-naphthyridine-2-carboxylic acid methyl ester (light yellow solid); MS=429 [M+H]$^+$; MP=73.0-75.5° C. (compound 34);

1-(1,1-Dioxo-tetrahydrothiophen-3-yl)-3-(4-methanesulfonyl-benzyl)-7-methyl-4-oxo-1,4-dihydro-[1,8]naphthyridine-2-carboxylic acid methyl ester (light yellow foam); MS=505 [M+H]$^+$; MP=121.1-123.3° C. (compound 36);

1-Cyclopropyl-3-(4-methanesulfonyl-benzyl)-7-methyl-4-oxo-1,4-dihydro-[1,8]-naphthyridine-2-carboxylic acid methyl ester (light brown foam); MS=427 [M+H]$^+$; MP=73.9-78.8° C. (compound 33);

3-(4-Methanesulfonyl-benzyl)-1-(1-methoxy-prop-2-yl)-7-methyl-4-oxo-1,4-dihydro-[1,8]naphthyridine-2-carboxylic acid methyl ester (yellow solid); MS=459 [M+H]$^+$; MP=125.2-126.6° C. (compound 53);

3-Benzo[1,3]dioxol-5-ylmethyl-1-methyl-4-oxo-1,4-dihydroquinoline-2-carboxylic acid methyl ester (white powder); MS=352 [M+H]$^+$ (compound 3);

3-(4-Methanesulfonyl-benzyl)-1-methyl-4-oxo-1,4-dihydroquinoline-2-carboxylic acid ethyl ester (yellow powder); MS=400 [M+H]$^+$ (compound 1);

3-(4-Acetylaminobenzyl)-7-chloro-4-oxo-1-phenyl-1,4-dihydroquinoline-2-carboxylic acid methyl ester (white powder); MS=461 [M+H]+; MP=157-159° C. (compound 22);

Benzo[1,3]dioxol-5-ylmethyl-7-chloro-4-oxo-1-phenyl-1,4-dihydroquinoline-2-carboxylic acid methyl ester (off-white powder); MS=448 [M+H]+; MP=228.8-230.1° C. (compound 8);

7-Chloro-3-{4-[(2-hydroxyethyl)-methyl-sulfamoyl]-benzyl}-4-oxo-1-phenyl-1,4-dihydroquinoline-2-carboxylic acid methyl ester (off-white powder); MS=541 [M+H]+; MP=95.2-100.2° C.; M+H 541 (compound 59);

3-{4-[2-(tert-Butyl-dimethyl-silanyloxy)-ethylsulfamoyl]-benzyl}-7-chloro-4-oxo-1-phenyl-1,4-dihydroquinoline-2-carboxylic acid methyl ester; MS=641 [M+H]+ (compound 60);

7-Chloro-3-[4-(methoxyoxalyl-sulfamoyl)-benzyl]-4-oxo-1-phenyl-1,4-dihydroquinoline-2-carboxylic acid methyl ester (yellow powder); MS=569 [M+H]+; MP=151.0-154.0° C. (compound 64);

3-[4-(4-tert-Butoxycarbonyl-piperazine-1-sulfonyl)-benzyl]-7-chloro-4-oxo-1-phenyl-1,4-dihydroquinoline-2-carboxylic acid methyl ester (off-white powder); MS=652 [M+H]+ (compound 63);

1-((1R,3S)-3-Hydroxy-cyclopentyl)-3-(4-methanesulfonyl-benzyl)-7-methyl-4-oxo-1,4-dihydro-[1,8]naphthyridine-2-carboxylic acid methyl ester (off-white foam); MS=471 [M+H]+; MP=183.3-187.5° C. (compound 62);

1-Cyclobutyl-3-(4-methanesulfonyl-benzyl)-7-methyl-4-oxo-1,4-dihydro-[1,8]naphthyridine-2-carboxylic acid methyl ester (light yellow foam); MS=441 [M+H]+; MP=90.9-93.3° C. (compound 58);

1-((1S,3S)-3-Hydroxy-cyclopentyl)-3-(4-methanesulfonyl-benzyl)-7-methyl-4-oxo-1,4-dihydro-[1,8]naphthyridine-2-carboxylic acid methyl ester (light yellow foam); MS=471 [M+H]+; MP=118.3-119.7° C. (compound 71);

1-((1R,3R)-3-Hydroxymethyl-cyclopentyl)-3-(4-methanesulfonyl-benzyl)-7-methyl-4-oxo-1,4-dihydro-[1,8]naphthyridine-2-carboxylic acid methyl ester (light brown solid); MS=485 [M+H]+; MP=161.8-164.7° C. (compound 57);

1-(3-hydroxycyclopentyl)-3-(r-methanesulfonylbenzyl)-7-methyl-4-oxo-1,4-dihydro-[1,8]naphthyridine-2-carboxylic acid methyl ester (compound 61);

3-[4-(2-Hydroxy-ethylcarbamoyl)-benzyl]-7-methyl-4-oxo-1-phenyl-1,4-dihydro-[1,8]-naphthyridine-2-carboxylic acid methyl ester (off-white foam); MS=472 [M+H]+; MP=191.7-192.8° C. (compound 68);

3-(4-methoxycarbonyl-benzyl)-7-methyl-4-oxo-1-phenyl-1,4-dihydro[1,8]naphthyridine-2-carboxylic acid methyl ester (compound 73);

1-(4-fluorophenyl)-3-(4-methanesulfonylbenzyl)-7-methyl-4-oxo-1,4-dihydro-[1,8]naphthyridine-2-carboxylic acid methyl ester (compound 74);

3-(4-methoxycarbonyl-benzyl)-7-methyl-4-oxo-1-phenyl-1,4-dihydro[1,8]naphthyridine-2-carboxylic acid (compound 75);

3-[4-(4-hydroxycyclohexylcarbamoyl)benzyl]-7-methyl-4-oxo-1-phenyl-1,4-dihydro[1,8]naphthyridine-2-carboxylic acid methyl ester (compound 76);

1-(3,4-difluorophenyl)-3-(4-methanesulfonylbenzyl)-7-methyl-4-oxo-1,4-dihydro-[1,8]naphthyridine-2-carboxylic acid methyl ester (compound 77);

3-(4-acetylbenzyl)-7-methyl-4-oxo-1-phenyl-1,4-dihydro[1,8]naphtridine-2-carboxylic acid methyl ester (compound 79);

7-chloro-3-[4-(4-methylpiperazin-1-sulfonyl)benzyl]-1-phenyl-2-propionyl-1H-quinlin-4-one (compound 80) mp=>300° C.; M+H 564;

1-(3-fluorophenyl)-3-(4-methanesulfonylbenzyl)-7-methyl-4-oxo-1,4-dihydro-[1,8]naphthyridine-2-carboxylic acid methyl ester (compound 81);

7-methyl-4-oxo-1-phenyl-3-pyrimidin-5-ylmethyl-1,4-dihydro[1,8]naphthyridine-2-carboxylic acid methyl ester (compound 82);

3-benzyl-7-methyl-4-oxo-1-phenyl-1,4-dihydro[1,8]naphthyridine-2-carboxylic acid methyl ester (compound 91);

3-[4-(2-hydroxyethanesulfonyl)benzyl]-7-methyl-4-oxo-1-phenyl-1,4-dihydro[1,8]-naphthyridine-2-carboxylic acid methyl ester (compound 93); and 3-[4-(4-t-butoxycarbonylpiperazine-1-sulfonyl)benzyl]-7-methyl-4-oxo-1-phenyl-1,4-dihydro[1,8]naphthyridine-2-carboxylic acid methyl ester (compound 96).

Example 3

Synthesis of 7-chloro-3-[4-(2-hydroxyethanesulfonyl)-benzyl]-4-oxo-1-phenyl-1,4-dihydroquinoline-2-carboxylic acid methyl ester The synthesis of 7-chloro-3-[4-(2-hydroxyethanesulfonyl)-benzyl]-4-oxo-1-phenyl-1,4-dihydroquinoline-2-carboxylic acid methyl ester (compound 56) was carried out according to the process shown in Scheme 10.

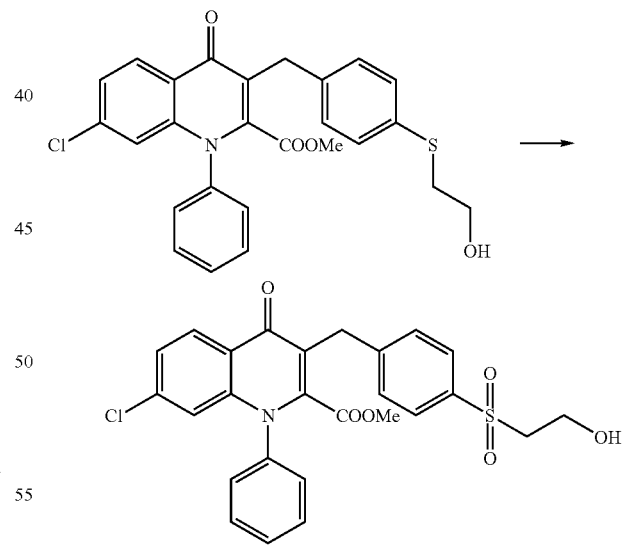

To 7-chloro-3-[4-(2-hydroxy-ethylsulfanyl)-benzyl]-4-oxo-1-phenyl-1,4-dihydro-quinoline-2-carboxylic acid methyl ester (100 mg) in a mixture of THF and MeOH (1:5, 12 mL) was added a solution of OXONE™ (294 mg) in water (3 mL) at 0° C. The reaction mixture was stirred for 1.5 h, and NaHCO₃ (sat aq, 20 mL) added. The resulting mixture was extracted with EtOAc (3×25 mL). The combined organic extracts were washed with brine, dried over Na₂SO₄, filtered and evaporated under reduced pressure to give a yellow-brown oil. The crude residue was purified by flash chromatography (EtOAc/hexane) to give 7-chloro-3-[4-(2-hydroxy-ethane-sulfonyl)-benzyl]-4-oxo-1-phenyl-1,4-dihydroquinoline-2-carboxylic acid methyl ester (23.6 mg) as an off-white powder. MS=512 [M+H]$^+$; MP=172.2-173.5° C.

Example 4

Synthesis of 3-[4-(4-methyl-piperazine-1-sulfonyl)-benzyl]-4-oxo-1-phenyl-1,4-dihydroquinoline-2-carboxylic acid methyl ester The synthesis of 3-[4-(4-methyl-piperazine-1-sulfonyl)-benzyl]-4-oxo-1-phenyl-1,4-di-hydroquinoline-2-carboxylic acid methyl ester (compound 29) was carried out according to the process shown in Scheme 11.

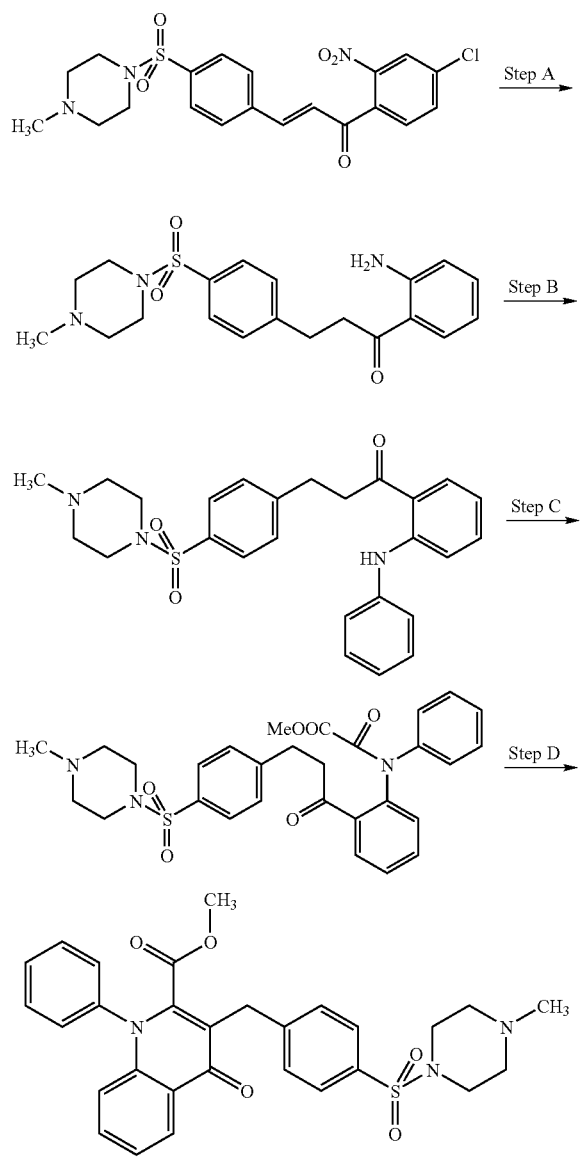

Step A: A mixture of (E)-1-(4-chloro-2-nitro-phenyl)-3-[4-(4-methyl-piperazine-1-sulfonyl)-phenyl]-propenone (1.13 g) and palladium(0) on carbon (10%, 100 mg) in a mixture of EtOH and THF (10:1, 250 mL) was stirred under H$_2$ (balloon pressure) overnight. The reaction mixture was then filtered through glass-fiber filter paper, and the filtrate evaporated under reduced pressure to yield 1-(2-amino-phenyl)-3-[4-(4-methyl-piperazine-1-sulfonyl)-phenyl]-propan-1-one (1.18 g) as a white solid.

Step B: A mixture of 1-(2-aminophenyl)-3-[4-(4-methylpiperazine-1-sulfonyl)-phenyl]-propan-1-one (1.16 g), copper powder (90 mg), KI (19.7 mg), K$_2$CO$_3$ (495 mg) and iodobenzene (1.3 mL) in dibutyl ether (25 mL) was heated at 160° C. (oil bath temperature) overnight. A second aliquot of KI (19.7 mg), K$_2$CO$_3$ (495 mg) and iodobenzene (1.30 mL) was added, and the resulting mixture again heated at 160° C. overnight. The reaction mixture was then cooled and concentrated under reduced pressure. The residue was partitioned between water (50 mL) and EtOAc (50 mL), the organic layer separated, and the aqueous layer was extracted with EtOAc (2×50 mL). The combined organic extracts were washed with brine, dried over Na$_2$SO$_4$, filtered and evaporated under reduced pressure. The crude residue was purified by flash chromatography (DCM/MeOH, 98:2 for 5 minutes, 95:5 from minutes 10 to 15) to afford 3-[4-(4-methyl-piperazine-1-sulfonyl)-phenyl]-1-(2-phenylaminophenyl)-propan-1-one (258 mg). MS=464.0 [M+H]$^+$.

Step C: Methyl oxalyl chloride (0.8 mL) was added to a solution of 3-[4-(4-methyl-piperazine-1-sulfonyl)-phenyl]-1-(2-phenylaminophenyl)-propan-1-one (0.237 g, 0.5 mmol) in toluene (20 mL). The reaction mixture was heated at reflux overnight, then evaporated under reduced pressure to give N-(2-{3-[4-(4-methylpiperazine-1-sulfonyl)-phenyl]-propionyl}-phenyl)-N-phenyl-oxalamic acid methyl ester, which was used without further purification. MS=550.0 [M+H]$^+$.

Step D: A mixture of N-(2-{3-[4-(4-methylpiperazine-1-sulfonyl)-phenyl]-propionyl}-phenyl)-N-phenyl-oxalamic acid methyl ester (ca. 0.5 mmol) and K$_2$CO$_3$ (128 mg) in MeOH (30 mL) was heated at reflux for 1 h. The reaction mixture was then cooled and evaporated under reduced pressure. The residue was partitioned between water (25 mL) and EtOAc (25 mL), the organic layer separated, and the aqueous layer extracted with EtOAc (2×25 mL). The combined organic extracts were washed with brine, dried over Na$_2$SO$_4$, filtered and concentrated under reduced pressure. The crude residue was purified twice by flash chromatography (DCM/MeOH) and once by preparative TLC (DCM/MeOH, 95:5) to afford 3-[4-(4-methylpiperazine-1-sulfonyl)-benzyl]-4-oxo-1-phenyl-1,4-dihydroquinoline-2-carboxylic acid methyl ester as light brown solid. MS=532.0 [M+H]$^+$. MP=210.0-212.0° C.

Example 5

Synthesis of 3-(4-carboxy-benzyl)-7-chloro-4-oxo-1-phenyl-1,4-dihydro-quinoline-2-carboxylic acid methyl ester The synthesis of 3-(4-carboxy-benzyl)-7-chloro-4-oxo-1-phenyl-1,4-dihydroquinoline-2-carboxylic acid methyl ester (compound 12) was carried out as shown in Scheme 12.

SCHEME 12

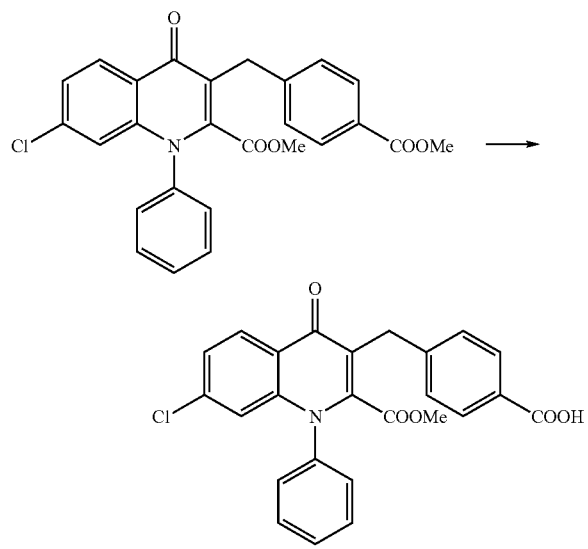

A mixture of 7-chloro-3-(4-methoxycarbonyl-benzyl)-4-oxo-1-phenyl-1,4-dihydro-quinoline-2-carboxylic acid methyl ester (compound 10, 31 mg) and LiOH (1 M aq, 1 mL) in MeOH (10 mL) was stirred at RT overnight. The reaction mixture was then stirred at 50° C. for 3 h, then extracted with EtOAc. The organic layer was separated, the aqueous layer acidified by adding AcOH (aq), and the resulting mixture extracted with EtOAc. The combined organic extracts were dried over $Na_2SO_4$, filtered and evaporated under reduced pressure. The crude residue was purified by preparative TLC (hexane/acetone, 70:30+1% AcOH) to afford 11 mg of 3-(4-carboxybenzyl)-7-chloro-4-oxo-1-phenyl-1,4-dihydro-quinoline-2-carboxylic acid methyl ester as an off-white solid. MS=447; MP=258.0-261.0° C.

Example 6

Synthesis of 7-chloro-3-[4-(2-dimethylcarbamoyl-1,1-dimethylethylcarbamoyl)-benzyl]-4-oxo-1-phenyl-1,4-dihydroquinoline-2-carboxylic acid methyl ester The synthesis of 7-chloro-3-[4-(2-dimethylcarbamoyl-1,1-dimethylethylcarbamoyl)-benzyl]-4-oxo-1-phenyl-1,4-dihydroquinoline-2-carboxylic acid methyl ester (compound 38) was carried out according to the process shown in Scheme 13.

SCHEME 13

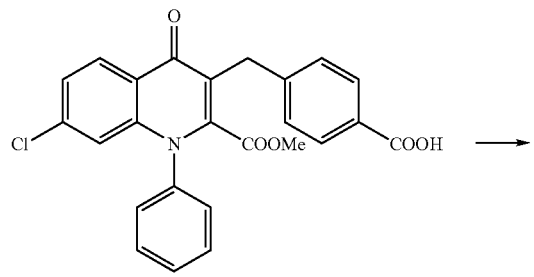

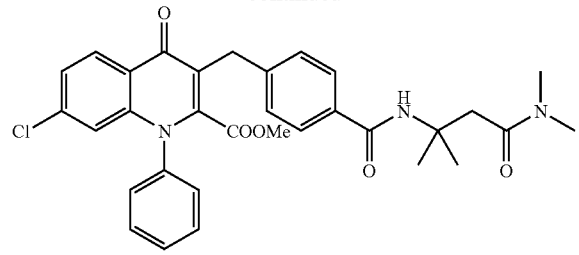

A mixture of 3-(4-carboxy-benzyl)-7-chloro-4-oxo-1-phenyl-1,4-dihydroquinoline-2-carboxylic acid methyl ester (75 mg, 0.17 mmol), 3-amino-3,N,N-trimethyl-butyramide (24 mg, 0.17 mmol), BOP (150 mg, 0.34 mmol) and DIPEA (1 mL) in THF (15 mL) was stirred at RT overnight. The reaction mixture was partitioned between water and EtOAc, the organic layer separated, washed with water, dried over $Na_2SO_4$, filtered, and evaporated under reduced pressure. The crude residue was purified by preparative TLC (EtOAc/hexane, 75:25) to yield 7-chloro-3-[4-(2-dimethylcarbamoyl-1,1-dimethyl-ethylcarbamoyl)-benzyl]-4-oxo-1-phenyl-1,4-dihydro-quinoline-2-carboxylic acid methyl ester (71 mg) as a light brown foam. MS=574 [M+H]$^+$; MP=84.1-95.5° C.

Using the above described procedure and the appropriate starting materials, the following compounds were prepared:

7-Chloro-4-oxo-1-phenyl-3-{4-[((S)-1-pyrrolidin-2-ylmethyl)-carbamoyl]-benzyl}-1,4-dihydroquinoline-2-carboxylic acid methyl ester (light brown foam), MS=530 [M+H]$^+$; MP=124-138° C. (compound 39);

3-[4-(2-Amino-2-methyl-propylcarbamoyl)-benzyl]-7-chloro-4-oxo-1-phenyl-1,4-dihydroquinoline-2-carboxylic acid methyl ester (light brown solid), MS=518 [M+H]$^+$; MP=210.6-212.7° C. (compound 52);

7-Chloro-4-oxo-1-phenyl-3-[4-(pyrrolidin-3-ylcarbamoyl)-benzyl]-1,4-dihydroquinoline-2-carboxylic acid methyl ester (light yellow foam), MS=516 [M+H]$^+$; MP=98.0-105.0° C. (compound 43);

7-Chloro-4-oxo-1-phenyl-3-[4-(piperidin-4-ylcarbamoyl)-benzyl]-1,4-dihydroquinoline-2-carboxylic acid methyl ester (brown solid), MS=530 [M+H]$^+$; MP=221.5-234.3° C. (compound 47);

7-Chloro-3-[4-(2-dimethylaminoethylcarbamoyl)-benzyl]-4-oxo-1-phenyl-1,4-dihydro-quinoline-2-carboxylic acid methyl ester (light yellow, foam), MS=518 [M+H]$^+$; MP=218.0-223.0° C. (compound 41); and 7-Chloro-4-oxo-1-phenyl-3-[4-(2-pyrrolidin-1-yl-ethylcarbamoyl)-benzyl]-1,4-dihydro-quinoline-2-carboxylic acid methyl ester (light yellow, foam), MS=544 [M+H]$^+$; MP=186.0-196.0° C. (compound 42).

Example 7

Synthesis of 7-chloro-3-[4-(2-hydroxyethylcarbamoyl)-benzyl]-4-oxo-1-phenyl-1,4-dihydroquinoline-2-carboxylic acid methyl ester (compound 18)

The synthesis of 7-chloro-3-[4-(2-hydroxyethylcarbamoyl)-benzyl]-4-oxo-1-phenyl-1,4-dihydroquinoline-2-carboxylic acid methyl ester (compound 18) was carried out according to the process shown in Scheme 14.

SCHEME 14

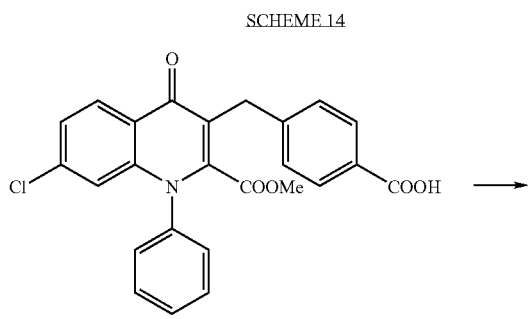

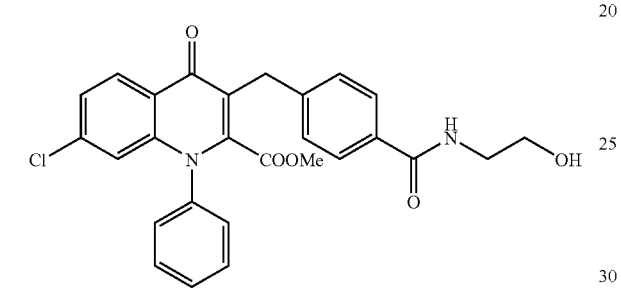

A mixture of 3-(4-carboxybenzyl)-7-chloro-4-oxo-1-phenyl-1,4-dihydroquinoline-2-carboxylic acid methyl ester (167 mg, 0.37 mmol), 2-aminoethanol (34 mg, 0.56 mmol), HOBt (50 mg), EDCI (142 mg, 0.74 mmol) and DIPEA (0.5 mL) in DCM (10 mL) and DMF (0.4 mL) was stirred at RT for 2 h. The reaction mixture was then partitioned between water and EtOAc. The organic layer was separated, washed twice with water, dried over $Na_2SO_4$, filtered and evaporated under reduced pressure. The crude residue was purified twice by flash chromatography to afford 7-chloro-3-[4-(2-hydroxy-ethylcarbamoyl)-benzyl]-4-oxo-1-phenyl-1,4-dihydro-quinoline-2-carboxylic acid methyl ester (99 mg) as an off-white powder. MS=491 [M+H]$^+$; MP=162-163.5° C.

In the same manner, using the appropriate starting materials, the following compounds were prepared:

7-Chloro-3-[4-(1,3-dihydroxy-prop-2-ylcarbamoyl)-benzyl]-4-oxo-1-phenyl-1,4-dihydro-quinoline-2-carboxylic acid methyl ester (light brown solid), MS=521 [M+H]$^+$; MP=110-112° C. (compound 24);

7-Chloro-3-[4-(2-morpholin-4-yl-ethylcarbamoyl)-benzyl]-4-oxo-1-phenyl-1,4-dihydro-quinoline-2-carboxylic acid methyl ester (light brown solid), MS=560 [M+H]$^+$; MP=102-106° C. (compound 26);

7-Chloro-3-[4-(2,3-dihydroxy-propylcarbamoyl)-benzyl]-4-oxo-1-phenyl-1,4-dihydro-quinoline-2-carboxylic acid methyl ester (light yellow powder), MS=521 [M+H]$^+$; MP=98.0-103.9° C. (compound 25);

7-Chloro-3-(4-N,N-dimethylcarbamoyl-benzyl)-4-oxo-1-phenyl-1,4-dihydroquinoline-2-carboxylic acid methyl ester (light yellow powder), MS=475 [M+H]$^+$; MP=227.3-228.1° C. (compound 16);

7-chloro-4-oxo-1-phenyl-3-[4-(piperazine-1-carbonyl)-benzyl]-1,4-dihydroquinoline-2-carboxylic acid methyl ester hydrochloride salt (compound 17) (yellow powder) (the salt was generated by adding a solution of HCl in $Et_2O$ to a solution of 7-chloro-4-oxo-1-phenyl-3-[4-(piperazine-1-carbonyl)-benzyl]-1,4-dihydroquinoline-2-carboxylic acid methyl ester in EtOAc), MS=516 [M+H]$^+$; MP=161-164° C.;

7-chloro-3-[4-(2-hydroxy-ethylcarbamoyl)-benzyl]-4-oxo-1-phenyl-1,4-dihydro-quinoline-2-carboxylic acid (compound 49);

3-[4-(2-hydroxy-2-methylpropylcarbamoyl)-benzyl]-7-methyl-4-oxo-1-phenyl-1,4-dihydro[1,8]naphthyridine-2-carboxylic acid methyl ester (compound 78); and 3-[4-(2-acetoxyethylcarbamoyl)benzyl]-7-chloro-4-oxo-1-phenyl-1,4-dihydroquinoline-2-carboxylic acid methyl ester (compound 95).

Example 8

Synthesis of 7-Chloro-3-[4-(4-hydroxycyclohexylcarbamoyl)-benzyl]-4-oxo-1-phenyl-1,4-dihydro-quinoline-2-carboxylic acid methyl ester The synthesis of 7-chloro-3-[4-(4-hydroxycyclohexylcarbamoyl)-benzyl]-4-oxo-1-phenyl-1,4-dihydroquinoline-2-carboxylic acid methyl ester (compound 37) was carried out according to the process shown in Scheme 15.

SCHEME 15

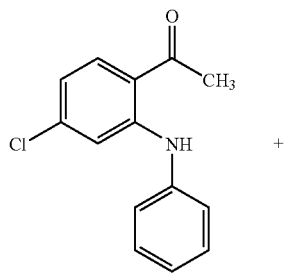

+

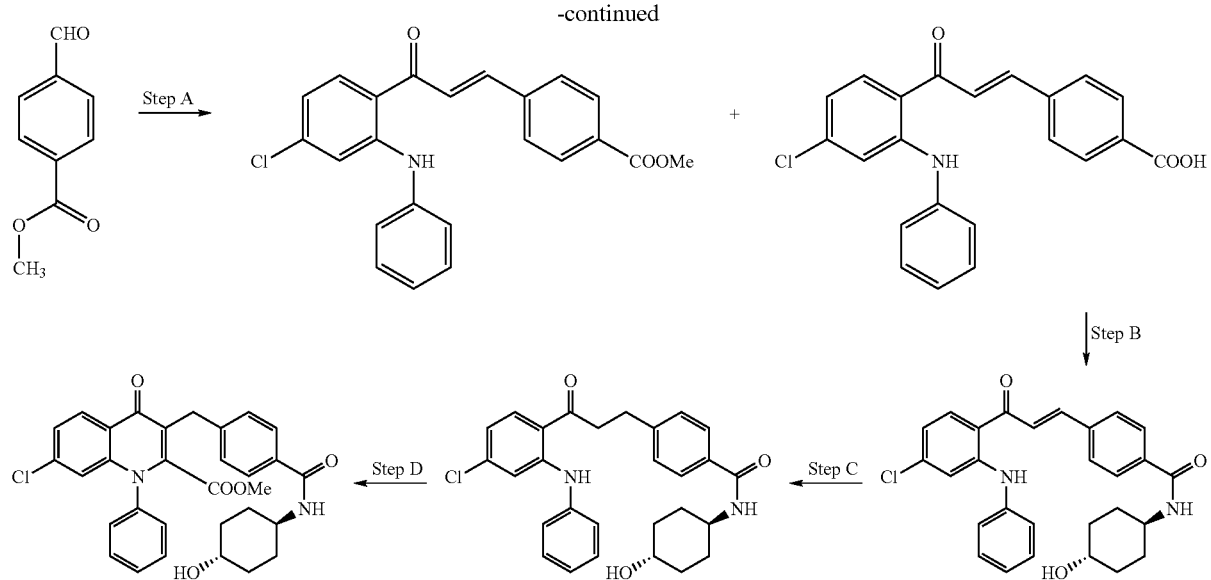

Step A: A mixture of 1-(4-chloro-2-phenylaminophenyl)-ethanone (1.7 g, 6.9 mmol), 4-formyl-benzoic acid methyl ester (1.14 g, 6.9 mmol) and NaOH (2 M aq, 2 mL) in MeOH (30 mL) was stirred at RT overnight. The precipitate formed was collected by filtration and dried in a vacuum oven to afford 0.7 g of 4-[(E)-3-(4-chloro-2-phenylamino-phenyl)-3-oxo-propenyl]-benzoic acid methyl ester as an orange solid. The mother liquors were acidified by adding glacial HOAc (99%) to pH 5, and the resulting mixture extracted with EtOAc. The combined organic extracts were dried over Na$_2$SO$_4$, filtered and evaporated under reduced pressure to yield 4-[(E)-3-(4-chloro-2-phenylamino-phenyl)-3-oxo-propenyl]-benzoic acid (350 mg).

Step B: A mixture of 4-[(E)-3-(4-chloro-2-phenylamino-phenyl)-3-oxo-propenyl]-benzoic acid (0.2 g, 0.53 mmol), 4-amino-cyclohexanol (61 mg, 0.53 mmol), EDCI (152 mg, 0.8 mmol), HOBt (25 mg), DIPEA (1 mL) in THF (50 mL) was stirred at RT overnight. The resulting mixture was evaporated under reduced pressure, and the residue partitioned between water and EtOAc. The resulting precipitate was collected by filtration and dried in a vacuum oven, the filtrate separated, the organic layer dried over Na$_2$SO$_4$, filtered and evaporated under reduced pressure. The residue was purified by preparative TLC (EtOAc/hexane, 75:25) and combined with the solid collected to yield 4-[(E)-3-(4-chloro-2-phenylamino-phenyl)-3-oxo-propenyl]-N-(4-hydroxy-cyclohexyl)-benzamide (197 mg). MS=475 [M+H]$^+$.

Step C: A mixture of 4-[(E)-3-(4-chloro-2-phenylamino-phenyl)-3-oxo-propenyl]-N-(4-hydroxy-cyclohexyl)-benzamide (197 mg) and platinum (V) oxide (50 mg) in a mixture of EtOH, THF and acetone (100/50/100 mL) was stirred under H$_2$ (balloon pressure) at RT for 1 h. The resulting mixture was filtered, and the filtrate concentrate under reduced pressure to yield 4-[3-(4-chloro-2-phenylamino-phenyl)-3-oxo-propyl]-N-(4-hydroxy-cyclohexyl)-benzamide (190 mg).

Step D: A mixture of 4-[3-(4-chloro-2-phenylamino-phenyl)-3-oxo-propyl]-N-(4-hydroxycyclohexyl)-benzamide (190 mg) and methyl oxalyl chloride (0.4 mL) in toluene (40 mL) was heated at reflux overnight, then concentrated under reduced pressure. The residue was dissolved in MeOH (30 mL), K$_2$CO$_3$ (100 mg) added, and the resulting mixture heated at reflux for 10 min. The reaction mixture was then cooled, filtered, and the filtrate evaporated under reduced pressure. The crude residue was purified by preparative TLC (EtOAc) to afford 7-chloro-3-[4-(4-hydroxy-cyclohexylcarbamoyl)-benzyl]-4-oxo-1-phenyl-1,4-dihydroquinoline-2-carboxylic acid methyl ester (compound 37) (63 mg) as an off-white solid. MS=545 [M+H]$^+$; MP=150.6-152.5° C.

Using the above described procedure and the appropriate starting materials, the following compounds were prepared:

7-Chloro-4-oxo-1-phenyl-3-[4-(tetrahydropyran-4-ylcarbamoyl)-benzyl]-1,4-dihydro-quinoline-2-carboxylic acid methyl ester (yellow solid); MS=531 [M+H]$^+$; MP=209-213° C. (compound 45);

7-Chloro-3-[4-(2-hydroxy-2-methylpropylcarbamoyl)-benzyl]-4-oxo-1-phenyl-1,4-dihydroquinoline-2-carboxylic acid methyl ester (light brown solid); MS=519 [M+H]$^+$; MP=282-286° C. (compound 40);

7-Chloro-3-(4-ethylcarbamoyl-benzyl)-4-oxo-1-phenyl-1,4-dihydroquinoline-2-carboxylic acid methyl ester (light brown solid); MS=475 [M+H]$^+$; MP=209.0-212.0° C. (compound 15);

7-Chloro-3-(4-methylcarbamoyl-benzyl)-4-oxo-1-phenyl-1,4-dihydroquinoline-2-carboxylic acid methyl ester (light brown solid); MS=461 [M+H]$^+$; MP=203.3-205.5° C. (compound 14);

7-Chloro-3-[3-(2-hydroxyethylcarbamoyl)-benzyl]-4-oxo-1-phenyl-1,4-dihydro-quinoline-2-carboxylic acid methyl ester (light brown solid); MS=491 [M+H]$^+$; MP=216-218° C. (compound 27); and 3-(4-Methylcarbamoyl-benzyl)-4-oxo-1-phenyl-1,4-dihydroquinoline-2-carboxylic acid methyl ester (brown powder) (compound 13); MS=427 [M+H]$^+$; MP=199.3-200.3° C.

Example 9

Synthesis of 7-Chloro-3-[4-(2-hydroxy-ethylsulfamoyl)-benzyl]-4-oxo-1-phenyl-1,4-dihydro-quinoline-2-carboxylic acid methyl ester The synthesis of 7-chloro-3-[4-(2-hydroxy-ethylsulfamoyl)-benzyl]-4-oxo-1-phenyl-1,4-dihydro-quinoline-2- carboxylic acid methyl ester (compound 65) was carried out according to the process shown in Scheme 16.

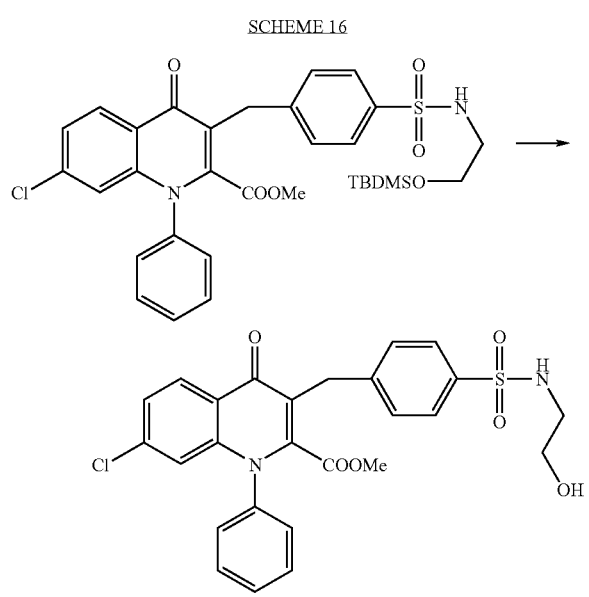

A solution of tetrabutylammonium fluoride (1 M in THF, 0.26 mL) was added to a solution of 3-{4-[2-(tert-butyl-dimethyl-silanyloxy)-ethylsulfamoyl]-benzyl}-7-chloro-4-oxo-1-phenyl-1,4-dihydroquinoline-2-carboxylic acid methyl ester (113 mg) in THF (5 mL) and the resulting mixture was stirred for 1 h. The reaction mixture was partitioned between EtOAc and water, the organic layer separated and the aqueous layer was extracted with EtOAc (2×25 mL). The combined organic extracts were washed with brine, dried over anhydrous $Na_2SO_4$, filtered and evaporated under reduced pressure. The yellow solid residue was purified by flash chromatography (DCM/MeOH, 90/10) to afford 7-chloro-3-[4-(2-hydroxy-ethylsulfamoyl)-benzyl]-4-oxo-1-phenyl-1,4-dihydro-quinoline-2-carboxylic acid methyl ester as an off-white powder. MS=527 $[M+H]^+$; MP=191.5-193.1° C.

Example 10

Synthesis of 7-Chloro-4-oxo-1-phenyl-3-[4-(piperazine-1-sulfonyl)-benzyl]-1,4-dihydroquinoline-2-carboxylic acid methyl ester trifluoroactetate The synthesis of 7-chloro-4-oxo-1-phenyl-3-[4-(piperazine-1-sulfonyl)-benzyl]-1,4-di-hydroquinoline-2-carboxylic acid methyl ester trifluoroacetate (compound 66) was carried out according to the process shown in Scheme 17.

SCHEME 17

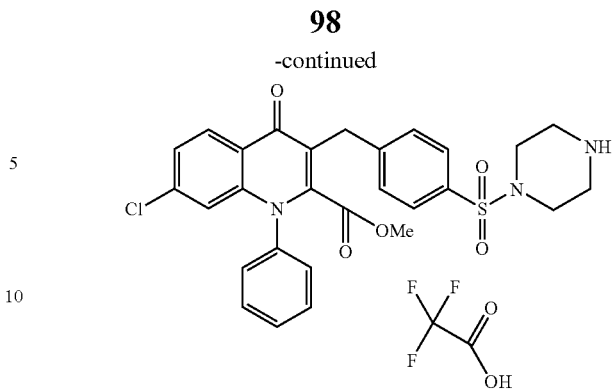

A mixture of TFA and DCM (1:4, 5 mL) was added to 3-[4-(4-t-butoxycarbonylpiperazine-1-sulfonyl)-benzyl]-7-chloro-4-oxo-1-phenyl-1,4-dihydroquinoline-2-carboxylic acid methyl ester (48 mg, 0.07 mmol) and the resulting mixture stirred at RT for 2 h. The reaction mixture was evaporated under reduced pressure, and the oily solid residue was purified by flash chromatography (DCM/MeOH, 100:0 to 90:10) to afford 7-chloro-4-oxo-1-phenyl-3-[4-(piperazine-1-sulfonyl)-benzyl]-1,4-dihydro-quinoline-2-carboxylic acid methyl ester trifluoroacetate as an off-white powder. MS=552 $[M+H]^+$; MP=203.0-205.0° C.

7-Chloro-4-oxo-1-phenyl-3-[4-(piperazine-1-sulfonyl)-benzyl]-1,4-dihydroquinoline-2-carboxylic acid methyl ester bishydrochloride (off-white powder) (compound 67) can be prepared utilizing HCl in 1,4-dioxane instead of TFA in DCM. MS=552 $[M+H]^+$; MP=214.0-215.5° C.

Similarly, proceeding as described above and substituting the appropriate reagents, the compound 7-methyl-4-oxo-1-phenyl-3-[4-(piperazine-1-sulfonyl)benzyl]-1,4-dihydro[1,8]-naphthyridine-2-carboxylic acid methyl ester (compound 97) was prepared.

Example 11

Synthesis of 3-[4-(2-Bromoacetyl)-benzyl]-7-methyl-4-oxo-1-phenyl-1,4-dihydro-[1,8]naphthyridine-2-carboxylic acid methyl ester The synthesis of 3-[4-(2-bromoacetyl)-benzyl]-7-methyl-4-oxo-1-phenyl-1,4-dihydro-[1,8]naphthyridine-2-carboxylic acid methyl ester (compound 89) was carried out according to the process shown in Scheme 18.

SCHEME 18

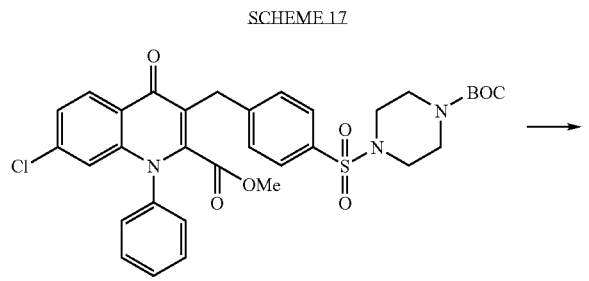

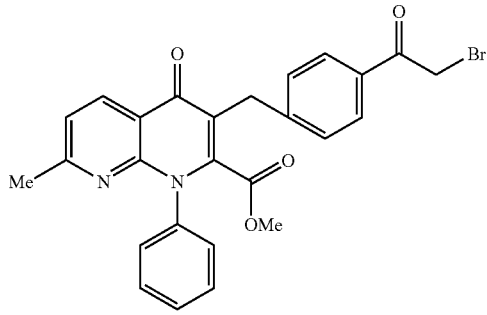

Tetrabutylammonium tribromide (72 mg, 0.15 mmol) was added to a solution of 3-(4-acetylbenzyl)-7-methyl-4-oxo-1-phenyl-1,4-dihydro-[1,8]naphthyridine-2-carboxylic acid methyl ester (53 mg, 0.12 mmol) in MeOH (8 mL), and the resulting mixture stirred at RT overnight. The reaction mixture was concentrated under reduced pressure, and the crude residue purified by preparative TLC (EtOAc/hexane, 10/90) to afford 23 of 3-[4-(2-bromoacetyl)-benzyl]-7-methyl-4-oxo-1-phenyl-1,4-dihydro-[1,8]naphthyridine-2-carboxylic acid methyl ester as an off-white powder. MS=507 [M+H]$^+$; MP=189.0-191.1° C.

Example 12

Synthesis of 3-[4-(2-Hydroxyacetyl)-benzyl]-7-methyl-4-oxo-1-phenyl-1,4-dihydro-[1,8]naphthyridine-2-carboxylic acid methyl ester The synthesis of 3-[4-(2-hydroxyacetyl)-benzyl]-7-methyl-4-oxo-1-phenyl-1,4-dihydro-[1,8]naphthyridine-2-carboxylic acid methyl ester (compound 90) was carried out as shown in Scheme 19.

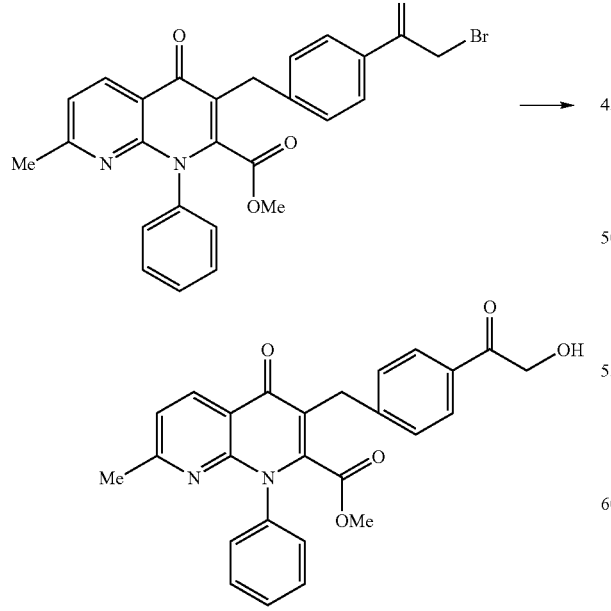

A mixture of 3-[4-(2-bromo-acetyl)-benzyl]-7-methyl-4-oxo-1-phenyl-1,4-dihydro-[1,8]naphthyridine-2-carboxylic acid methyl ester (38 mg, 0.075 mmol) and sodium formate (25.5 mg, 5 eq.) in EtOH (15 mL) was heated at 80° C. overnight. The reaction mixture was concentrated under reduced pressure and filtered. The crude residue was purified by preparative TLC (EtOAc/hexane, 60/40) to afford 14 mg of 3-[4-(2-hydroxy-acetyl)-benzyl]-7-methyl-4-oxo-1-phenyl-1,4-dihydro-[1,8]naphthyridine-2-carboxylic acid methyl ester as an off-white powder. MS=443 [M+H]$^+$; MP=189.9-192.9° C.

Example 13

Synthesis of 3-[4-(2-Hydroxy-2-methylpropylsulfonamoyl)benzyl]-4-oxo-7-chloro-1-phenyl-1,4-dihydroquinoline-2-carboxylic acid Methyl Ester 3-[4-(2-Hydroxy-2-methylpropylsulfonamoyl)benzyl]-4-oxo-7-chloro-1-phenyl-1,4-dihydroquinoline-2-carboxylic acid methyl ester (compound 85) was prepared as shown in Scheme 20.

SCHEME 20

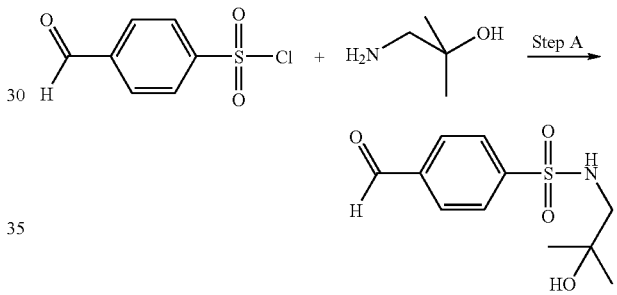

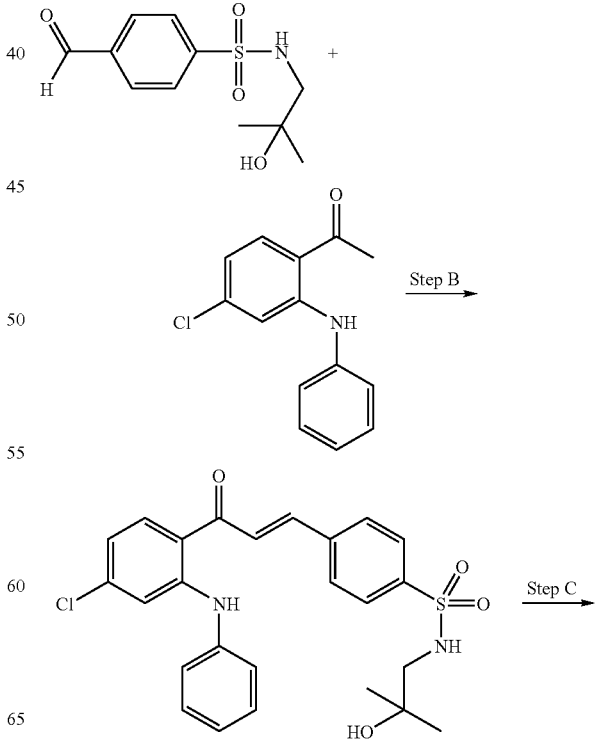

101

-continued

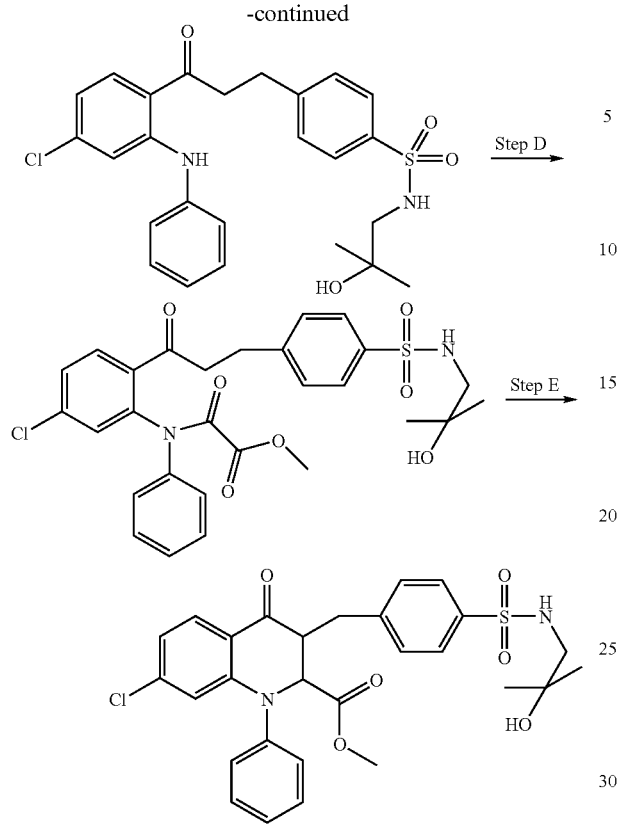

Step A: To a solution of 4-formyl-benzene sulfonyl chloride (1.0 g) in MeOH was added NaHCO3 (0.425 g), followed by 1-amino-2-methylpropan-2-ol (0.566 g). The reaction mixture was stirred for 1 h at RT, then filtered through Celite and the solvent removed under reduced pressure to provide 4-formyl-N-(2-hydroxy-2-methylpropyl)-benzene sulfonamide.

Step B: To a mixture of 1-(4-chloro-2-phenylaminophenyl) ethanone (0.401 g) and 4-formyl-N-(2-hydroxy-2-methylpropyl)-benzene sulfonamide (0.420 g) in MeOH (10 mL) was added NaOH (1.35 mL, 2 N, aq), and the mixture stirred overnight at RT. The product was concentrated under reduced pressure, washed with EtOAc, $H_2O$ and brine, then dried over $Na_2SO_4$. The partially-purified product was chromatographed on anhydrous silica (DCM for 0-10 min, then MeOH/DCM for 11-30 min) to provide 4-[3-(4-chloro-2-phenylaminophenyl)-3-oxo-propenyl]-N-(2-hydroxy-2-methylpropyl)-benzene sulfonamide (0.540 g).

Step C: To a solution of 4-[3-(4-chloro-2-phenylaminophenyl)-3-oxo-propenyl]-N-(2-hydroxy-2-methylpropyl)-benzene sulfonamide (0.535 g) in EtOAc (100 mL) and EtOH (50 mL) was added Pt(IV)O$_2$, and the mixture stirred under H$_2$ for 1.5 h. The product was filtered and concentrated under reduced pressure to provide 4-[3-(4-chloro-2-phenylaminophenyl)-3-oxo-propyl]-N-(2-hydroxy-2-methylpropyl)-benzene sulfonamide as a yellow oily solid.

Step D: To 4-[3-(4-chloro-2-phenylaminophenyl)-3-oxo-propyl]-N-(2-hydroxy-2-methylpropyl)-benzene sulfonamide (0.150 g) was added toluene (15 mL), followed by methyl oxalyl chloride (0.6 mL), and the mixture heated at 80° C. for 3 h to provide N-(5-chloro-2-{3-[4-(2-hydroxy-2-methylpropylsulfamoyl)-phenyl]-propionyl}-phenyl)-N-phenyl-oxalamic acid methyl ester. The product was used without further purification.

102

Step E: To a solution of N-(5-chloro-2-{3-[4-(2-hydroxy-2-methylpropylsulfamoyl)-phenyl]-propionyl}-phenyl)-N-phenyl-oxalamic acid methyl ester in toluene was added $K_2CO_3$ (0.073 g) in MeOH (10 mL), and the mixture stirred at 80° C. for 2 h. The product was washed with EtOAc, $H_2O$, and brine, dried over $Na_2SO_4$, and chromatographed on anhydrous silica with 3% MeOH/DCM. The product was finally purified on anhydrous silica with 5% MeOH/DCM to provide 3-[4-(2-Hydroxy-2-methylpropylsulfonamoyl)benzyl]-4-oxo-7-chloro-1-phenyl-1,4-dihydroquinoline-2-carboxylic acid methyl ester (compound 85) (M+H 555.1; mp=240.0-242.6° C.).

Example 14

Synthesis of 3-[4-(2-Hydroxy-2-methylpropylsulfonamoyl)benzyl]-4-oxo-7-chloro-1-phenyl-2-acetyl-1,4-dihydroquinoline The synthesis of 3-[4-(2-hydroxy-2-methylpropylsulfonamoyl)benzyl]-4-oxo-7-chloro-1-phenyl-2-acetyl-1,4-dihydroquinoline (compound 88) was performed as shown in Scheme 21.

SCHEME 21

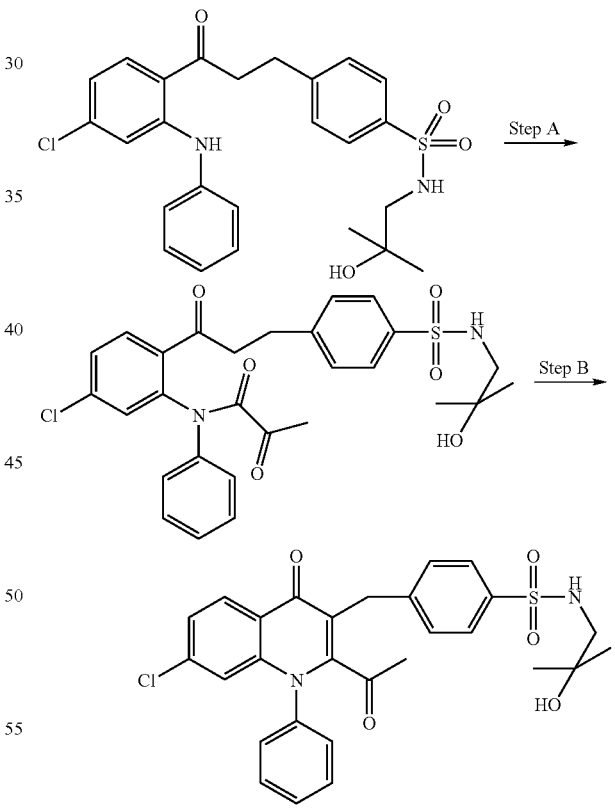

Step A: to pyruvic acid (12.2 g) was added methyl-α,α-dichloromethyl ether (12.3 mL) slowly over 20 min. The reaction mixture was then heated to 50° C. for 30 min., and cooled to RT overnight. An additional aliquot of methyl-α,α-dichloromethyl ether (4 mL) was added slowly, and the mixture heated to 50° C. for 2 h, then cooled to 20° C. The unreacted starting materials were removed by evaporation under reduced pressure to provide 2-oxopropionyl chloride.

To 4-[3-(4-chloro-2-phenylaminophenyl)-3-oxo-propyl]-N-(2-hydroxy-2-methylpropyl)-benzenesulfonamide (0.138 g) in toluene (10 mL) was added 2-oxopropionyl chloride (0.3 mL), and the mixture heated at 120° C. for 3 h to form N-(5-chloro-2-{3-[4-(2-hydroxy-2-methylpropylsulfamoyl)-phenyl]-propionyl}-phenyl)-2-oxo-N-phenyl-propionamide, which was used without further purification.

Step B: To N-(5-chloro-2-{3-[4-(2-hydroxy-2-methylpropylsulfamoyl)-phenyl]-propionyl}-phenyl)-2-oxo-N-phenyl-propionamide in MeOH was added $K_2CO_3$ (0.067 g), and the reaction mixture heated to 80° C. for 2 h. An additional aliquot of $K_2CO_3$ (1 g) was added, and the mixture heated an additional 2 h. The product was allowed to cool to RT, then taken up in $EtOAc/H_2O$, washed 3× with EtOAc, brine, and dried over $Na_2SO_4$. The crude product was then chromatographed on prep silica (5% MeOH/DCM) to provide 3-[4-(2-hydroxy-2-methylpropylsulfonamoyl)benzyl]-4-oxo-7-chloro-1-phenyl-2-acetyl-1,4-dihydroquinoline (compound 88). MS=539 $[M+H]^+$ Similarly, proceeding as set forth above and substituting the appropriate reactants, the compound 4-(7-chloro-4-oxo-1-phenyl-2-propionyl-1,4-dihydroquinolin-3-ylmethyl)-N-(2-hydroxy-2-methylpropyl)-benzensulfonamide (compound 86, M+H 553) was prepared.

Example 15

Synthesis of 7-Chloro-3-[4-(4-hydroxypiperidine-1-sulfonyl)-benzyl]-4-oxo-1-phenyl-1,4-dihydroquinoline-2-carboxylic acid methyl ester (compound 69)

Step A: To 4-formyl-benzenesulfonyl chloride (1.0 g) in DCM (10 mL) was added 4-hydroxypiperidine (0.984 g), followed by $NaHCO_3$ (10 mL, aq sat'd) and the mixture stirred for 2 h at RT. The aqueous layer was washed with DCM (2×25 mL), and the combined organic portions washed with brine, dried over $Na_2SO_4$, filtered, and the solvent removed under reduced pressure to provide 4-(4-hydroxypiperidine-1-sulfonyl)benzaldehyde. The product was purified on anhydrous silica (10% MeOH/DCM). M+H 269.9

Step B: To 1-(4-chloro-2-phenylamino-phenyl)ethanone (0.500 g) and 4-(4-hydroxypiperidine-1-sulfonyl)benzaldehyde (0.548 g) in MeOH (10 mL) was added NaOH (1.65 mL, 2 N aq), and the mixture allowed to stir overnight at RT. The product crashed out of solution, and was collected on a sintered glass funnel, rinsed with water, and taken up in MeOH. The water and MeOH were removed under reduced pressure to provide 1-(4-chloro-2-phenylamino-phenyl)-3-[4-(4-hydroxypiperidine-1-sulfonyl)-phenyl]propenone. The product was reduced as described in Example 13, Step C, to produce 1-(4-chloro-2-phenylamino-phenyl)-3-[4-(4-hydroxypiperidine-1-sulfonyl)-phenyl]propan-1-one.

Step C: To 1-(4-chloro-2-phenylamino-phenyl)-3-[4-(4-hydroxypiperidine-1-sulfonyl)-phenyl]propan-1-one (0.200 g) in toluene (20 mL) was added methyl oxalyl chloride (0.64 mL). The mixture was heated at 120° C. for 3 h, then stirred overnight at RT. The product, N-(5-chloro-2-{3-[4-(4-hydroxypiperidine-1-sulfonyl)-phenyl]-propionyl}-phenyl)-N-phenyl-oxalamic acid methyl ester, was used without further purification.

Step D: To N-(5-chloro-2-{3-[4-(4-hydroxypiperidine-1-sulfonyl)-phenyl]-propionyl}-phenyl)-N-phenyl-oxalamic acid methyl ester (0.40 g) in MeOH (15 mL) was added $K_2CO_3$ (0.096 g), and the mixture heated at 80° C. for 1.5 h, then concentrated. The residue was taken up in $EtOAc/H_2O$, and the aqueous layer washed with EtOAc (2×25 mL). The combined organic layers were dried over $Na_2SO_4$, and the solvent removed under reduced pressure. The residue was chromatographed on anhydrous silica (20% EtOAc/hexanes 0-5 min; 60% EtOAc/hexanes 6-10 min; 100% EtOAc 11-40 min) to provide 7-chloro-3-[4-(4-hydroxypiperidine-1-sulfonyl)-benzyl]-4-oxo-1-phenyl-1,4-dihydroquinoline-2-carboxylic acid methyl ester (compound 69). M+H 567; mp=170.0-171.0° C.

Similarly, proceeding as described above with appropriate reagent substitution, the compound 3-[4-(4-hydroxypiperidine-1-sulfonyl)benzyl]-7-methyl-4-oxo-1-phenyl-1,4-dihydro-[1,8]naphthyridine-2-carboxylic acid methyl ester (compound 99) was prepared.

Example 16

Synthesis of 7-Chloro-3-[4-(3-hydroxypyrrolidine-1-sulfonyl)-benzyl]-4-oxo-1-phenyl-1,4-dihydroquinoline-2-carboxylic acid methyl ester (compound 87)

Step A: To 4-formylbenzenesulfonyl chloride (1.0 g) in MeOH (10 mL) was added $NaHCO_3$ (0.425 g, s), followed by S-(−)-3-hydroxypyrrolidine (0.533 g), and the mixture stirred at RT for 1 h. The product was filtered through celite, concentrated to provide an oil, and chromatographed on silica (3% MeOH/DCM) to provide 4-(3-hydroxypyrrolidine-1-sulfonyl)-benzaldehyde (1.14 g).

Step B: To 1-(4-chloro-2-phenylamino-phenyl)ethanone (0.500 g) and 4-(3-hydroxypyrrolidine-1-sulfonyl)-benzaldehyde (0.519 g) in MeOH (10 mL) was added NaOH (1.68 mL, 2 N aq), and the mixture stirred overnight at RT. The red-orange product crashed out of solution, and was collected on a sintered glass funnel, rinsed with water, and taken up in MeOH. The produce was concentrated, then chromatographed on anhydrous silica (100% DCM 0-10 min; 2% MeOH/DCM 11-30 min) to provide 1-(4-chloro-2-phenylamino-phenyl)-3-[4-(3-hydroxypyrrolidine-1-sulfonyl)-phenyl]-propenone (0.588 g).

Step C: Proceeding as described in Example 13, Step C, 1-(4-chloro-2-phenylamino-phenyl)-3-[4-(3-hydroxypyrrolidine-1-sulfonyl)-phenyl]-propenone was hydrogenated to produce 1-(4-chloro-2-phenylamino-phenyl)-3-[4-(3-hydroxypyrrolidine-1-sulfonyl)phenyl]-propan-1-one as a yellow, oily solid.

Step D: To 1-(4-chloro-2-phenylamino-phenyl)-3-[4-(3-hydroxypyrrolidine-1-sulfonyl)-phenyl]-propan-1-one (0.150 g) in toluene was added methyl oxalyl chloride (0.6 mL). The reaction mixture was heated to 80° C. for 3 h, then stirred overnight at RT to produce N-(5-chloro-2-{3-[4-(2-hydroxypyroolidine-1-sulfonyl)phenyl]propionyl}-phenyl)-N-phenyl-oxalamic acid methyl ester, which was used without further purification.

Step E: Following the procedure set forth in Example 14, Step B, N-(5-chloro-2-{3-[4-(2-hydroxypyroolidine-1-sulfonyl)phenyl]propionyl}-phenyl)-N-phenyl-oxalamic acid methyl ester was cyclized to form 7-chloro-3-[4-(3-hydroxypyrrolidine-1-sulfonyl)-benzyl]-4-oxo-1-phenyl-1,4-dihydroquinoline-2-carboxylic acid methyl ester (compound 87). The product was chromatographed on anhydrous silica (3% MeOH/DCM 0-10 min; 10% MeOH/DCM 11-20 min), then re-chromatographed on pure silica with 5% MeOH/DCM. M+H 553; mp=135.0-136.0° C.

Example 17

Synthesis of 2-Acetyl-7-chloro-3-[4-(4-hydroxypiperidine-1-sulfonyl)-benzyl]-1-phenyl-1H-quinolin-4-one (compound 70)

Step A: To 1-(4-chloro-2-phenylamino-phenyl)-3-[4-(4-hydroxypiperidine-1-sulfonyl)-phenyl]propan-1-one (0.200 g) in toluene (20 mL) was added 2-oxopropanoyl chloride (0.427 g). The reaction mixture was heated at 120° C. for 3 h, then stirred at RT overnight to produce N-(5-chloro-2-{3-[4-(4-hydroxypiperidine-1-sulfonyl)-phenyl]-propionyl}-phenyl)-2-oxo-N-phenyl-propionamide, which was used without further purification.

Step B: To N-(5-chloro-2-{3-[4-(4-hydroxypiperidine-1-sulfonyl)-phenyl]-propionyl}-phenyl)-2-oxo-N-phenyl-propionamide in MeOH was added $K_2CO_3$ (0.096 g), and the mixture heated at 80° C. for 1.5 h, then concentrated. The residue was taken up in EtOAc/$H_2O$, and the aqueous layer washed with EtOAc (2×25 mL). The combined organic layers were dried over $Na_2SO_4$, and the solvent removed under reduced pressure. The residue was chromatographed on anhydrous silica (20% EtOAc/hexanes 0-5 min; 60% EtOAc/hexanes 15-20 min; 100% EtOAc 22-35 min) to provide 2-acetyl-7-chloro-3-[4-(4-hydroxypiperidine-1-sulfonyl)-benzyl]-1-phenyl-1H-quinolin-4-one (compound 70). Mp=145.5-147.2° C.; M+H 551.

Similarly, proceeding as set forth above and substituting the appropriate reactants, the compound 2-acetyl-7-chloro-3-[4-(4-methylpiperazine-1-sulfonyl)-benzyl]-1-phenyl-1H-quinolin-4-one (compound 72, mp=206.3-208.0° C.; M+H 550) was prepared.

Example 18

Synthesis of 3-(6-chloro-pyridin-3-ylmethyl)-7-methyl-4-oxo-1-phenyl-1,4-dihydro[1,8]naphthyridine-2-carboxylic acid methyl ester (compound 83)

Step A: A solution of 2-chloro-3-acetyl-6-methylpyridine (6.0 g) in 1,4-dioxane (60 mL) was combined with camphor sulfonic acid (20.7 g) and allowed to stir in a sealed tube until homogenous. The mixture was heated to 70° C., aniline (5.0 g) was added, and heating continued until all precipitating solids redissolved. Progress of the reaction was monitored by quenching samples in EtOAc/$NaHCO_3$ (sat'd aq) and examining by TLC (1:2 EtOAc/hexane). The reaction was complete after 1.5 h, and was quenched by with EtOAc/$NaHCO_3$ (sat'd aq), stirring until gas evolution ceased. The organic layer was washed with $NaHCO_3$ (sat'd aq), filtered, concentrated, and chromatographed on silica (1:4 EtOAc/hexane) to provide 2-phenylamino-3-acetyl-6-pyridine (6.2 g) as a yellow solid. M+H=227.

Step B: 2-Phenylamino-3-acetyl-6-pyridine (1.0 g) was dissolved in MeOH (20 mL) using a sonicator, followed by 2-chloro-5-formylpyridine (1.1 g) and NaOH (2 M, 3.5 mL). The mixture was allowed to stir at RT, forming a red precipitate. The product was filtered, washed with MeOH/$H_2O$ (2:1, 10 mL), and dried under vacuum to yield 1-(6-methyl-2-phenylamino-pyridin-3-yl)-3-(6-chloropyridin-3-yl)-propenone (1.45 g) as an orange/red solid. M+H=350.

Step C: To a solution of 1-(6-methyl-2-phenylaminopyridin-3-yl)-3-(6-chloropyridin-3-yl)-propenone (1.15 g) in warm EtOAc (40 mL) was added $PtO_2$ (0.04 g), after which the vessel was evacuated and filled with $H_2$ (2×) at balloon pressure. The reaction mixture was heated at 60° C. for 2.5 h, then cooled to RT, filtered through celite, washed with THF/EtOH, concentrated, and chromatographed on silica (EtOAc/hexane 1:1) to provide 1-(6-methyl-2-phenylamino-pyridin-3-yl)-3-(6-chloropyridin-3-yl)-propan-1-one (1.0 g) as a yellow solid. M+H=352.

Step D: To a solution of 1-(6-methyl-2-phenylaminopyridin-3-yl)-3-(6-chloropyridin-3-yl)-propan-1-one (0.9 g) in toluene (5 mL) and THF (10 mL) was added methyl oxalyl chloride (0.56 g), and the mixture heated to 80° C. for 2.5 h. The product was concentrated to a dark red solution of N-{-3-[3-(6-chloropyridin-3-yl)-propionyl]-6-methyl-pyridin-2-yl}-N-phenyl-oxalamic acid methyl ester in toluene, which was used without further purification.

Step E: To a solution of N-{-3-[3-(6-chloropyridin-3-yl)-propionyl]-6-methyl-pyridin-2-yl}-N-phenyl-oxalamic acid methyl ester in toluene was added MeOH, and the mixture placed in a pre-heated hot bath at 80° C. $K_2CO_3$ (0.9 g) was added, which produced an immediate color change. The mixture was cooled to RT, diluted with EtOAc, and washed with LiCl (0.3 wt % aq, 2×). The organic layer was dried over $MgSO_4$, filtered, and concentrated. The product was dissolved in hot EtOAc, and allowed to cool to RT. The resulting precipitate was filtered and washed with EtOAc to provide 3-(6-chloro-pyridin-3-ylmethyl)-7-methyl-4-oxo-1-phenyl-1,4-dihydro[1,8]naphthyridine-2-carboxylic acid methyl ester (compound 83) (0.14 g) as a tan solid. M+H=420, mp=220.0-220.5.

Example 19

Synthesis of 3-(Pyridin-3-ylmethyl)-7-methyl-4-oxo-1-phenyl-1,4-dihydro[1,8]-naphthyridine-2-carboxylic Acid Methyl Ester (Compound 84)

Step A: 1-(6-Methyl-2-phenylaminopyridin-3-yl)-3-(6-chloropyridin-3-yl)-propenone (0.30 g) was added to EtOH (3 mL), followed by THF (6 mL), toluene (6 mL), additional EtOH (about 2 mL), and Pd/C (10%, 0.02 g). The vessel was evacuated, then backfilled with $H_2$ (2×), aged for 1 h at RT, then at 60° C. for 3 h. The mixture was allowed to cool to RT overnight, then an additional aliquot of Pd/C (10%, 0.02 g) added, the mixture heated to 75° C. for 8 h, then allowed to cool to RT overnight. The product was filtered through celite, washed with EtOH, concentrated, and chromatographed on silica (1:1 EtOAc/hex to 5% MeOH/EtOAc/hex) to provide 1-(6-methyl-2-phenylamino-pyridin-3-yl)-3-pyridin-3-yl-propan-1-one (0.14 g) as a yellow oil. M+H=318.

Step B: Proceeding as set forth in Example 18, Steps D and E, the compound 3-(pyridin-3-ylmethyl)-7-methyl-4-oxo-1-phenyl-1,4-dihydro[1,8]naphthyridine-2-carboxylic acid methyl ester (compound 84) (28 mg) was produced. M+H=386.

Example 20

Synthesis of 3-(6-Methoxycarbonyl-pyridin-3-ylmethyl)-7-methyl-4-oxo-1-phenyl-1,4-dihydro[1,8]naphthyridine-2-carboxylic Acid Methyl Ester (Compound 100)

Step A: A mixture of 1-(6-methyl-2-phenylaminopyridin-3-yl)-3-(6-chloropyridin-3-yl)-propan-1-one (1.9 g), $Et_3N$ (1.0 mL), MeOH (30 mL), and (R-BINAP)$PdCl_2$ (43 mg) was placed in a bomb. The bomb was then purged of air, pressurized to 50 psi with carbon monoxide, and heated to 100° C. for 3.25 h. The bomb was then cooled to 50° C., opened, and allowed to cool to RT. The solid product was taken up in DCM, and crystallized from DCM/MeOH to provide 5-[3-(6-methyl-2-phenylamino-pyridin-3-yl)-3-oxo-propyl]-pyridine-2-carboxylic acid methyl ester (1.7 g) as a yellow solid. M+H=376.

Step B: 5-[3-(6-Methyl-2-phenylamino-pyridin-3-yl)-3-oxo-propyl]-pyridine-2-carboxylic acid methyl ester (1.7 g) was dissolved in toluene (15 mL) and THF (30 mL) under $N_2$ at 80° C. Monomethyl oxalyl chloride (2.2 g) was added, and the mixture heated at 80° C. for 3.5 h, turning a dark red/black color. The mixture was cooled to RT and concentrated to a solid, then dissolved in MeOH and heated again to 80° C. $K_2CO_3$ (0.8 g) was added, the mixture heated at 80° C. for 30 min, an additional portion of $K_2CO_3$ (0.8 g) was added, and the mixture heated another 1 h. The product was taken up in EtOAc and $H_2O$, the organic phase washed with $H_2O$ (1×), dried over $MgSO_4$, filtered, concentrated, and chromatographed on silica (2:3 EtOAc/hexane to 100% EtOAc) to provide 3-(6-methoxycarbonyl-pyridin-3-ylmethyl)-7-methyl-4-oxo-1-phenyl-1,4-dihydro[1,8]naphthyridine-2-carboxylic acid methyl ester (compound 100) (0.38 g) as a yellow solid. M+H=444, mp=177.0-178.0° C.

Example 21

Synthesis of 3-(6-Methanesulfonyl-pyridin-3-ylmethyl)-7-methyl-4-oxo-1-phenyl-1,4-dihydro[1,8]naphthyridine-2-carboxylic Acid Methyl Ester (Compound 92)

Step A: 1-(6-Methyl-2-phenylaminopyridin-3-yl)-3-(6-chloropyridin-3-yl)-propan-1-one (0.42 g) was dissolved in NMP (3 mL), NaSMe (0.34 g) added, and the mixture heated at 150° C. in a microwave for 1 h. The product was taken up in EtOAc/$H_2O$, the organic layer washed with LiCl (2×, 0.3 wt % aq), dried over $MgSO_4$, filtered, and concentrated to a red oil to provide 3-(6-mercaptopyridin-3-yl)-1-(6-methyl-2-phenylaminopyridin-3-yl)-propan-1-one (0.4 g).

Step B: 3-(6-Mercaptopyridin-3-yl)-1-(6-methyl-2-phenylaminopyridin-3-yl)-propan-1-one (0.4 g) was dissolved in DMF (5 mL), and methyl iodide (0.05 mL) added, followed by $K_2CO_3$ (0.138 g). The reaction mixture was allowed to stand at RT for 2.5 h, then worked up in EtOAc/$H_2O$. The organic layer was washed with LiCl (2×, 0.3 wt % aq), dried over $MgSO_4$, filtered, concentrated, and chromatographed over silica (12 g, 1:2 EtOAc/hexane) to provide 1-(6-methyl-2-phenylamino-pyridin-3-yl)-3-(6-methylsulfanyl-pyridin-3-yl)-propan-1-one (0.23 g). M+H=264.

Step C: 1-(6-Methyl-2-phenylamino-pyridin-3-yl)-3-(6-methylsulfanyl-pyridin-3-yl)-propan-1-one (0.23 g) was dissolved in DMF (5 mL), and Oxone (0.32 g) added. The mixture was stirred at RT overnight. A small additional amount of Oxone was added, and the mixture stirred an additional 3 h, then worked up with EtOAc/$H_2O$, the organic layer washed with LiCl (2×, 0.3 wt % aq), dried over $MgSO_4$, and concentrated to provide a 2:1 mixture of 1-(6-methyl-2-phenylamino-pyridin-3-yl)-3-(6-methylsulfonyl-pyridin-3-yl)-propan-1-one and 1-(6-methyl-2-phenylamino-pyridin-3-yl)-3-(6-methylsulfinyl-pyridin-3-yl)-propan-1-one (0.22 g) as a red-orange oil, which was used without separation. M+H=396 (sulfonyl) and 380 (sulfinyl).

Step D: A 2:1 mixture of 1-(6-methyl-2-phenylamino-pyridin-3-yl)-3-(6-methylsulfonyl-pyridin-3-yl)-propan-1-one and 1-(6-methyl-2-phenylamino-pyridin-3-yl)-3-(6-methylsulfinyl-pyridin-3-yl)-propan-1-one (0.22 g) was dissolved in THF (3 mL) and toluene (1.5 mL), and monomethyl oxalyl chloride (0.27 g) added. The mixture was heated to 80° C. for 2.5 h, concentrated to a semi-solid, taken up in MeOH, and $K_2CO_3$ (0.22 g) added. This mixture was heated to 80° C. for 15 min, then cooled to RT. The product was worked up in EtOAc/$H_2O$, the organic layer washed with LiCl (2×, 0.3 wt % aq), dried over $MgSO_4$, and purified by prep TLC (1:1 EtOAc/hexane) to provide 3-(6-methanesulfonyl-pyridin-3-ylmethyl)-7-methyl-4-oxo-1-phenyl-1,4-dihydro[1,8]naphthyridine-2-carboxylic acid methyl ester (compound 92) (8 mg) as a yellow solid. M+H=464, mp=217-218° C.

Example 22

Synthesis of 3-(6-methanesulfanyl-pyridin-3-ylmethyl)-7-methyl-4-oxo-1-phenyl-1,4-dihydro[1,8]naphthyridine-2-carboxylic Acid Methyl Ester (Compound 94)

Step A: Proceeding as set forth in Example 21, Step D, 1-(6-methyl-2-phenylamino-pyridin-3-yl)-3-(6-methylsulfanyl-pyridin-3-yl)-propan-1-one (0.2 g) was reacted with methyl oxalyl chloride (0.27 g) and $K_2CO_3$ (0.2 g) in toluene (2 mL) and THF (4 mL) to form 3-(6-methanesulfanyl-pyridin-3-ylmethyl)-7-methyl-4-oxo-1-phenyl-1,4-dihydro[1,8]naphthyridine-2-carboxylic acid methyl ester (compound 94) (0.12 g). M+H=432, mp=185.0-186.5° C.

Example 23

Synthesis of 3-(6-methanesulfinylpyridin-3-ylmethyl)-7-methyl-4-oxo-1-phenyl-1,4-dihydro[1,8]naphthyridine-2-carboxylic Acid Methyl Ester (Compound 98)

Step A: Compound 94 (0.12 g) was dissolved in DMF (5 mL), Oxone (0.14 g) added, and the mixture stirred for 30 min. The product was separated between EtOAc and $H_2O$, the organic layer washed with LiCl (2×, 0.3 wt % aq), dried over $MgSO_4$, and purified by prep TLC (1:1 EtOAc/hexane) to provide 3-(6-methanesulfinyl-pyridin-3-ylmethyl)-7-methyl-4-oxo-1-phenyl-1,4-dihydro[1,8]naphthyridine-2-carboxylic acid methyl ester (compound 98) (5 mg) as a yellow solid. M+H=448.

Example 24

Synthesis of 3-(6-Dimethylcarbamoyl-pyridin-3-ylmethyl)-7-methyl-4-oxo-1-phenyl-1,4-dihydro[1,8]naphthyridine-2-carboxylic Acid Methyl Ester (Compound 103)

Step A: To 3-(6-methoxycarbonyl-pyridin-3-ylmethyl)-7-methyl-4-oxo-1-phenyl-1,4-dihydro[1,8]naphthyridine-2-carboxylic acid methyl ester (compound 100) (0.2 g) in THF (10 mL) was added LiOH.$H_2O$ (0.06 g) and $H_2O$ (2 mL), and the mixture stirred at RT for 1 h. The product was taken up in EtOAc, washed with $H_2O$ and HCl (2M, 2 mL), filtered, and worked up with EtOAc and $H_2O$. The organic layer was dried over $MgSO_4$, and concentrated to a yellow oil. The oil was taken up in EtOAc, washed with $H_2O$, dried over $MgSO_4$, and concentrated to a yellow solid to provide 3-(6-carboxy-pyridin-3-ylmethyl)-7-methyl-4-oxo-1-phenyl-1,4-dihydro[1,8]naphthyridine-2-carboxylic acid methyl ester (0.11 g). M+H=430.

Step B: To 3-(6-carboxy-pyridin-3-ylmethyl)-7-methyl-4-oxo-1-phenyl-1,4-dihydro-[1,8]naphthyridine-2-carboxylic acid methyl ester (0.095 g) in THF (6 mL) was added BOP (0.11 g), followed by DMA (0.15 mL, 2M in THF) and Hunig's Base (ethyl-diisopropylamine) (0.042 mL). Solids began to precipitate: DCM was added until all solids dissolved, and a homogenous reaction mixture was obtained. The mixture was stirred at RT for 1 h, then an additional aliquot of BOP, Hunig's base, and DMA added, and the mixture stirred at RT overnight. The product was worked up with EtOAc and $H_2O$, washed with $NaHCO_3$ (aq) and $H_2O$, and dried over MgSO$_4$. The product was concentrated, applied to a silica gel column with EtOAc, and eluted with EtOAc/MeOH, and concentrated to yield 3-(6-dimethylcarbamoyl-pyridin-3-ylmethyl)-7-methyl-4-oxo-1-phenyl-1,4-dihydro[1,8]naphthyridine-2-carboxylic acid methyl ester (compound 103) (80 mg) as a pale yellow solid. M+H=457; mp=235.0-236.0° C.

Example 25

Synthesis of 3-(6-Ethylcarbamoyl-pyridin-3-ylmethyl)-7-methyl-4-oxo-1-phenyl-1,4-dihydro[1,8]naphthyridine-2-carboxylic Acid Methyl Ester (Compound 101)

To 3-(6-carboxy-pyridin-3-ylmethyl)-7-methyl-4-oxo-1-phenyl-1,4-dihydro[1,8]-naphthyridine-2-carboxylic acid methyl ester (0.11 g) in DCM was added BOP (0.14 g), followed by ethylamine (0.016 g) and Hunig's Base (0.06 mL), and the mixture stirred at RT overnight. The product was taken up in EtOAc and H$_2$O, washed with NaHCO$_3$ (aq), and dried over MgSO$_4$, then filtered, concentrated, and purified by prep TLC using 100% EtOAc, to provide 3-(6-ethylcarbamoyl-pyridin-3-ylmethyl)-7-methyl-4-oxo-1-phenyl-1,4-dihydro[1,8]-naphthyridine-2-carboxylic acid methyl ester (compound 101) as an off-white solid. M+H=457.

Example 26

Synthesis of 3-(6-Methoxypyridin-3-ylmethyl)-7-methyl-4-oxo-1-phenyl-1,4-dihydro[1,8]naphthridine-2-carboxylic Acid Methyl Ester (Compound 102)

Step A: To 1-(6-methyl-2-phenylaminopyridin-3-yl)-ethanone (0.5 g) in MeOH (12 mL) was added 6-methoxy-3-pyridine carboxaldehyde (0.5 g), followed by NaOH (2 M, 1.75 mL), and the mixture stirred at RT overnight. The solid that precipitated was filtered, washed with MeOH, and dried under vacuum to yield 3-(6-methoxy-pyridin-3-yl)-1-(6-methyl-2-phenyl-amino-pyridin-3-yl)-propenone (0.71 g) as a bright saffron-yellow solid. M+H=346.

Step B: To 3-(6-methoxy-pyridin-3-yl)-1-(6-methyl-2-phenylamino-pyridin-3-yl)-propenone (0.71 g) in THF (20 mL) and EtOH (10 mL) was added a small quantity of Pd/C (10 mL). The flask was evacuated, backfilled with H$_2$ twice, and allowed to stir overnight at RT. The product was filtered through Celite, washed with EtOH, concentrated, eluted from a silica gel column with 30:70 EtOAc/hexane. The product-containing fractions were collected and concentrated to yield 3-(6-methoxy-pyridin-3-yl)-1-(6-methyl-2-phenylamino-pyridin-3-yl)-propan-1-one (0.70 g) as a pale yellow solid. M+H=348.

Step C: To 3-(6-methoxy-pyridin-3-yl)-1-(6-methyl-2-phenylamino-pyridin-3-yl)-propan-1-one (0.70 g) in THF and toluene was added methyl oxalyl chloride (0.99 g), followed by TEA (0.5 mL) to solubilize the solids that crashed out of solution. The resulting slurry was heated at 80° C. for 3 h, then concentrated and resuspended in MeOH. K$_2$CO$_3$ (0.70 g) was added, and the mixture stirred at 80° C. for 30 min. The product was worked up with EtOAc and H$_2$O, and concentrated to a yellow solid. The solid was taken up in MeOH, heated to 70° C., an additional aliquot of K$_2$CO$_3$ (0.70 g) added, and the mixture stirred for 90 min. The product was worked up with EtOAc and H$_2$O, concentrated, dried over MgSO$_4$, eluted from a silica gel column (30:70 EtOAc/hexane), and concentrated to provide 3-(6-methoxypyridin-3-ylmethyl)-7-methyl-4-oxo-1-phenyl-1,4-dihydro[1,8]naphthridine-2-carboxylic acid methyl ester (compound 102) (140 mg) as a yellow solid. M+H=416; mp=176.0-177.0° C.

Example 27

Synthesis of 7-fluoro-3-(4-methanesulfonyl-piperidin-1-ylmethyl)-4-oxo-1-phenyl-1,4-dihydro-quinoline-2-carboxylic acid methyl ester (Compound 126)

Step A: 2-Bromo-4-fluorobenzoic acid (20 g), aniline (10.2 g), K$_2$CO$_3$ (13.9 g), Cu(I) oxide (Aldrich 20822, 648 mg) and Cu powder (3 t, 560 mg) were combined in ethoxyethanol (30 mL) and heated at reflux (130-135° C.) for 4 h under N$_2$. The reaction was judged complete by LCMS and TLC. The mixture was cooled to RT, diluted with H$_2$O (30 mL), and neutralized to pH 7 with conc. HCl, forming a precipitate. The product was filtered, washed with H$_2$O, and dried at 55° C. for 3 d in a vacuum oven to provide 4-fluoro-2-phenylamino-benzoic acid (17.7 g).

Step B: 4-Fluoro-2-phenylamino-benzoic acid (17.7 g) was dissolved in DMF (100 mL), and stirred with 1,1'-carbonyldiimidazole (14.91 g) under N$_2$ at 60° C. for 30 min. N,O-dimethylhydroxylamine hydrochloride (8.97 g) was added, and stirring continued at 60° C. for 4 h. The DMF was then removed under high vacuum, and the black residue partitioned into EtOAc and brine, and chromatographed (EtOAc/hexane) to yield 4-fluoro-N-methoxy-N-methyl-2-phenyl-amino-benzamide (11 g).

Step C: 4-Fluoro-N-methoxy-N-methyl-2-phenylamino-benzamide (12.5 g) was dissolved in THF (100 mL) at 0° C., and vinyl-MgBr (84 mL, 1 M in THF) added slowly. The mixture was stirred for 2 h at 0° C., then quenched with HCl (0.5 M, 200 mL). The product was extracted with EtOAc, and chromatographed with EtOAc/hexane (10-80%) to provide 1-(4-fluoro-2-phenylamino-phenyl)-propenone (4.0 g) as a yellow oil.

Step D: To a solution of 1-(4-fluoro-2-phenylamino-phenyl)-propenone (400 mg) in EtOH (8 mL) was added K$_2$CO$_3$ (~150 mg) and 4-methylsulfonylpiperidine (326 mg). The mixture was stirred for 24 h, diluted with EtOAc, and filtered. The product was recovered by chromatography (0-30% MeOH/DCM) to provide 1-(4-fluoro-2-phenylamino-phenyl)-3-(4-methanesulfonyl-piperidin-1-yl)-propan-1-one (598 mg) as a yellow solid.

Step E: To a 0° C. solution of 1-(4-fluoro-2-phenylamino-phenyl)-3-(4-methanesulfonyl-piperidin-1-yl)-propan-1-one (500 mg) in THF (8 mL) under N$_2$ was added NaHMDS (3.1 mL, 1 M in THF). After 5 min, chloro-oxoacetic acid methyl ester (0.28 mL) was added, and the mixture stirred for 2 h at 0° C., then for 1 h at RT. The reaction mixture was quenched with NH$_4$Cl (sat'd aq), extracted with EtOAc, and chromatographed (0-20% MeOH/DCM) to provide 7-fluoro-3-(4-methanesulfonyl-piperidin-1-ylmethyl)-4-oxo-1-phenyl-1,4-dihydro-quinoline-2-carboxylic acid methyl ester (301 mg, Compound 126). M+H=473; mp=190.0-191.0° C.

Example 28

Synthesis of 3-Benzyl-7-fluoro-4-oxo-1-phenyl-1,4-dihydro-quinoline-2-carboxylic acid 2-methoxyethyl ester (Compound 130)

Step A: To a 0° C. solution of 4-fluoro-N-methoxy-N-methyl-2-phenylamino-benzamide (10 g) in THF (80 mL) was slowly added phenethyl-MgBr (91.2 mL, 1 M in THF), and the mixture stirred at 0° C. for 30 min, followed by 1 h at RT. The reaction mixture was then quenched with NH₄Cl (sat'd aq), extracted with EtOAc, and chromatographed (0-40% EtOAc/DCM) to provide 1-(4-fluoro-2-phenylamino-phenyl)-3-phenyl-propan-1-one (11.34 g) as a yellow solid.

Step B: To a solution of {[5-fluoro-2-(3-phenyl-propionyl)-phenyl]-phenyl-amino}-oxo-acetyl chloride (540 mg) in THF (3 mL) was added 2-methoxyethanol (0.12 mL), followed by Et₃N (0.22 mL). The reaction mixture became a pale yellow slurry: additional THF (2 mL) was added, and the mixture allowed to stand for 1 h. The mixture was then quenched with NH₄Cl (sat'd aq), extracted with EtOAc, washed with brine, and concentrated to yield N-[5-fluoro-2-(3-phenyl-propionyl)-phenyl]-N-phenyl-oxalamic acid 2-methoxy-ethyl ester (504 mg) as an oil.

Step C: To a solution of N-[5-fluoro-2-(3-phenyl-propionyl)-phenyl]-N-phenyl-oxalamic acid 2-methoxy-ethyl ester (500 mg) in MeOH (10 mL) was added K₂CO₃ (~150 mg), and the reaction mixture heated at reflux under N₂ for 1.5 h. The mixture was then cooled, the salts filtered, and solvent evaporated in vacuo. The residue was chromatographed (0-20% MeOH/DCM) to provide 3-benzyl-7-fluoro-4-oxo-1-phenyl-1,4-dihydro-quinoline-2-carboxylic acid 2-methoxy-ethyl ester (Compound 130). M+H=432; mp=168.0-169.0° C.

Example 29

Synthesis of 3-benzyl-7-chloro-2-oxazol-2-yl-1-phenyl-1H-quinolin-4-one (Compound 140)

Step A: Oxazole-2-carboxylic acid (0.5 g) was suspended in DCM (15. mL), and 2 drops of DMF were added under N₂. Oxalyl chloride (674 mg) was added slowly, and the reaction mixture was stirred until bubbling ceased (about 2 h). The solvent was removed in vacuo, and the residue taken up in toluene (15 mL). 1-(4-Chloro-2-phenylamino-phenyl)-3-phenyl-propan-1-one (1.48 g) was added, and the mixture heated at reflux for 20 h. The product was cooled, the solvent removed in vacuo, and the residue chromatographed (0-20% MeOH:DCM) to provide oxazole-2-carboxylic acid [5-chloro-2-(3-phenyl-propionyl)-phenyl]-phenyl-amide (697 mg) as a pale yellow powder.

Step B: Oxazole-2-carboxylic acid [5-chloro-2-(3-phenyl-propionyl)-phenyl]-phenyl-amide (387 mg) was dissolved in dry MeOH (20 mL) and K₂CO₃ (100 mg), and heated at reflux for 1.5 h. The product was then cooled, the solvent evaporated, and the residue chromatographed (0-30% MeOH/DCM) to provide 3-benzyl-7-chloro-2-oxazol-2-yl-1-phenyl-1H-quinolin-4-one (Compound 140, 233 mg). mp=219.0-220.0° C.

Example 30

Synthesis of 3-(1-methyl-1H-pyrazol-4-ylmethyl)-1-phenyl-7-trifluoromethyl-1H-[1,8]naphthyridin-4-one (Compound 129)

Step A: 1-(2-Phenylamino-6-trifluoromethyl-pyridin-3-yl)-ethanone (0.1 g) was mixed with 1-methyl-1H-pyrazole-4-carbaldehyde (39 mg) and NaNH₂ (2 N, 2 mL) in MeOH (10 mL) and stirred overnight at RT. The light orange solid that formed was filtered, and dried in a vacuum oven to provide 3-(1-methyl-1H-pyrazol-4-yl)-1-(2-phenylamino-6-trifluoromethyl-pyridin-3-yl)-propenone (45 mg).

Step B: 3-(1-methyl-1H-pyrazol-4-yl)-1-(2-phenylamino-6-trifluoromethyl-pyridin-3-yl)-propenone (45 mg) was dissolved in EtOAc (25 mL), Pd/C (10%, 30 mg) added, and the starting material hydrogenated with H₂ (balloon) for 1 h. The product, 3-(1-methyl-1H-pyrazol-4-yl)-1-(2-phenylamino-6-trifluoromethyl-pyridin-3-yl)-propan-1-one, was filtered, concentrated, and used without further purification.

Step C: 3-(1-Methyl-1H-pyrazol-4-yl)-1-(2-phenylamino-6-trifluoromethyl-pyridin-3-yl)-propan-1-one (~45 mg) was dissolved in toluene (10 mL) with chloro-oxo-acetic acid methyl ester (0.2 mL) and heated at 110° C. for 72 h, then cooled. The product was concentrated in vacuo, then dissolved in MeOH (10 mL) with K₂CO₃ (0.2 g), and heated to 50° C. for 15 min. The product was cooled, filtered, and concentrated to provide 3-(1-methyl-1H-pyrazol-4-ylmethyl)-1-4-oxo-phenyl-7-trifluoromethyl-1H-[1,8]naphthyridine-2-carboxylic acid methyl ester (Compound 129). M+H=443.

Example 31

Synthesis of 1-(3-aminophenyl)-3-benzyl-7-methyl-4-oxo-1,4-dihydro[1,8]-naphthyridine-2-carboxylic acid methyl ester (Compound 105)

Step A: 1-(2-Chloro-6-methyl-pyridin-3-yl)-ethanone (0.4 g) was mixed with 3-nitro-phenylamine (0.33 g), Pd(OAc)₂ (16 mg), BINAP (45 mg), CaCO₃ (0.25 g), and Et₃N (0.2 mL) in toluene (10 mL), and heated at 100° C. for 4 d. The product was then filtered and concentrated to provide 1-[6-methyl-2-(3-nitrophenylamino)-pyridin-3-yl]-ethanone (0.2 g).

Step B: 1-[6-Methyl-2-(3-nitrophenylamino)-pyridin-3-yl]-ethanone (0.2 g) was mixed with 4-methanesulfonyl-benzaldehyde (0.135 g) and NaNH₂ (2 N, 2 mL) in MeOH (10 mL), and stirred overnight at RT. The yellow solid that formed was filtered to provide 3-(4-methanesulfonyl-phenyl)-1-[6-methyl-2-(3-nitrophenylamino)-pyridin-3-yl]-propenone (0.33 g).

Step C: 3-(4-Methanesulfonyl-phenyl)-1-[6-methyl-2-(3-nitrophenylamino)-pyridin-3-yl]-propenone (125 mg) was hydrogenated with RhCl(PPh₃)₃ (30 mg) in toluene (20 mL) using H₂ at 66 psi, at 60° C. for 7 h, to provide 3-(4-methanesulfonyl-phenyl)-1-[6-methyl-2-(3-nitrophenylamino)-pyridin-3-yl]-propan-1-one (~100 mg).

Step D: 3-(4-Methanesulfonyl-phenyl)-1-[6-methyl-2-(3-nitrophenylamino)-pyridin-3-yl]-propan-1-one (0.1 g) was dissolved in THF (5 mL). Chloro-oxo-acetic acid methyl ester (0.1 mL) was added, and the mixture heated by microwave at 80° C. for 1 h. The product was concentrated, the residue taken up in MeOH (5 mL), K₂CO₃ (0.1 g) added, and the mixture heated at 50° C. for 15 min. The product was cooled and concentrated, and purified by prep TLC (50% EtOAc/hexane) to provide 3-benzyl-7-methyl-1-(3-nitrophenyl)-4-oxo-1,4-dihydro[1,8]-naphthyridine-2-carboxylic acid methyl ester (Compound 104, ~20 mg). M+H=508.

Step E: Compound 104 (15 mg) was dissolved in EtOAc (10 mL) with Pc/C (10%, 5 mg), and hydrogenated using H2 (balloon) for 2 h. The product was filtered, concentrated, and purified by prep TLC (50/50 EtOAc/hexane), then 10% MeOH/DCM to provide 1-(3-amino-phenyl)-3-benzyl-7-methyl-4-oxo-1,4-dihydro[1,8]naphthyridine-2-carboxylic acid methyl ester (Compound 105, 2.4 mg). M+H=478.

Example 32

Synthesis of 1-(6-amino-pyridin-2-yl)-3-benzyl-7-chloro-2-oxazol-2-yl-1H-quinolin-4-one (Compound 141)

Step A: A mixture of 2-bromo-4-chlorobenzoic acid (5 g), 2,6-diaminopyridine (6.95 g), K₂CO₃ (3.18 g), Cu powder (0.13 g) and Cu(I) oxide (0.15 g) in ethoxyethanol (10 mL) was heated at 130° C. for 2 h, until the reaction was complete (as confirmed by tlc). The mixture was cooled to RT, and water (70 mL) and activated carbon was added, and the mixture stirred for 3 h. The product was then filtered, and HCl (4 M) was added until pH 7 was reached. The resulting brown precipitate was filtered and dried in an oven (50° C., pressure=30 mbar) overnight to provide 2-(6-amino-pyridin-2-ylamino)-4-chlorobenzoic acid (2.4 g).

Step B: A slurry of 2-(6-amino-pyridin-2-ylamino)-4-chlorobenzoic acid (2.4 g) and 2,5-hexanedione (1.04 g) and p-toluenesulfonic acid (0.15 g) was heated at reflux in a Dean-Stark trap for 24 h. The resulting mixture was cooled to RT and filtered, then stirred with $H_2O$ (50 mL) overnight, filtered, and dried to yield 4-chloro-2-[6-(2,5-dimethyl-pyrrol-1-yl)-pyridin-2-ylamino]-benzoic acid (2.4 g).

Step C: A mixture of 4-chloro-2-[6-(2,5-dimethyl-pyrrol-1-yl)-pyridin-2-ylamino]-benzoic acid (4.2 g) in DMF (25 mL) and carbonyldiimide (2.4 g) was stirred at 60° C. for 30 min, and N-methoxy-N-methylamine (1.41 g) was added. The mixture was stirred at 80° C. for 16 h, then the volatiles evaporated, and the residue partitioned between EtOAc and $H_2O$, then between EtOAc and HCl (0.1 N aq). The organic phase was adsorbed on silica gel and chromatographed. Chromatography on silica (80 g) against hexane/EtOAc (100:0 to 50:50) provided 4-chloro-2-[6-(2,5-dimethyl-pyrrol-1-yl)-pyridin-2-ylamino]-N-methoxy-N-methyl-benzamide (~1.6 g).

Step D: A solution of 4-chloro-2-[6-(2,5-dimethyl-pyrrol-1-yl)-pyridin-2-ylamino]-N-methoxy-N-methyl-benzamide (1.59 g) in THF (20 mL) was cooled in an ice bath, and phenethyl-Grignard solution (10 mL, 1 M in THF) added via syringe. The mixture was stirred overnight at RT, quenched with $NH_4Cl$ (aq), extracted with EtOAc, and adsorbed on silica. The product was chromatographed on silica (80 g) (hexane/EtOAc 100:0 to 50:50) (or using DCM/MeOH) to provide 1-{4-chloro-2-[6-(2,5-dimethyl-pyrrol-1-yl)-pyridin-2-ylamino]-phenyl}-3-phenyl-propan-1-one.

Step E: A mixture of oxazole-2-carboxylic acid (147 mg) and DMF (2 drops) in DCM (1 mL) was treated with oxalyl chloride (127 μL). Gas evolution ceased after 2 h. $CHCl_3$ (2 mL) was added, the volatiles removed in a vacuum oven (40° C., 200 mbar), and the residual oil dissolved in THF (2 mL) to form "solution A". A mixture of 1-{4-chloro-2-[6-(2,5-dimethyl-pyrrol-1-yl)-pyridin-2-ylamino]-phenyl}-3-phenyl-propan-1-one (430 mg) in THF (2 mL) was treated with DMF (2 drops) and NaHMDS solution (2.5 mL, 1 M in THF) was added dropwise. Solution A (2 mL) was added dropwise, and the mixture stirred at RT for 12 h. The product was worked up in EtOAc/$H_2O$ and chromatographed (DCM/MeOH 100:0 to 70:30) to provide 3-benzyl-7-chloro-1-[6-(2,5-dimethyl-pyrrol-1-yl)-pyridin-2-yl]-2-oxazol-2-yl-1H-quinolin-4-one.

Step F: A solution of 3-benzyl-7-chloro-1-[6-(2,5-dimethyl-pyrrol-1-yl)-pyridin-2-yl]-2-oxazol-2-yl-1H-quinolin-4-one (640 mg) in EtOH (3.5 mL) and water (1.3 mL) and hydroxylamine hydrochloride (450 mg) was stirred for 48 h at 60° C. After evaporation of volatiles, the dark brown residue was partitioned into EtOAc and $H_2O$, and the organic phase adsorbed on silica to provide 1-(6-amino-pyridin-2-yl)-3-benzyl-7-chloro-2-oxazol-2-yl-1H-quinolin-4-one (Compound 141). M+H=428; mp=279.3-282.8° C.

Example 33

Synthesis of 3-Cyclopropylmethyl-7-methyl-4-oxo-1-phenyl-1,4-dihydro[1,8]-naphthyridine-2-carboxylic acid methyl ester (compound 142)

Step A: To 1-(6-methyl-2-phenylamino-pyridin-3-yl)-ethanone (0.7 g) dissolved in warm MeOH (15 mL) was added cyclopropanecarbaldehyde (0.4 g) and NaOH (2 M, 2.5 mL), and the mixture heated to 60° C. overnight. The mixture was then cooled to RT, partitioned between EtOAc and $H_2O$, and the organic layer washed with LiCl (0.3 wt % aq), dried over $MgSO_4$, filtered, and concentrated. The product was purified by column chromatography (1:4 EtOAc:hexane), and concentrated to a yellow oil to provide 3-cyclopropyl-1-(t-methyl-2-phenylamino-pyridin-3-yl)-propenone (0.32 g).

Step B: 3-cyclopropyl-1-(t-methyl-2-phenylamino-pyridin-3-yl)-propenone (0.32 g) was dissolved in EtOH/THF/EtOAc (12 mL), and Pd/C added (0.02 g, 10 wt %). The flask was evacuated and backfilled twice with $H_2$. After 2 h, the mixture was filtered through celite, concentrated, and purified by column using 1:8 EtOAc/hexane to provide 3-cyclopropyl-1-(t-methyl-2-phenylamino-pyridin-3-yl)-propan-1-one (0.34 g) as a yellow solid.

Step C: 3-Cyclopropyl-1-(t-methyl-2-phenylamino-pyridin-3-yl)-propan-1-one (0.3 g) was dissolved in THF and toluene (10 mL), oxalyl chloride (0.3 g) added, and the mixture heated at 80° C. for 2.5 h. The mixture was then allowed to cool to RT overnight, then again heated to 80° C. for 2.5 h, and cooled to RT to provide N-[3-(3-cyclopropyl-propionyl)-6-methyl-pyridin-2-yl]-N-phenyl-oxalamic acid methyl ester.

Step D: To N-[3-(3-cyclopropyl-propionyl)-6-methyl-pyridin-2-yl]-N-phenyl-oxalamic acid methyl ester (~0.3 g) dissolved in toluene was added MeOH (5 mL) and $K_2CO_3$ (0.3 g). The mixture was heated to 80° C. for 30 min, cooled to RT, then taken up in EtOAc and washed 2× with LiCl (0.3 wt %, aq). The product was dried over $MgSO_4$, filtered and concentrated, then purified by prep TLC (1:4 EtOAc/hexane) to provide 3-cyclopropylmethyl-7-methyl-4-oxo-1-phenyl-1,4-dihydro[1,8]naphthyridine-2-carboxylic acid methyl ester (compound 142).

Example 34

Formulations

Pharmaceutical preparations for delivery by various routes are formulated as shown in the following Tables. "Active ingredient" or "Active compound" as used in the Tables means one or more of the compounds of Formula I.

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration

| Ingredient | Amount |
|---|---|
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation

| Ingredient | % wt./wt. |
|---|---|
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation

| Ingredient | % wt./wt. |
|---|---|
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation

| Ingredients | grams |
|---|---|
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 µL of formulation per actuation. A typical dosing schedule is 2-4 sprays every 4-12 h.

Example 35

JNK Assay in vitro

JNK activity was measured by phosphorylation of GST-ATF2 (19-96) with [γ-$^{33}$P] ATP. The enzyme reaction was conducted at Km concentrations of ATP and the substrate at final volume of 40 µl in buffer containing 25 mM HEPES, pH 7.5, 2 mM dithiothreitol, 150 mM NaCl, 20 mM MgCl$_2$, 0.001% Tween® 20, 0.1% BSA and 10% DMSO. Human JNK2α2 assay contains 1 nM enzyme, 1 µM ATF2, 8 µM ATP with 1 uCi [γ-$^{33}$P] ATP. Human JNK1α1 assay contains 2 nM enzyme, 1 µM ATF2, 6 µM ATP with 1 µCi [γ-$^{33}$P] ATP. Human JNK3 (Upstate Biotech #14-501M) assay contains 2 nM enzyme, 1 µM ATF2, 4 µM ATP with 1 µCi [γ-$^{33}$P] ATP. The enzyme assay was carried out in the presence or absence of several compound concentrations. JNK and compound were pre-incubated for 10 min., followed by initiation of the enzymatic reaction by adding ATP and the substrate. The reaction mixture was incubated at 30° C. for 30 min. At the end of incubation, the reaction was terminated by transferring 25 µl of the reaction mixture to 150 µl of 10% glutathione Sepharose® slurry (Amersham #27-4574-01) containing 135 mM EDTA. The reaction product was captured on the affinity resin, and washed on a filtration plate (Millipore, MAB-VNOB50) with phosphate buffered saline for six times to remove free radionucleotide. The incorporation of $^{33}$P into ATF2 was quantified on a microplate scintillation counter (Packard Topcount). Compound inhibition potency on JNK was measured by IC$_{50}$ value generated from ten concentration inhibition curves fitted into the 3-parameter model: % inhibition=Maximum/(1+(IC$_{50}$/[Inhibitor])$^{slope}$). Data were analyzed on Microsoft Excel for parameter estimation. The results are shown in Table 2 below:

TABLE 2

Compound IC$_{50}$'s vs. JNK1 and JNK2

| Compound | JNK1 (µM) | JNK2 (µM) |
|---|---|---|
| 66 | 0.0181 | 0.0445 |
| 69 | 0.0184 | 0.047 |
| 59 | 0.0226 | 0.0614 |
| 67 | 0.0304 | 0.0485 |
| 65 | 0.0328 | 0.0957 |
| 87 | 0.0334 | 0.0832 |
| 30 | 0.0355 | 0.0863 |
| 32 | 0.0445 | 0.1289 |
| 46 | 0.0454 | 0.1367 |
| 85 | 0.0481 | 0.1178 |
| 44 | 0.0491 | 0.1682 |
| 31 | 0.0529 | 0.1612 |
| 63 | 0.0987 | 0.212 |

TABLE 2-continued

Compound IC$_{50}$'s vs. JNK1 and JNK2

| Compound | JNK1 (µM) | JNK2 (µM) |
|---|---|---|
| 70 | 0.1342 | 0.3988 |
| 72 | 0.1544 | 0.3362 |
| 80 | 0.1931 | 0.4773 |
| 88 | 0.2454 | 0.8402 |
| 64 | 0.6032 | 2.0554 |
| 60 | 1.6324 | 4.9829 |
| 100 | 01148 | 0.2257 |
| 110 | 0.0502 | 0.2014 |
| 117 | 0.032 | 0.0867 |
| 129 | 0.2523 | 0.5621 |
| 135 | 0.2496 | 2.103 |
| 141 | 0.612 | 2.086 |

Example 36

Rat in vivo TNFα-Induced IL-6 Production Assay

Female Wistar-Han rats procured from Charles River Laboratories were allowed to acclimate for one week prior to use and achieve an approximate body weight of 101-130 g. Rats were administered test compound (N=8 per compound) via oral gavage 30 min prior to an intraperitoneal challenge of 0.5 µg recombinant rat TNF-α (Biosource). Blood was collected via cardiocentesis 90 min after TNF-α challenge. Plasma was prepared using lithium heparin separation tubes (BD microtainer) and frozen at −80° C. until analyzed. IL-6 levels were determined using a rat specific IL-6 ELISA kit (Biosource). The percent inhibition and ED$_{50}$ values (calculated as the dose of compound at which TNF-α production is 50% of the control value) were determined. The results are shown in Table 3 below:

TABLE 3

Inhibition of IL-6 Production

| Compound | Dose (mg/Kg) | IL-6 Inhibition (%) |
|---|---|---|
| 18 | 3 | 53 |
| 30 | 30 | 46 |

Example 37

Rat in vivo TNFα-Induced IL-6 Production Assay

Female Wistar-Han rats procured from Charles River Laboratories were allowed to acclimate for one week prior to use and achieve an approximate body weight of 114-132 g. Rats were administered compound 18 (N=8 per dose) subcutaneously 30 min prior to an intra-peritoneal challenge of 0.5 µg recombinant rat TNF-α (Biosource). Blood was collected via cardiocentesis 90 min after TNF-α challenge. Plasma was prepared using lithium heparin separation tubes (BD microtainer) and frozen at −80° C. until analyzed. IL-6 levels were determined using a rat specific IL-6 ELISA kit (Biosource). The percent inhibition and ED$_{50}$ values (calculated as the dose of compound at which TNF-α production is 50% of the control value) were determined. The results are shown in Table 4 below:

TABLE 4

Inhibition of IL-6 Production

| Dose (mg/Kg) | IL-6 Inhibition (%) | p vs. vehicle |
|---|---|---|
| 0.03 | NS | NS |
| 0.1 | NS | NS |
| 0.3 | 30.01 | 0.01 |
| 1.0 | 47.83 | 0.002 |
| 3.0 | 54.85 | 0.0003 |
| 10 | 71.15 | 0.0002 |

Example 38

Rodent Collagen-induced Arthritis

Female Lewis rats procured from Harlan Laboratories at 7-8 weeks of age are allowed to acclimate for one week prior to use and achieve an approximate body weight of 120-140 g. On day 0 of study, rats are primed intradermally (i.d.) on several sites on the back with an emulsion of 100 µg Bovine Type II Collagen (Chondrex) in Incomplete Freund's adjuvant (IFA; total of 0.1 ml in 2-3 sites). Arthritis induction is generally observed 12-14 days from priming; however a booster injection of 100 µg collagen/IFA is given around days 7-10 (i.d. up to 0.1 ml total) at the base of the tail or an alternate site on back to synchronize disease induction. Compound dosing can be prophylactic (starting at time of boost or 1-2 days prior) or therapeutic (beginning after boost and coinciding with initial disease scores of 1-2—see clinical scoring below). Animals are evaluated for the development and progression of disease over the next 21 days.

Rats are evaluated using a scoring system (described below), paw volume measurements using a plethysmometer for each paw, or measuring paw or joint thickness with a caliper. Base-line measurements are performed on day 0, and starting again at the first signs of swelling for up to three times per week until the end of the experiment. Scoring is evaluated as follows for each paw:

1=swelling and/or redness of paw or one digit.
2=swelling in two or more joints.
3=gross swelling of the paw with more than two joints involved.
4=severe arthritis of the entire paw and digits.

The arthritic index for each rat is evaluated by adding the four scores of the individual paws, giving a maximum score of 16. In order to serially measure disease onset and progression, the paw volume of the hind paws is also determined through the use of a plethysmometer.

At the end of the study, the hind paws (and other tissues) are harvested for weight determination, histology, cellular and/or molecular analysis. Additionally, blood is collected via cardiocentesis, plasma is prepared using lithium heparin separation tubes (BD microtainer) and frozen at −70° C. until analyzed. Inflammatory cytokine levels (e.g., TNF-α, IL-1 and IL-6) from the plasma or from homogenized joint tissue are determined using rat-specific ELISA kits (R&D). The level of disease protection or inhibition is determined as a composite of changes in clinical scores, paw volumes and histopathology compared to control animals.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present inven-

What is claimed:

1. A compound of formula I

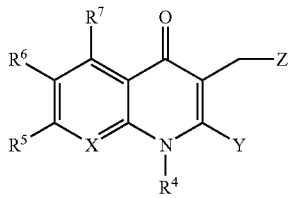

wherein
X is $CR^{11}$ or N;
Y is —C(O)$R^3$, 5-membered heteroaryl, or 5-membered heterocyclyl;
Z is phenyl, cycloalkyl, heterocyclyl or heteroaryl, and is substituted with $R^1$ and $R^2$;
$R^1$ and $R^2$ are each independently H, halo, CN, lower alkyl, or —$Y^1$—$Y^2$—$Y^3$—$R^8$, or $R^1$ and $R^2$ together form —O(CH$_2$)$_n$O—, where n is 1 or 2;
 $Y^1$ is —O—, —C(O)—, —C(O)O—, —C(O)N$R^9$—, —N$R^9$C(O)—, —S—, —SO$_2$—, or a bond;
 $Y^2$ is cycloalkylene, heterocycloalkylene, lower alkylene or a bond;
 $Y^3$ is —O—, —C(O)—, —C(O)O—, —C(O)N$R^9$—, —N$R^9$C(O)—, —SO$_2$—, or a bond;
 $R^8$ is H, lower alkyl, lower alkoxy, cycloalkyl, heterocycloalkyl, or —N$R^9R^{10}$, wherein $R^8$ other than H is optionally substituted with lower alkyl, halo, —CF$_3$, or —OH;
 $R^9$ and $R^{10}$ are each independently H or lower alkyl;
$R^3$ is OH, lower alkyl, lower alkoxy, (lower alkoxy)-lower alkoxy, or —N$R^9R^{10}$;
$R^4$ is lower alkyl, phenyl, heterocyclyl, cycloalkyl, or heteroaryl, and is optionally substituted with lower alkyl, hydroxy, lower alkoxy, halo, nitro, amino, cyano, or halo-lower alkyl;
$R^5$ and $R^6$ are each independently H, halo, cyano, lower alkyl, —CF$_3$, lower alkoxy, —OCHF$_2$, —NO$_2$, or —N$R^9R^{10}$;
$R^7$ is H, F, Cl, methyl, or OH;
$R^{11}$ is H, lower alkyl, lower cycloalkyl, or phenyl;
or a pharmaceutically acceptable salt thereof.

2. The compound of claim 1, wherein Y is —C(O)$R^3$, and $R^3$ is methoxy.

3. The compound of claim 2, wherein $R^7$ is H.

4. The compound of claim 3, wherein Z is phenyl, and $R^2$ is H.

5. The compound of claim 4, wherein $R^6$ is H.

6. The compound of claim 5, wherein $R^5$ is selected from the group consisting of H, F, Cl, Me, and CF$_3$.

7. The compound of claim 6, wherein X is CH.

8. The compound of claim 6, wherein X is N.

9. The compound of claim 6, wherein $R^2$ is H.

10. The compound of claim 9, wherein $R^1$ is —$Y^1$—$Y^2$—$Y^3$—$R^8$, and $Y^1$ is SO$_2$.

11. The compound of claim 10, wherein $Y^2$ is a bond, $Y^3$ is a bond, and $R^8$ is lower alkyl.

12. The compound of claim 10, wherein $R^8$ is substituted with hydroxy.

13. The compound of claim 3, wherein Z is selected from the group consisting of piperidyl, pyrrolidyl, cyclopropyl, pyrazolyl, piperazinyl, morpholino, and pyrimidinyl.

14. A pharmaceutical composition, comprising:
a compound of formula I:

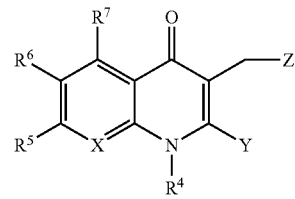

wherein
X is $CR^{11}$ or N;
Y is —C(O)$R^3$, 5-membered heteroaryl, or 5-membered heterocyclyl;
Z is phenyl, cycloalkyl, heterocyclyl or heteroaryl, and is substituted with $R^1$ and $R^2$;
$R^1$ and $R^2$ are each independently H, halo, CN, lower alkyl, or —$Y^1$—$Y^2$—$Y^3$—$R^8$, or $R^1$ and $R^2$ together form —O(CH$_2$)$_n$O—, where n is 1 or 2;
 $Y^1$ is —O—, —C(O)—, —C(O)O—, —C(O)N$R^9$—, —N$R^9$C(O)—, —S—, —SO$_2$—, or a bond;
 $Y^2$ is cycloalkylene, heterocycloalkylene, lower alkylene or a bond;
 $Y^3$ is —O—, —C(O)—, —C(O)O—, —C(O)N$R^9$—, —N$R^9$C(O)—, —SO$_2$—, or a bond;
 $R^8$ is H, lower alkyl, lower alkoxy, cycloalkyl, heterocycloalkyl, or —N$R^9R^{10}$, wherein $R^8$ other than H is optionally substituted with lower alkyl, halo, —CF$_3$, or —OH;
 $R^9$ and $R^{10}$ are each independently H or lower alkyl;
$R^3$ is OH, lower alkyl, lower alkoxy, (lower alkoxy)-lower alkoxy, or —N$R^9R^{10}$;
$R^4$ is lower alkyl, phenyl, heterocyclyl, cycloalkyl, or heteroaryl, and is optionally substituted with lower alkyl, hydroxy, lower alkoxy, halo, nitro, amino, cyano, or halo-lower alkyl;
$R^5$ and $R^6$ are each independently H, halo, cyano, lower alkyl, —CF$_3$, lower alkoxy, —OCHF$_2$, —NO$_2$, or —N$R^9R^{10}$;
$R^7$ is H, F, Cl, methyl, or OH;
$R^{11}$ is H, lower alkyl, lower cycloalkyl, or phenyl;
or a pharmaceutically acceptable salt thereof;
and a pharmaceutically acceptable excipient.

* * * * *